(12) United States Patent
Bogdanov et al.

(10) Patent No.: US 8,153,784 B2
(45) Date of Patent: Apr. 10, 2012

(54) IMAGING OF ENZYME ACTIVITY

(75) Inventors: Alexei Bogdanov, Westborough, MA (US); John W. Chen, Quincy, MA (US); Ralph Weissleder, Peabody, MA (US); Manel Querol, Calig (ES)

(73) Assignee: The General Hospital Corporation, Boston, MA (US)

( * ) Notice: Subject to any disclaimer, the term of this patent is extended or adjusted under 35 U.S.C. 154(b) by 1222 days.

(21) Appl. No.: 11/631,720

(22) PCT Filed: Jul. 7, 2005

(86) PCT No.: PCT/US2005/024065
§ 371 (c)(1),
(2), (4) Date: Jul. 30, 2007

(87) PCT Pub. No.: WO2006/014530
PCT Pub. Date: Feb. 9, 2006

(65) Prior Publication Data
US 2008/0044827 A1 Feb. 21, 2008

Related U.S. Application Data

(60) Provisional application No. 60/586,152, filed on Jul. 7, 2004, provisional application No. 60/665,027, filed on Mar. 24, 2005.

(51) Int. Cl.
*C07D 225/00* (2006.01)
*C07D 245/00* (2006.01)
(52) U.S. Cl. .................... 540/465; 540/472
(58) Field of Classification Search .............. None
See application file for complete search history.

(56) References Cited

U.S. PATENT DOCUMENTS 5,817,774 A 10/1998 Delecki et al.
6,737,247 B2 * 5/2004 Bogdanov et al. ........... 435/25
6,827,926 B2 * 12/2004 Robinson et al. ........... 424/9.1

FOREIGN PATENT DOCUMENTS

WO  WO 0045857    * 8/2000
WO  WO 02059122   * 8/2002
WO  2006/014530 A2  2/2006

OTHER PUBLICATIONS

Lim et al. Inorganic Chemistry, 2005, 44, pp. 2018-2030.*
International Search Report, Patent Cooperation Treaty, Dec. 5, 2007, 10 pages.
Akkara et al., "Biomimetic Membrane and Interface Templates for Enzyme-Based Polymerization Reactions," *Biomimetics*, 2:331-339 (1994).
Akkara et al., "Synthesis and characterization of polymers produced by horseradish peroxidase in dioxane," *J. Polymer. Sci.*, 29:1561-1574 (1991).
Bogdanov et al., "Oligomerization of Paramagnetic Substrates Result in Signal Amplification and can be Used for MR Imaging of Molecular Targets," *Molecular Imaging*, 1(1):16-23 (2002).
Chen et al., "Human myeloperoxidase: a potential target for molecular MR imaging in atherosclerosis," *Magn. Reson. Med.*, 52:1021-1028 (2004).
Crestini et al., "The reactivity of phenolic and non-phenolic residual kraft liglnin model compounds with Mn(II)-peroxidase from Lentinula edodes," *Bioorg. Med. Chem.*, 8:433-438 (2000).
Dunford et al., "Kinetics of oxidation of serotonin by myeloperoxidase compounds I and II," *Biochem Cell Biol.*, 77:449-457 (1999).
Guerra et al., "Polymerization of lignin fragments contained in a model effluent by polyphenoloxidases and horseradish peroxidase/hydrogen peroxide system," *Enzyme Microb. Technol.*, 26:315-323 (2000).
Heinecke et al., "Dityrosine, a specific marker of oxidation, is synthesized by the myeloperoxidase-hydrogen peroxide system of human neutrophils and macrophages," *J. Biol. Chem.*, 268:4069-4077 (1993).
Huether et al., "Oxidation of the indole nucleus of 5-hydroxytryptamine and formation of dimmers in the presence of peroxidase and $H_2O_2$," *J. Neural. Transm. Suppl.*, 32:249-257 (1990).
Klebanoff et al., "Oxygen radicals in biological systems," *Methods Enzymol*, 105:399-403 (1984).
Michon et al., "Horseradish peroxidase oxidation of tyrosine-containing peptides and their subsequent polymerization: a kinetic study," *Biochemistry*, 36:8504-8513 (1997).
Negrin et al., "In vivo-in vitro study of biodegradable methadone delivery systems," *Biomaterials*, 22(6):563 (2001).
Querol et al., "DTPA-bisamide-based MR sensor agents for peroxidase imaging," *Org. Lett.*, 7:1719-1722 (2005).
Rausch et al., "Granule enzymes of polymorphonuclear neutrophils: a phylogenetic comparison," *Blood*, 46:913-919 (1975).
Wade "Reactions of benzene and its derivatives," *Organic Chemistry*, 666-669 (1988).

* cited by examiner

*Primary Examiner* — Noble Jarrell
(74) *Attorney, Agent, or Firm* — Fish & Richardson P.C.

(57) ABSTRACT

This invention relates to biochemistry and magnetic resonance imaging.

24 Claims, 32 Drawing Sheets

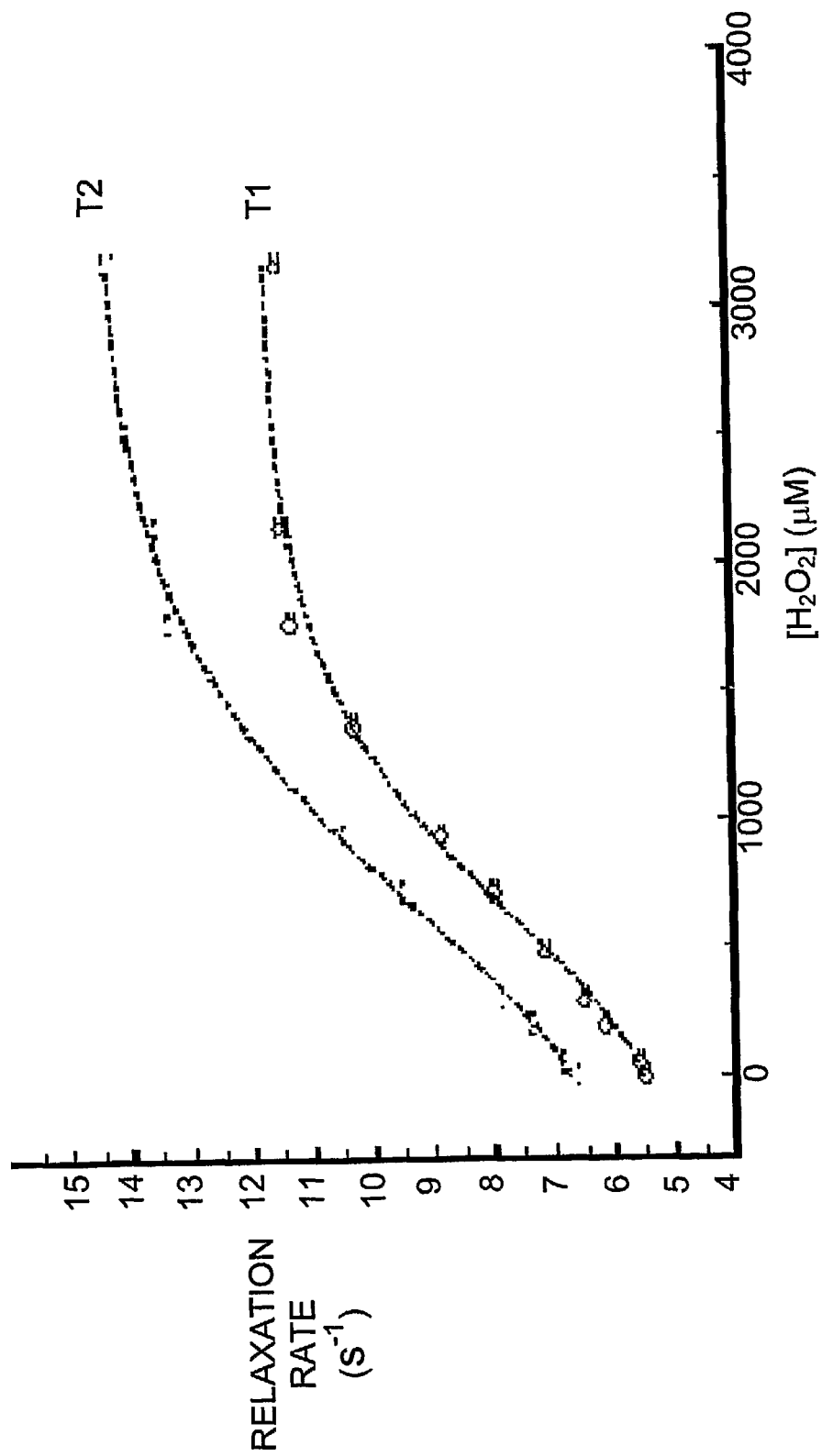

FIG. 6A  FIG. 6B  FIG. 6C
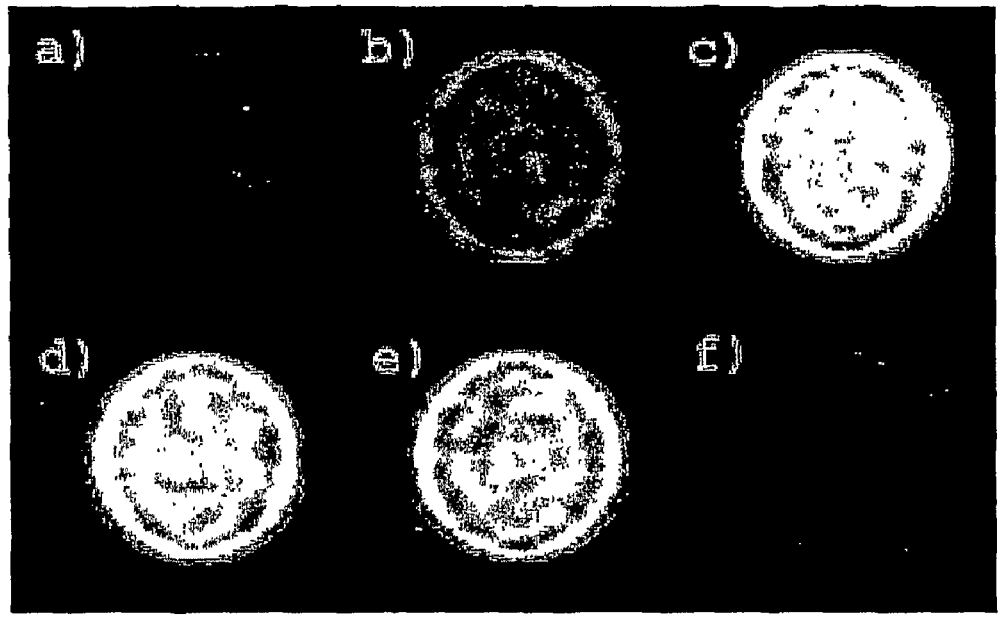
FIG. 6D  FIG. 6E  FIG. 6F
FIG. 7A  FIG. 7B  FIG. 7C
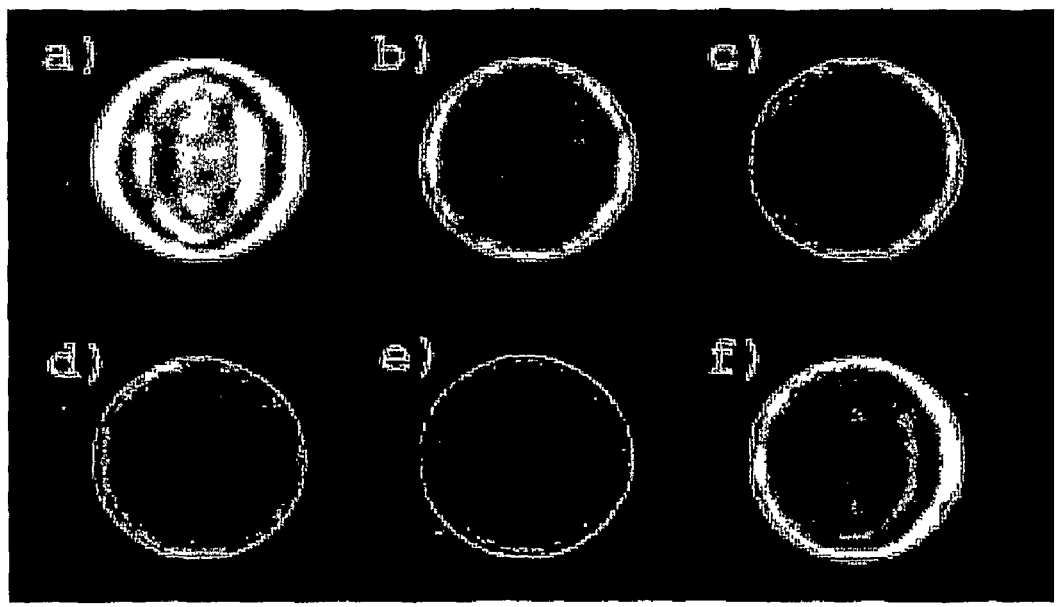
FIG. 7D  FIG. 7E  FIG. 7F

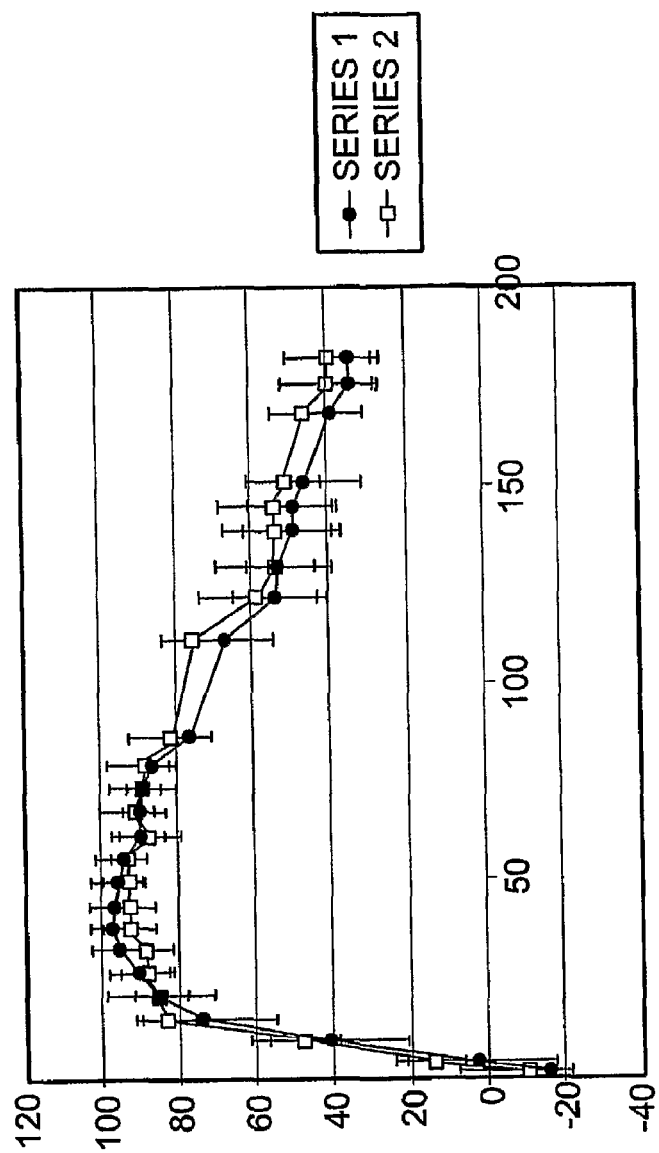
FIG. 16A

| MPO | 1.18 | 1.49 (1.39)* |
|---|---|---|
| HRP | 1.59 | 1.76 (1.63)* |
| No Enz. | 1 | 1.08 (1)* |
| Added | 25μL $1^{67}$Ga 12.5μC | 50μL $1^{67}$Ga 25μC |

* Values in bracket are standardized to 1.08

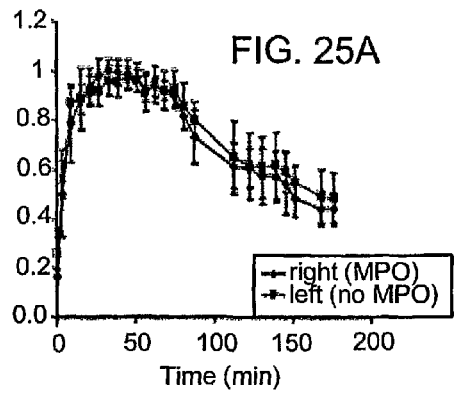
FIG. 25A
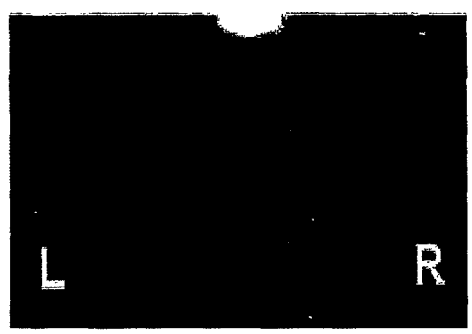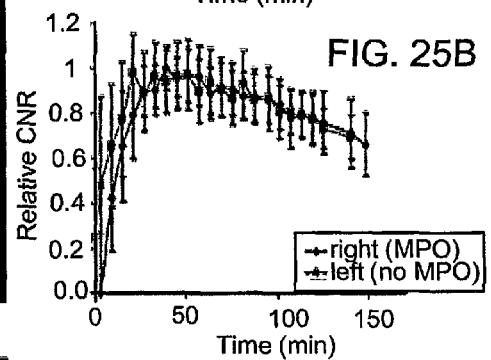
FIG. 25B
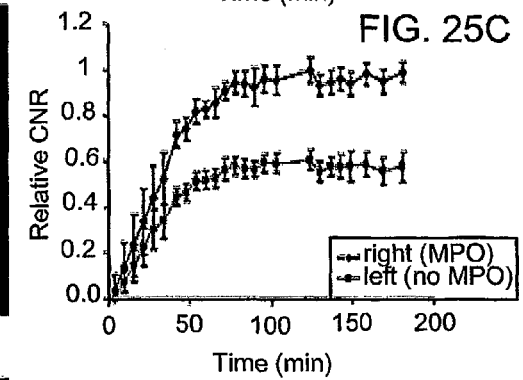
FIG. 25C
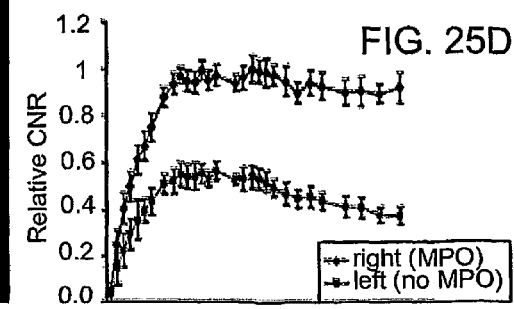
FIG. 25D

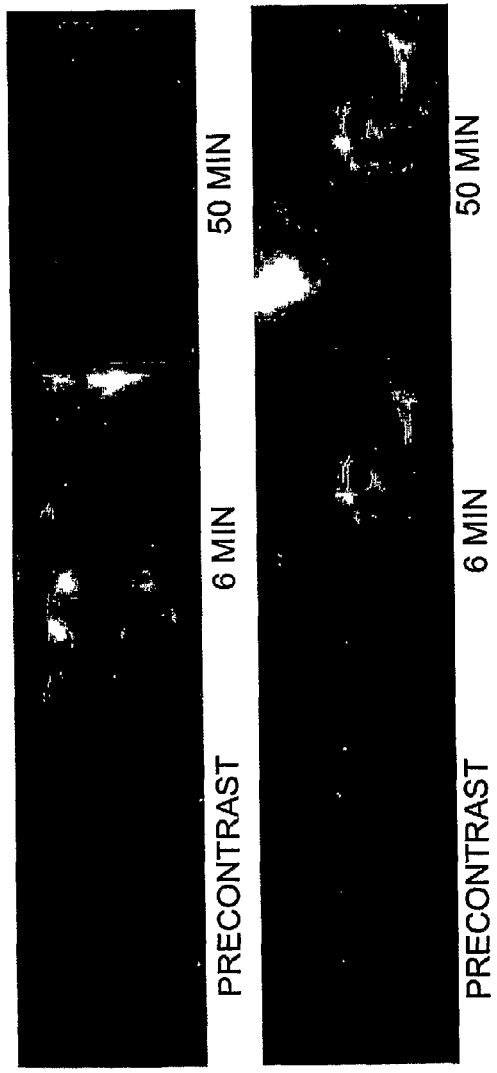
FIG. 26A
FIG. 26B
FIG. 26D WITH LPS
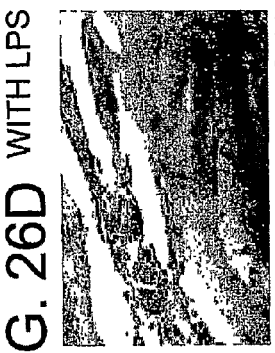
FIG. 26E CONTROL
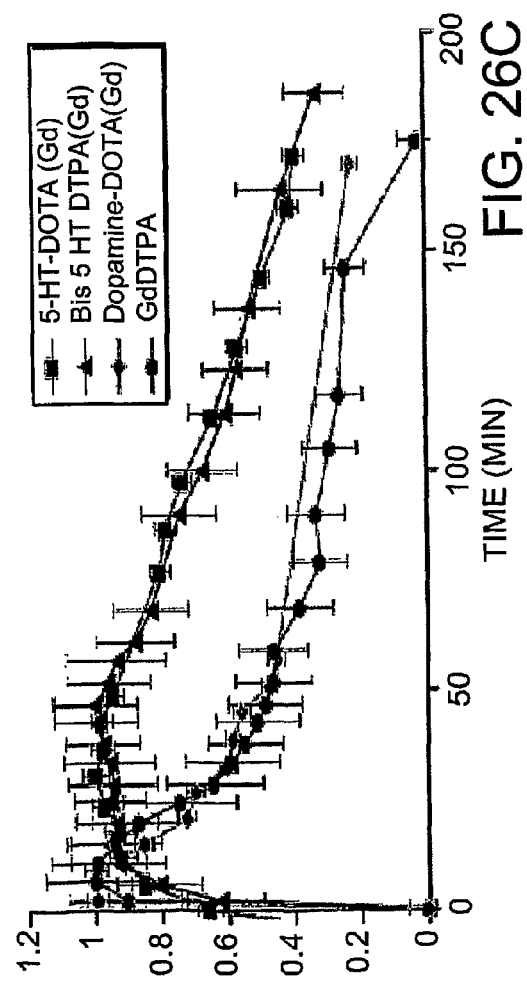
FIG. 26C

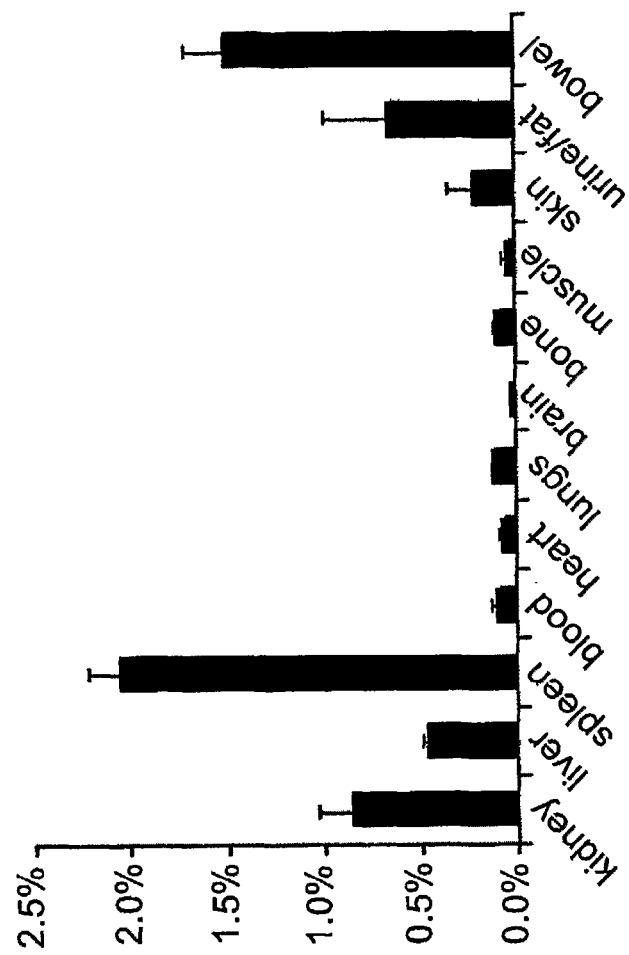
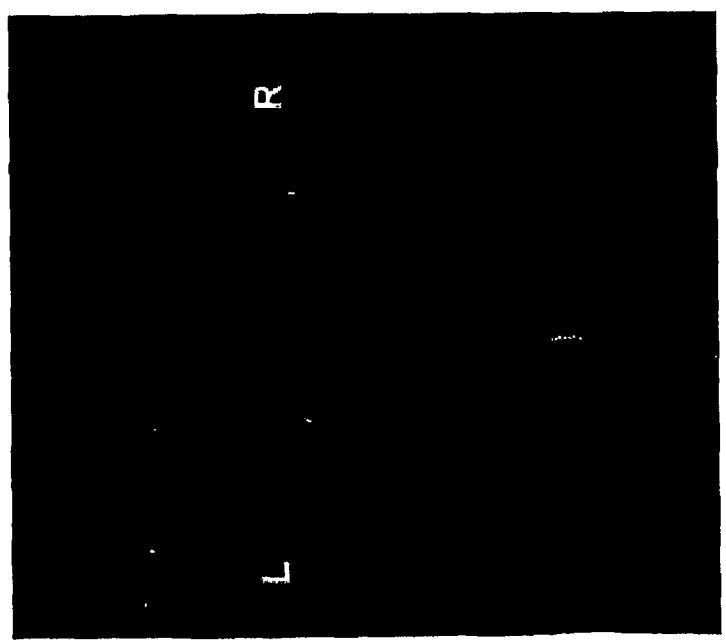
FIG. 27B
FIG. 27A

US 8,153,784 B2

IMAGING OF ENZYME ACTIVITY

CROSS-REFERENCE TO RELATED APPLICATIONS

This application is a national phase application under 35 U.S.C. §371 of PCT International Application No. PCT/US2005/024065, filed Jul. 7, 2005, which claims the benefit of U.S. Provisional Application No. 60/586,152, filed on Jul. 7, 2004 and U.S. Provisional Application No. 60/665,027, filed on Mar. 24, 2005. The contents of each of these prior applications are incorporated herein by reference in their entireties.

STATEMENT REGARDING FEDERALLY SPONSORED RESEARCH

The work described herein was carried out, at least in part, using funds from a federal grant RO1EB000858. The government therefore has certain rights in the invention.

TECHNICAL FIELD

This invention relates to biochemistry and magnetic resonance imaging.

BACKGROUND

Magnetic resonance imaging (MRI) has become a leading tool for imaging fine details of anatomy and physiology as well as functional imaging.

MRI offers certain known advantages as a non-invasive imaging technology. For example, MRI can potentially provide exceptionally high anatomic resolution approaching single-cell levels (voxel of 20-40 μm$^3$). Recent innovations in instrument design and contrast agent development indicate that the above level of resolution can be achieved non-invasively in vivo. Moreover, MRI can be used at tissue depths where optical reporting methods can sometimes be complicated by light scattering and absorption by the tissue, e.g., tissue depths greater than about 250 μm. One of the future directions of in vivo MRI research includes mapping of specific molecules (e.g., receptors) and detecting patterns of their expression.

In both clinical and research settings, MRI techniques can benefit from the use of biocompatible contrast agents (CAs), which enhance the image contrast by shortening of proton relaxation times ($T_1$ and $T_2$) of water molecules. This shortening of $T_1$ and $T_2$ produces subtle local MR signal changes, which can be detected, giving rise to enhanced signal-to-noise ratios and, in many cases, providing reasonably exact spatial locations if the MR signal changes are mapped versus non-influenced water molecules in a target tissue volume. Accordingly, it is desirable for in vivo imaging applications that CAs exhibit relatively high atomic relaxivities, $r_{1p}$, which is defined as the shortening of water proton relaxation rates in presence of CAs, normalized per concentration of a paramagnetic element. In some instances, the $r_{1p}$ of some CAs can be enhanced by covalent or noncovalent association of the CAs with a preformed macromolecule, e.g., a protein, a polypeptide, a dendrimer, or a graft-copolymer.

It has previously been demonstrated that reducing substrates can be made paramagnetic. For example, hydroxytyramine and serotonin can be acylated with derivatives of monosubstituted DOTA(Gd) (gadolinium salt of 1,4,7,10-tetraazacyclododecane-1,4,7-tris(acetic acid)) and successfully used as an electron donor in horseradish peroxidase and myeloperoxidase-catalyzed reaction of hydrogen peroxide reduction. Peroxidase reduction generates radicals that polymerize rapidly. For example, formation of polymers has been demonstrated in the case of tyrosine. Polymerization of these low molecular weight paramagnetic molecules results in an increase of proton relaxivity, i.e., the ability of gadolinium to shorten relaxation times of water protons. As a result, the enzyme-mediated conversion of the substrate into polymerized products was detected using magnetic resonance imaging (MRI).

SUMMARY

This invention relates to compounds (e.g., monomeric substrates) and compositions thereof as well as methods of manufacture and use thereof for noninvasive, magnetic resonance imaging of enzymatic activity (e.g., oxidoreductase activity; e.g., myeloperoxidase (MPO) activity, e.g., magnetic resonance imaging of myeloperoxidase activity in arteries where the MPO activity can indicate the presence of a vulnerable plaque).

The methods and compositions feature compounds (e.g., monomeric substrates), which are capable of chelating a metal atom or ion (e.g., gadolinium (Gd) or gallium (Ga)) and, upon interaction with an enzyme (e.g., a target enzyme), are capable of being chemically modified and subsequently undergoing one or more chemical reactions that result in the formation of monomeric substrate-containing product(s) having a higher molecular weight than that of the starting monomeric substrate itself (e.g., 2, 3, 4, 5, 6, 7, 8, 9, 10, 20, 50, 100, 1,000, 5,000, 10,000, 50,000, 100,000, 300,000, 500,000, 1,000,000 times higher than that of the substrate itself) In certain embodiments, the products have a molecular weight that is from about 2-100 (e.g., 2-50, 2-25, 2-10, 2-5) times higher than that of the substrate itself.

Substrate monomers can undergo, for example (and without limitation), one or more or more of the following processes:

(a) enzyme-dependent polymerization or co-polymerization (as well as oligomerization) of the monomeric substrate (MS), resulting in the formation of polymeric or oligomeric products having monomeric substrate repeat subunits (e.g., polymers or co-polymers comprising structures such as -MS-[MS]-MS- or MS-[MS]-MS-, in which "MS" is a monomer substrate subunit); such oligomers or polymers can also be crosslinked; and/or (b) enzyme-mediated binding (e.g., covalent binding) of the monomeric substrate (or oligomers or polymers thereof) to high molecular weight molecules (e.g., macromolecules having a molecular weight of from at least about 1 kiloDaltons (kD) to about 2000 kD (e.g., 1-1,000, 1-500, 1-100, 1-50, 1-10, 1-5, 1-3 kD) other than those intermediates or products formed in process (a) (i.e., a macromolecule that is substantially free of monomeric substrate repeat subunits, e.g., a macromolecule present in biological systems, such as a protein) to form addition products (e.g., complexes) resulting from the interaction and attachment of the substrate (or oligomers and polymers thereof) to the high molecular weight chemical compounds; for example, one or more monomeric substrates can each bind to separate sites on a macromolecule (e.g., a protein, (A-A-A-A-A)), or polymerized substrates can bind to a macromolecule (e.g., a protein, (A-A-A-A-A)) to form products having structures, for example, such as A(MS)-A-A-A(MS)-A or MS-[MS]-MS-A-A-A-A-A.

In general, monomeric substrates include (i) a chelator moiety for chelating a metal atom or ion and (ii) one or more (e.g., 1, 2, 3, 4, 5, 6, 7, 8, 9, 10) polymerizing moieties, which upon interaction with an enzyme (e.g., a target enzyme), can be chemically modified. In general, the polymerizing moiety serves as the site of reaction when the monomeric substrate undergoes the enzyme-mediated polymerization, co-polymerization, or binding processes as described herein. Monomeric substrates can also include one or more linker moieties to connect the chelator moiety to the polymerizing moiety (ies).

In one aspect, this invention features monomeric substrates having formula (I):

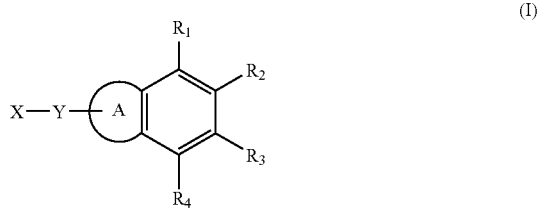

wherein X comprises a chelator moiety; Y comprises a linker moiety; A is a monocyclic, bicyclic, tricyclic, or polycyclic moiety, optionally having one or more double bonds and/or optionally inserted with one or more heteroatoms; and each of $R_1$, $R_2$, $R_3$, and $R_4$ is selected from the group consisting of hydrogen, hydroxy, $C_1$-$C_6$ alkoxy, amino, $C_1$-$C_6$ alkylamino, $C_1$-$C_6$ dialkylamino, and $C_1$-$C_6$ alkylcarboxamido; provided that at least one of $R_1$, $R_2$, $R_3$, and $R_4$ is hydroxy; or a salt thereof.

In another aspect, the invention features methods of detecting a target enzyme (e.g., myeloperoxidase) in a sample (using magnetic resonance imaging) by: (i) providing a monomeric substrate having a formula (I) in which X includes a chelator moiety and a chelated paramagnetic or superparamagnetic metal atom or ion, and Y, A, $R_1$, $R_2$, $R_3$, and $R_4$ are as described herein for formula (I) (e.g., a monomeric substrate of formula (I) that is polymerizable in the presence of the target enzyme (e.g., myeloperoxidase) or as a result of a target enzyme (e.g., myeloperoxidase)-catalyzed reaction); (ii) contacting the substrate with a sample, wherein the substrate undergoes polymerization to form a paramagnetic or superparamagnetic polymer in the presence of a sufficient amount of the target enzyme (e.g., myeloperoxidase) in the sample; and (iii) measuring relaxivity and/or magnetic resonance (MR) signal intensity of the sample; wherein an increase in relaxivity and/or MR signal intensity in the sample relative to an equivalent amount of unpolymerized substrate in a sample without the target enzyme (e.g., myeloperoxidase) indicates the presence of the target enzyme (e.g., myeloperoxidase) in the sample.

In a further aspect, the invention features methods of detecting a target enzyme (e.g., myeloperoxidase) in a sample (using magnetic resonance imaging) by: (i) providing a monomeric substrate having formula (I) as described herein (a monomeric substrate that can be chemically modified in the presence of (e.g., upon interaction with) the target enzyme (e.g., myeloperoxidase) or as a result of a target enzyme (e.g., myeloperoxidase)-catalyzed reaction (e.g., (a) the chemically modified substrates can polymerize to form a paramagnetic or superparamagnetic polymer or copolymer comprising monomeric substrate repeat subunits and/or (b) the chemically modified substrates (or oligomers or products thereof) can bind to a macromolecule in the sample that is substantially free of monomeric substrate repeat subunits); (ii) contacting the substrate with a sample, wherein the substrate forms a paramagnetic or superparamagnetic substance having a molecular weight greater than that of the substrate in the presence of a sufficient amount of the target enzyme (e.g., myeloperoxidase) in the sample (e.g., (a) the substrate undergoes polymerization to form a paramagnetic or superparamagnetic polymer or copolymer comprising monomeric substrate repeat subunits and/or (b) one or more substrates (or a polymerized substrate) bind to a macromolecule (also present in the sample) that is substantially free of monomeric substrate repeat subunits); and (iii) measuring the relaxivity or shortening of relaxation times or magnetic resonance signal intensity of the sample; wherein an increase in relaxivity or MR signal intensity in the sample relative to an equivalent amount of the substrate provided in step (i) in a sample without the target enzyme (e.g., myeloperoxidase) (e.g., an equivalent amount of unpolymerized and/or unbound substrate) indicates the presence of the target enzyme (e.g., myeloperoxidase) in the sample.

In one aspect, the invention features methods for detecting a vulnerable atherosclerotic plaque in a subject using magnetic resonance imaging of myeloperoxidase activity by: (i) administering to the subject a monomeric substrate of formula (I) as described herein; (ii) allowing sufficient time for the substrate to accumulate in a target tissue (e.g., blood vessels or arteries) in the subject and to form a paramagnetic or superparamagnetic substance having a molecular weight greater than that of the substrate (e.g., via polymerization of the substrate or binding of the substrate or polymer thereof to a macromolecule), the formation of the paramagnetic or superparamagnetic substance being mediated by (e.g., catalyzed by) myeloperoxidase in the target tissue; and (iii) measuring the relaxivity or shortening of relaxation times or magnetic resonance signal intensity in the target tissue; wherein an increase in relaxivity or MR signal intensity in the sample relative to an equivalent amount of the substrate provided in step (i) in a target tissue without myeloperoxidase (e.g., an equivalent amount of unpolymerized and/or unbound substrate) indicates the presence of an atherosclerotic or vulverable plaque in the target tissue. The monomeric substrate can further include a targeting moiety, or be administered in sufficient quantity so as to fill the blood vessels or arteries.

In some embodiments, the subject is identified as being in need of such detecting. A subject in need of such detecting can be identified, for example, by the judgment of a subject or a health care professional and can be subjective (e.g. opinion) or objective (e.g. measurable by a test or diagnostic method). In some embodiments, the methods further include repeating the steps over time. In some embodiments, the subject is a mammal. In certain embodiments, the subject is a human.

In some embodiments, the method further include assessing the phase of atherosclerosis in the subject by measuring the level or amount of myeloperoxidase (e.g., absolute or relative measurement) present in the target tissue. Assessing the phase of atherosclerosis in the subject can further include determining whether such levels indicate the presence of a vulnerable plaque and whether there exists a high or low risk of rupture of the plaque (if present). Accordingly, in a further aspect, the invention features methods for the diagnosis of a vascular disease (e.g., cardiovascular disease, cerebrovascular disease, or peripheral vascular disease) in a subject using magnetic resonance imaging of myeloperoxidase as described herein. For example, using MRI in conjunction with the substrate monomers and methods described herein, a health care professional (e.g., radiologists) may locate (e.g., in a highly specific manner) vulnerable plaques before they become culprit lesions, and perform focused treatment.

Moreover, because patients can sometimes (in some instances, often) have more than one vulnerable plaque in different vascular territories, scintigraphic and/or MR imaging with the substrate monomers described herein can also be used in screening for the patients (e.g., vulnerable patients) for, e.g., systemic anti-inflammatory treatment.

In another aspect, the invention features other related methods for detecting a target enzyme (e.g., myeloperoxidase) in a sample using magnetic resonance imaging, methods for detecting a vulnerable atherosclerotic plaque in a subject, and methods for the diagnosis of vascular disease in a subject. In these methods, the monomeric substrates can have formula (I), and X can be a chelator moiety and a chelated radionuclide instead a chelator moiety and a chelated paramagnetic or superparamagnetic metal atom or ion. Y, A, $R_1$, $R_2$, $R_3$, and $R_4$ can be as described herein for formula (I).

In one aspect, the invention relates to monomeric substrates having: (i) a chelator moiety; and (ii) at least two polymerizing moieties, in which each polymerizing moiety is, independently of one another, attached directly, or indirectly with a linker moiety, to the chelator moiety; in which the monomeric substrate can be chemically modified when the monomeric substrate interacts with a target enzyme.

In another aspect, the invention features other related methods for detecting a target enzyme (e.g., myeloperoxidase) in a sample using magnetic resonance imaging, methods for detecting a vulnerable atherosclerotic plaque in a subject, and methods for the diagnosis of vascular disease in a subject. These methods feature the use of monomeric substrates having: (i) a chelator moiety and a chelated paramagnetic or superparamagnetic metal atom or ion (or radionuclide); and (ii) at least two polymerizing moieties, in which each polymerizing moiety is, independently of one another, attached directly, or indirectly with a linker moiety, to the chelator moiety; in which the monomeric substrate can be chemically modified when the monomeric substrate interacts with a target enzyme (e.g., each of the polymerizing moieties can be chemically modified when the monomeric substrate interacts with the target enzyme).

In some embodiments, the monomeric substrates have the following formula:

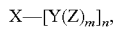

in which X includes a chelator moiety and a chelated paramagnetic or superparamagnetic metal atom or ion; each Y includes a linker moiety; each Z includes a polymerizing moiety; in which the monomeric substrate can be chemically modified when the monomeric substrate interacts with a target enzyme (e.g., each of the polymerizing moieties can be chemically modified when the monomeric substrate interacts with the target enzyme); m can be 1 or 2; and n can be 2, 3, 4, 5, or 6). In some embodiments, the X can be a chelator moiety and a chelated radionuclide instead a chelator moiety and a chelated paramagnetic or superparamagnetic metal atom or ion.

In some embodiments, the monomeric substrate undergoes polymerization in the presence of a sufficient amount of the target enzyme (e.g., myeloperoxidase) to form a polymer having a plurality of monomeric substrate subunits, in which at least one pair of monomeric substrate subunits is cross-linked; and/or the monomeric substrate can undergo copolymerization with one or more macromolecules, which are substantially free of monomeric substrate subunits, to form a copolymer having a plurality of monomeric substrate subunits and one or more macromolecules, in which at least one of the monomeric substrate subunits is cross-linked with another monomer subunit or the macromolecule.

In some embodiments, the monomeric substrate undergoes polymerization in the presence of a sufficient amount of the target enzyme (e.g., myeloperoxidase) to form a polymer having a plurality of monomeric substrate subunits, in which at least one pair of monomeric substrate subunits can be cross-linked.

In some embodiments, the monomeric substrate undergoes co-polymerization in the presence of a sufficient amount of the target enzyme (e.g., myeloperoxidase) with one or more macromolecules, which are substantially free of monomeric substrate subunits, to form a co-polymer having a plurality of monomeric substrate subunits and one or more macromolecules, in which at least one of the monomeric substrate subunits can be cross-linked with another monomer subunit or the macromolecule.

The polymer or co-polymer can have two or more monomeric substrate subunits that are connected to one another by one or more chemical bonds between each of the polymerizing moieties.

The monomeric substrate can have 2, 3, or 4 polymerizing moieties.

In some embodiments, the monomeric substrate has the formula, $X—[Y(Z)_m]_n$, in which X is a chelator moiety; each Y is a linker moiety; and each Z is a polymerizing moiety; m can be 1, 2, or 3; and n can be 2, 3, 4, 5, or 6. m can be 1. n can be 2. m can be 1, and n can be 2.

In some embodiments, each Z, independently, can have formula (II):

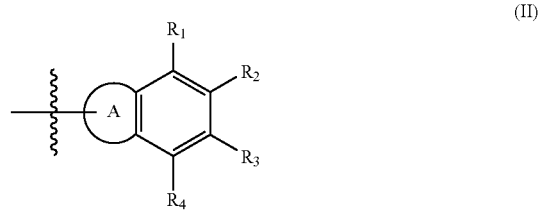

in which A is a monocyclic, bicyclic, tricyclic, or polycyclic moiety, optionally having one or more double bonds and/or optionally inserted with one or more heteroatoms; and
each of $R_1$, $R_2$, $R_3$, and $R_4$ is selected from the group consisting of hydrogen, hydroxy, $C_1$-$C_6$ alkoxy, $C_6$-$C_{18}$ (e.g., $C_6$-$C_{14}$, $C_6$-$C_{10}$, phenyl) aryloxy, amino, $C_1$-$C_6$ alkylamino, $C_1$-$C_6$ dialkylamino, and $C_1$-$C_6$ alkylcarboxamido; provided that at least one of $R_1$, $R_2$, $R_3$, and $R_4$ is hydroxy.

In some embodiments, each Z, independently, can have formula (III):

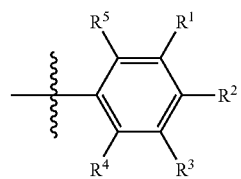

in which $R^1$, $R^2$, $R^3$, $R^4$ and $R^5$ is selected independently from the group consisting of H; $R^6$, $OR^6$ wherein $R^6$ can be $C_1$-$C_6$ unsubstituted alkyl; $NHC(O)R^6$; OH; or $NR^7R^8$, wherein $R^7$ and $R^8$ are H or $R^6$; provided that at least one of $R^1$, $R^2$, $R^3$, $R^4$ and $R^5$ is OH.

$R^1$, $R^2$, $R^3$, $R^4$ or $R^5$ is at an ortho position relative to the OH substituent, and can be selected from the group consisting of OH and $OCH_3$.

$R^1$, $R^2$, $R^3$, $R^4$ or $R^5$ is at a meta position relative to the OH substituent, and can be selected from the group consisting of $NHC(O)R^6$ and $NR^7R^8$.

The Z moiety of formula (III) is a moiety that can be accommodated by the catalytic center of the enzyme.

In a further aspect, the invention also features methods of making compounds described herein (e.g., monomeric substrates). Alternatively, the methods include taking any one of the intermediate compounds described herein and reacting them with one or more chemical reagents in one or more steps to produce a compound described herein.

In one aspect, the invention features a packaged product. The packaged product includes a container, one or more of the compounds described herein (e.g., a monomeric substrate) in the container, and a legend (e.g., a label or an insert) associated with the container and indicating administration of the compound for imaging a target enzyme, (e.g., an oxidoreductase, e.g., a myeloperoxidase).

In another aspect, the invention features compounds (e.g., monomeric substrates) including a pharmaceutically acceptable salt thereof, of any of the formulae delineated herein, or compositions including a compound (e.g., a monomeric substrate or a pharmaceutically acceptable salt thereof) of any of the formulae delineated herein. In some embodiments, the compounds or compositions further include a pharmaceutically acceptable adjuvant, carrier, or diluent and/or a therapeutic agent.

In a further aspect, this invention features methods for screening agents (e.g., therapeutic agents) that interact with (e.g., inhibit) a target enzyme (e.g., a myeloperoxidase). The methods include combining an agent, a target enzyme, and a monomeric substrate, and measuring the relaxivity or shortening of relaxation times or magnetic resonance signal intensity of the sample. In some embodiments, the formation of paramagnetic or superparamagnetic substances having a molecular weight greater than that of the substrate can indicate that the agent does not interact (e.g., inhibit) the target enzyme. Conversely, a lack of formation of paramagnetic or superparamagnetic substances having a molecular weight greater than that of the substrate indicates that the agent does interact with the target enzyme (and may do so in a manner that correlates with causing a desired therapeutic effect (e.g., treats or prevents a disease) in a subject (e.g., a mammal)).

Monomeric substrates as well as compositions that include the monomeric substrates described herein, with or without a chelated metal atom or ion, are also part of the invention.

Embodiments can include one or more of the following features.

A is:

wherein (as shown herein, the wavy line intersecting the bond on the left represents the connection to X—Y—; the wavy lines intersecting the two bonds on the right represent the connection to the aromatic ring)

B is $CR^aR^b$ or $NR^c$;

$R^d$ is hydrogen or $R^d$ together with one of $R^a$, $R^b$ or $R^c$ is a bond;

G is $NR^e$, O, or S;

each of $R^a$ and $R^b$ is, independently, hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkylamino, $C_1$-$C_4$ dialkylamino, mercapto, $C_1$-$C_6$ thioalkoxy, $SO_3H$, sulfate, or phosphate; or one of $R^a$ and $R^b$ is hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkylamino, $C_1$-$C_4$ dialkylamino, mercapto, $C_1$-$C_6$ thioalkoxy, $SO_3H$, sulfate, or phosphate, and the other together with $R^d$ is a bond;

$R^c$ is hydrogen or $C_1$-$C_6$ alkyl; or $R^c$ together with $R^d$ is a bond; and $R^e$ is hydrogen or $C_1$-$C_6$ alkyl.

G is $NR^e$. $R^e$ is hydrogen. B is $CR^aR^b$. $R^a$ is hydrogen and $R^b$ together with $R^d$ is a bond.

A is:

wherein (as shown herein the wavy line intersecting the bond on the left represents the connection to X—Y—; the wavy lines intersecting the two bonds on the right represent the connection to the aromatic ring)

D is $CR^gR^h$ or $NR^j$;

$R^f$ is hydrogen or $R^f$ together with one of $R^g$, $R^h$ or $R^j$ is a bond;

G is $NR^e$, O, or S;

$R^e$ is hydrogen or $C_1$-$C_6$ alkyl; or $R^e$ together with one of $R^g$ or $R^h$ is a bond;

each of $R^g$ and $R^h$ is, independently, hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkylamino, $C_1$-$C_4$ dialkylamino, mercapto, $C_1$-$C_6$ thioalkoxy, $SO_3H$, sulfate, or phosphate; or one of $R^g$ and $R^h$ is hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkylamino, $C_1$-$C_4$ dialkylamino, mercapto, $C_1$-$C_6$ thioalkoxy, $SO_3H$, sulfate, or phosphate, and the other together with $R^e$ or $R^f$ can be a bond; and $R^j$ is hydrogen or $C_1$-$C_6$ alkyl; or $R^j$ together with $R^e$ or $R^f$ is a bond.

G is $NR^e$. $R^e$ is hydrogen. D is $CR^gR^h$. $R^g$ is hydrogen and $R^h$ together with $R^f$ is a bond.

$R^1$, $R^2$, $R^3$, or $R^4$ is at an ortho position relative to the OH substituent, and is selected from the group consisting of OH, $OCH_3$, or $C_6$-$C_{18}$ aryloxy (e.g., OH, $OCH_3$).

$R^1$, $R^2$, $R^3$, or $R^4$ is at a meta position relative to the OH substituent, and is selected from the group consisting of amino, $C_1$-$C_6$ alkylamino, $C_1$-$C_6$ dialkylamino, and $C_1$-$C_6$ alkylcarboxamido.

One of $R^2$ and $R^3$ is hydroxy and the other is hydrogen.

$R^1$ and $R^4$ are both hydrogen.

$R^4$ is hydroxy, $C_1$-$C_6$ alkoxy, or $C_6$-$C_{18}$ aryloxy.

A is:

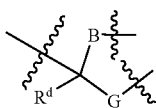

in which B is $CR^aR^b$; $R^a$ is hydrogen; $R^d$ together with $R^b$ is a bond; G is $NR^e$; and $R^e$ is hydrogen.

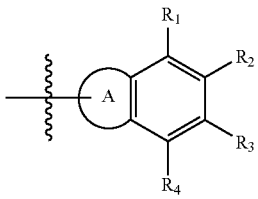

can be a moiety that can be accommodated by the catalytic center of the enzyme.

Y can include a structure selected from the group consisting of: an amino acid, an oligopeptide comprising 2-6 amino acid residues, a nucleotide, an oligonucleotide comprising 2-6 nucleotide residues, a $C_3$-$C_{12}$ alkyl group, a polyethyleneimine, a saccharide, an oligosaccharide, a medium chain fatty acid, a polyamidoamine, a polyacrylic acid, and a polyalcohol.

Y can include an amino acid or oligopeptide containing 2-6 amino acid residues. The oligopeptide can include a glycine residue.

X can include a structure selected from the group consisting of: 1,4,7,10-tetraazacyclodo-decane-N,N',N'',N'''-tetraacetic acid; 1,4,7,10-tetraaza-cyclododecane-N,N',N''-triacetic acid; 1,4,7-tris(carboxymethyl)-10-(2'-hydroxypropyl)-1,4,7,10-tetraazocyclodecane; 1,4,7-triazacyclonane-N,N',N''-triacetic acid; 1,4,8,11-tetraazacyclotetra-decane-N,N',N'',N'''-tetraacetic acid; diethylenetriamine-pentaacetic acid (DTPA); ethylenedicysteine; bis(aminoethanethiol)carboxylic acid; triethylenetetraamine-hexaacetic acid; ethylenediamine-tetraacetic acid (EDTA); 1,2-diaminocyclohexane-N,N,N',N'-tetraacetic acid; N-(hydroxy-ethyl)ethylenediaminetriacetic acid; nitrilotriacetic acid; and ethylene-bis(oxyethylene-nitrilo) tetraacetic acid.

The chelator moiety can include a polycarboxylic macrocycle, an open polycarboxylic chelate (e.g., DTPA; ethylenedicysteine; bis(aminoethanethiol)carboxylic acid; triethylenetetraamine-hexaacetic acid; EDTA; N-(hydroxy-ethyl) ethylenediaminetriacetic acid; nitrilotriacetic acid; and ethylene-bis(oxyethylene-nitrilo)tetraacetic acid; e.g., DTPA).

The monomeric substrate can further include a paramagnetic or superparamagnetic metal atom or ion; or a moiety containing a radionuclide.

The monomeric substrate can further include a paramagnetic or superparamagnetic metal atom or ion (e.g., a bound paramagnetic or superparamagnetic metal atom or ion). The paramagnetic or superparamagnetic metal atom or ion can be a transition metal atom or ion. The paramagnetic or superparamagnetic metal atom or ion can be a lanthanide atom or ion. The metal ion can be selected from the group consisting of an iron ion, a dysprosium ion, a europium ion and a manganese ion. The metal ion can be a gadolinium ion.

The monomeric substrate can further include a moiety containing a radionuclide (e.g., a bound radionuclide, e.g., $^{67}Ga$).

The clearance rate of the polymer or co-polymer can be different than the clearance rate of the monomeric substrate. For example, the clearance rate of the polymer or co-polymer can be slower relative to the clearance rate of the monomeric substrate (e.g., the clearance rate of the polymer or co-polymer can be about 3 times slower than the clearance rate of the monomeric substrate; the clearance rate of the polymer or co-polymer can be about 3 times slower than the clearance rate of the monomeric substrate).

The co-polymer can further include one or more chemical bonds between a polymerizing moiety and a macromolecule.

When the substrate is present with (e.g., a sufficient amount of) a myeloperoxidase in the sample or target tissue, the substrate undergoes polymerization to form a paramagnetic or superparamagnetic (or radioactive) polymer or copolymer comprising monomeric substrate repeat subunits (e.g., a paramagnetic or superparamagnetic polymer).

When the substrate is present with (e.g., a sufficient amount of) a myeloperoxidase in the sample or target tissue, one or more substrates bind to a macromolecule (also present in the sample) that is substantially free of monomeric substrate repeat subunits.

When the substrate is present with (e.g., a sufficient amount of) a myeloperoxidase in the sample or target tissue, the substrate undergoes polymerization to form a paramagnetic or superparamagnetic polymer or copolymer comprising monomeric substrate repeat subunits, and one or more substrates bind to a macromolecule (also present in the sample or target tissue) that is substantially free of monomeric substrate repeat subunits.

The chemically modified substrates (a) can polymerize to form a paramagnetic or superparamagnetic polymer or copolymer including monomeric substrate repeat subunits and/or (b) can bind to a macromolecule (also present in the sample or target tissue) that is substantially free of monomeric substrate repeat subunits.

The methods can include allowing sufficient time for the substrate to accumulate in a target tissue in the subject and for the substrate to undergo polymerization to form a paramagnetic or superparamagnetic polymer or copolymer including monomeric substrate repeat subunits and/or for one or more substrates to bind to a macromolecule in the sample that is substantially free of monomeric substrate repeat subunits; the polymerization or binding of the substrate being mediated by (e.g., catalyzed by) myeloperoxidase in the target tissue.

The target enzyme can be a oxidoreductase. The oxidoreductase can be a myeloperoxidase. The myeloperoxidase can be a human myeloperoxidase. The human myeloperoxidase can be secreted by human neutrophils and/or monocytes/macrophages. The human neutrophils and/or monocytes/macrophages can be associated with a human atherosclerotic plaque. The human atherosclerotic plaque can be a vulnerable plaque (e.g., a ruptured vulnerable plaque). The sample can be in vitro or in vivo. The sample can be tissue. The tissue can include human or animal neovasculature (e.g., diseased or developmental human or animal tissue).

The polymerization can be catalyzed by a target enzyme that is present in an extracellular matrix or bound to the surfaces of cells of a target tissue. The target enzyme can be covalently linked to a targeting moiety, the targeting moiety being bound to a target molecule on the surface of a cell of the target tissue. The co-polymer can include one or more macromolecules present in an extracellular matrix of the target tissue or to the surface of a cell of the target tissue.

The macromolecules can be substantially free of monomeric substrate subunits. The macromolecules can be selected from the group consisting of, proteins, oligosaccharides, and polynucleotides present in the extracellular matrix or bound to the surface of a cell of the target tissue.

The target enzyme can be selected from the group consisting of an oxidoreductase, a monophenol oxidase, monophenol monooxygenase, and a catechol oxidase. The target enzyme can be selected from the group consisting of tyrosinase, tyrosinase-related protein, lipase, DNA polymerase, thermostable DNA polymerase, RNA polymerase, RNA-dependent DNA polymerase, reverse transcriptase, terminal nucleotide transferase, and polynucleotide phosphorylase. The target enzyme can be a monophenol oxidase or catechol oxidase. The oxidoreductase can be selected from the group consisting of a peroxidase and a laccase. The oxidoreductase is a peroxidase is selected from the group consisting of lactoperoxidase and horseradish peroxidase.

The targeting moiety can be selected from the group consisting of a primary antibody, a secondary antibody, a cell adhesion molecule, a cytokine, a cell surface receptor molecule, or a fragment thereof that recognizes a preselected binding partner. The enzyme can be a peroxidase and the targeting moiety is selected from the group consisting of a primary antibody and a secondary antibody.

Representative monomeric substrates include:

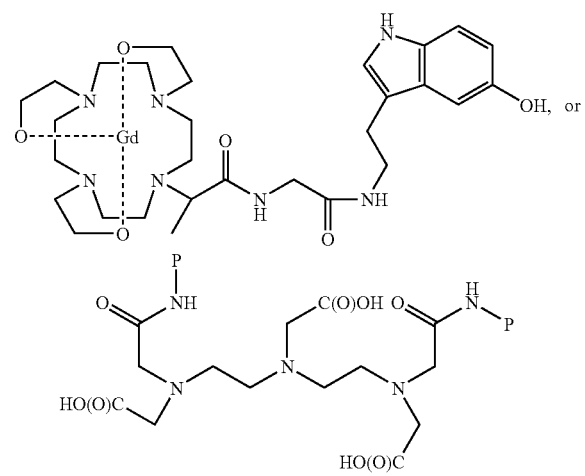

in which P can be:

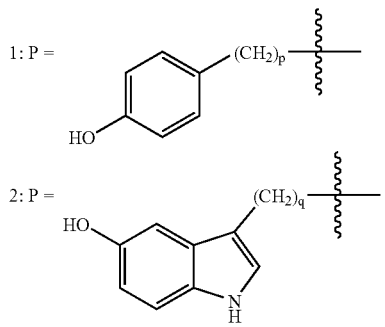

(p is 1-10, and is preferably 2; q is 1-10, and is preferably 1 or 2).

As used herein, "an equivalent amount of unpolymerized substrate" means the number of monomeric substrate molecules represented by a polymer having a particular molecular size or mass.

As used herein, the term "vulnerable plaque" refers to an unstable plaque that is prone to rupture.

As used herein, the term "unit of myeloperoxidase activity" (U) refers to the unit of myeloperoxidase activity as described in Klebanoff, et al., *Methods Enzymol.* 1984, 105, 399-403.

The term "mammal" includes mice, rats, cows, sheep, pigs, rabbits, goats, and horses, monkeys, dogs, cats, and humans.

"SPECT" (e.g., SPECT/CT) refers to single photon emission commuted tomography/computer-assisted tomography hybrid instrument. (X-SPECT, Gamma Medica).

The term "halo" or "halogen" refers to any radical of fluorine, chlorine, bromine, or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms. The term "haloalkyl" refers to an alkyl in which one or more hydrogen atoms are replaced by halo, and includes alkyl moieties in which all hydrogens have been replaced by halo (e.g., perfluoroalkyl, such as $CF_3$). The term "aralkyl" refers to an alkyl moiety in which an alkyl hydrogen atom is replaced by an aryl group. Aralkyls include groups in which more than one hydrogen atom on an alkyl moiety has been replaced by an aryl group. Examples of "aralkyls" include benzyl, 2-phenylethyl, 3-phenylpropyl, 9-fluorenyl, benzhydryl, and trityl groups.

The term "alkenyl" refers to a straight or branched hydrocarbon chain containing 2-12 carbon atoms and having one or more double bonds. Alkenyl groups can include, e.g., allyl, propenyl, 2-butenyl, 3-hexenyl, and 3-octenyl groups. One of the double bond carbons can optionally be the point of attachment of an alkenyl substituent. The term "alkynyl" refers to a straight or branched hydrocarbon chain containing 2-12 carbon atoms and characterized in having one or more triple bonds. Alkynyl groups can include, e.g., ethynyl, propargyl, and 3-hexynyl. One of the triple bond carbons can optionally be the point of attachment of an alkynyl substituent.

Alkylene, alkenylene, alkynylene, and cycloalkylene refer to divalent alkyl, alkenyl, alkynyl, and cycloalkyl moieties, respectively (e.g., —$CH_2$—, —CH═CH—, —C≡C—, and -ring-, respectively). Any atom can be substituted.

The terms "alkylamino" and "dialkylamino" refer to —NH(alkyl) and —NH(alkyl)$_2$ radicals respectively. The term "alkoxy" refers to an —O-alkyl radical. The term "mercapto" refers to an SH radical. The term "thioalkoxy" refers to an —S-alkyl radical. The term aryloxy refers to an —O-aryl radical. The term thioaryloxy refers to an —S-aryl radical.

The term "aryl" refers to an aromatic monocyclic, bicyclic, or tricyclic hydrocarbon ring system, wherein any ring atom can be substituted, e.g., by one or more substituents. Aryl groups can contain fused rings. Fused rings are rings that share a common carbon atom. Aryl moieties include, e.g., phenyl, naphthyl, anthracenyl, and pyrenyl.

The term "cycloalkyl" refers to saturated cyclic, bicyclic, tricyclic, or polycyclic hydrocarbon groups having 3 to 12 carbons. Any ring atom can be substituted, e.g., by one or more substituents. Cycloalkyl groups can contain fused rings. Fused rings are rings that share a common carbon atom. Cycloalkyl moieties can include, e.g., cyclopropyl, cyclohexyl, methylcyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, and wherein the heteroatom is selected from O, N, or S (e.g., carbon atoms and 1-3, 1-6, or 1-9 heteroatoms of N, O, or S if monocyclic, bicyclic, or tricyclic, respectively). The heteroatom can optionally be the point of attachment of the heterocyclyl substituent. Any ring atom can be substituted, e.g., by one or more substituents. The heterocyclyl groups can contain fused rings. Fused rings are rings that share a common carbon atom. Heterocyclyl groups can include, e.g., tetrahydrofuranyl, tetrahydropyranyl, piperidinyl, morpholino, pyrrolinyl, pyrimidinyl, quinolinyl, and pyrrolidinyl.

The term "cycloalkenyl" refers to unsaturated, nonaromatic, cyclic, bicyclic, tricyclic, or polycyclic hydrocarbon groups having 3 to 12 carbons, e.g., 5 to 8 carbons. The unsaturated carbon can optionally be the point of attachment of the cycloalkenyl substituent. Any ring atom can be substituted e.g., by one or more substituents. The cycloalkenyl groups can contain fused rings. Fused rings are rings that share a common carbon atom. Cycloalkenyl moieties can include, e.g., cyclohexenyl, cyclohexadienyl, norbornenyl, or cyclooctatetraenyl.

The term "heterocycloalkenyl" refers to a unsaturated, nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The unsaturated carbon or the heteroatom can optionally be the point of attachment of the heterocycloalkenyl substituent. Any ring atom can be substituted, e.g., by one or more substituents. The heterocycloalkenyl groups can contain fused rings. Fused rings are rings that share a common carbon atom. Heterocycloalkenyl groups can include, e.g., tetrahydropyridyl and dihydropyranyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted, e.g., by one or more substituents. Heteroaryl groups can contain fused rings. Fused rings are rings that share a common carbon atom. Heteroaryl groups include pyridyl, thienyl, furanyl, imidazolyl, and pyrrolyl.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which can be further substituted, e.g., by one or more substituents.

The terms "aminocarbonyl" and "alkoxycarbonyl" refer to the radicals —C(O)NH$_2$ and —C(O)O(alkyl), respectively.

The term "alkylcarboxamido" refers to a —NHC(O)(alkyl) radical, wherein the nitrogen atom is the point of attachment of the radical to another moiety.

The term "substituents" refers to a group "substituted" on, e.g., an alkyl, cycloalkyl, alkenyl, alkynyl, heterocyclyl, heterocycloalkenyl, cycloalkenyl, aryl, or heteroaryl group at any atom of that group. Any atom can be substituted, e.g., by one or more substituents. Suitable substituents can include, e.g., alkyl (e.g., $C_1$, $C_2$, $C_3$, $C_4$, $C_5$, $C_6$, $C_7$, $C_8$, $C_9$, $C_{10}$, $C_{11}$, $C_{12}$ straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, $SO_3H$, sulfate, phosphate, methylenedioxy (—O—CH$_2$—O— wherein oxygens are attached to vicinal atoms, e.g., carbon atoms, of a moiety), ethylenedioxy, oxo, thioxo (e.g., C=S), imino (alkyl, aryl, aralkyl), S(O)$_n$alkyl (where n is 0-2), S(O)$_n$aryl (where n is 0-2), S(O)$_n$heteroaryl (where n is 0-2), S(O)$_n$heterocyclyl (where n is 0-2), amino (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

For ease of exposition, it is understood that any recitation of ranges (e.g., $C_1$-$C_{20}$) or subranges of a particular range (e.g., $C_1$-$C_4$, $C_2$-$C_6$) for any of the variables described herein ($R^a$, $L_1$, etc.) expressly includes each of the individual values that fall within the recited range, including the upper and lower limits of the recited range. For example, the range $C_1$-$C_4$ alkyl is understood to mean (e.g., $C_1$, $C_2$, $C_3$, or $C_4$) alkyl.

Embodiments can have one or more of the following advantages.

In some embodiments, polymerization of the monomeric substrates in the presence of myeloperoxidase can proceed with fast kinetics and result in a large increase in relaxivity, thereby increasing the likehood that imaging can be performed under clinical conditions, e.g., using a 1.5 Tesla (T) magnetic resonance imaging (MRI) scanner.

In some embodiments, polymerization or binding of the monomeric substrates in the presence of an enzyme, e.g., a target enzyme, can result in the formation of large complexes (e.g., oligomers, polymers, substrate-macromolecule complexes) having high atomic relaxivities.

While not wishing to be bound by theory, it is believed that the formation of such complexes will result in a decrease in local proton relaxation rates (i.e., shortening of T1 and T2 relaxation times for water molecules that are proximal to the site of the enzymatic activity). It is believed that the formation of such complexes can allow the monomeric substrates to be administered in relatively low and non-toxic doses.

In some embodiments, polymerization of the monomeric substrates in the presence of an enzyme, e.g., a target enzyme, can result in the formation of rigid complexes (e.g., oligomers, polymers) having a high degree of cross linking.

It is believed that having at least two polymerizing moieties attached to each chelator moiety increases the effective local concentration of the erstwhile radical intermediates, thereby increasing the likelihood of cross linking a monomeric substrate subunit on one chain with either another monomeric substrate subunit or macromolecule on a separately growing chain.

In some embodiments, polymerization of the monomeric substrates in the presence of an enzyme, e.g., a target enzyme, results in the formation of complexes (e.g., oligomers, polymers) having an in vivo clearance rate (i.e., a low rate of removal of the complex from the body) that is lower than that of the monomeric substrate. In some embodiments, the clearance rate of the complex is substantially slower than that of the monomeric substrate itself.

It is believed that the formation of such complexes provides high imaging signals having enhanced signal to noise ratios because the complex can be imaged after the monomeric substrate has been cleared.

In some embodiments, polymerization of the monomeric substrates in the presence of an enzyme, e.g., a target enzyme, results in the formation of complexes (e.g., oligomers, polymers) having relatively low vascular permeabilities.

In some embodiments, the monomeric substrates are highly sensitive to MPO activity increasing the likelihood that these agents can image in vivo sites of MPO activity to reflect inflammation, and be used in magnetic resonance and scintigraphic imaging.

In some embodiments, polymerization of the monomeric substrates in the presence of an enzyme, e.g., a target enzyme, proceeds with fast kinetics and with a high efficiency and result in a large increase in relaxivity, thereby increasing the likehood that imaging can be performed under clinical conditions, e.g., using a 1.5 Tesla (T) magnetic resonance imaging (MRI) scanner.

In some embodiments, the reducing potential of monomeric substrates is sufficiently high so as to out-compete chloride anion, one of the natural substrates for myeloperoxidase.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features and advantages of the invention will be apparent from the description and from the claims.

DESCRIPTION OF DRAWINGS

FIG. 1A corresponds to tyramide-DOTA(Gd); FIG. 1B corresponds to hydroxytyramide-DOTA(Gd); and FIG. 1C corresponds to 5-hydroxytryptamide-DOTA(Gd).

FIG. 2 is a graphical representation of the dependence of the myeloperoxidase (MPO) conversion on the concentration of hydrogen peroxide as measured by T1 and T2 shortening at 0.47 T. The standard deviation of each point is less than or equal to 1 millisecond (ms).

FIG. 6A is a spin echo T1 weighted MR image at 1.5 T of a 100 µM. solution of the substrate 5-HT-DOTA(Gd). TR=350 and TE=11.

FIGS. 6B, 6C, 6D, 6E, and 6F are spin echo T1 weighted MR images at 1.5 T showing the effect of the addition of 650 U MPO, 1300 U MPO, 2000, 1400 U HRP, and 650 U MPO without $H_2O_2$ (control), respectively, to the substrate solution shown in FIG. 6A. TR=350 and TE=11.

FIG. 7A is a T2 weighted MR image at 1.5 T of a 100 µM. solution of the substrate 5-HT-DOTA(Gd). TR=350 and TE=11. A fast spin echo (FSE) sequence was employed, with TR=5000 ms, TE=100 ms, and echo train length (ETL)=12.

FIGS. 7B, 7C, 7D, 7E, and 7F are T2 weighted MR image at 1.5 T showing the effect of the addition of 650 U MPO, 1300 U MPO, 2000, 1400 U HRP, and 650 U MPO without $H_2O_2$ (control), respectively, to the substrate solution shown in FIG. 7A. A fast spin echo (FSE) sequence was employed, with TR=5000 ms, TE=100 ms, and echo train length (ETL)=12.

FIG. 16A is a T1 weighted image of an MPO mouse model after injection with Magnevist control.

FIGS. 25A, 25B, 25C, and 25D are magnetic resonance images obtained at 1.5 T in the Matrigel/MPO mouse experiment. The right side of the image contains human MPO embedded in Matrigel along with a monomeric substrate. The left side contains only the Matrigel and the monomeric substrate (i.e., no MPO present). The monomeric substrates employed in the images shown in FIGS. 25A, 25B, 25C, and 25D are DTPA(Gd), bis-tyr-DTPA(Gd), 5-HT-DOTA(Gd), and bis-5-HT-DTPA(Gd), respectively. Note that there is significantly increased enhancement in the right side of the mice injected with MPO-sensitive agents (c) 5-HT-DOTA(Gd) and (d) bis-5-HT-DTPA, but not with (a) GdDTPA or (b) bis-tyr-DTPA(Gd), which has a similar structure to bis-5-HT-DTPA (Gd) but based on tyramine instead of 5-HT.

FIGS. 26A and 26B are magnetic resonance images obtained at 4.7 T for mice with LPS induced myositis. The images shown in FIG. 26A were obtained using DTPA(Gd) as a control, while the images shown in FIG. 26B were obtained with 5-HT-DOTA(Gd). Note that by 50 minutes there is significant wash-out of the enhancement in the top panel of images (similar results (not shown) were obtained for dopamine-DOTA(Gd), an agent similar in structure to 5-HT-DOTA (Gd). On the other hand, there was still significant enhancement 50 minutes after injection of (b) 5-HT-DOTA(Gd) (similar results (not shown) were obtained for bis-5-HT-DTPA(Gd)).

FIG. 26C is a relative CNR time curve corresponding to the magnetic resonance images shown in FIGS. 26A and 26B and referred to in the figure captions of FIGS. 26A and 26B.

FIGS. 26D and 26E are immunohistochemistry stains of sites with and without LPS, respectively. The site with embedded LPS has recruited a large number of cells that stained positive for MPO, while the site with only Matrigel but without LPS contained very few cells and did not stain positive for MPO.

FIG. 27A is a fused SPECT/CT image demonstrating significant increased uptake of the $^{111}$In-chelated monomeric substrate on the right side containing MPO 3 hours after the injection of 111In-bis-5-HT-DTPA.

FIG. 27B is a graphical representation of biodistribution results of the dosage of the $^{111}$In-chelated monomeric substrate, indicating that most of the agents are distributed in the spleen, kidneys, bowel, and liver.

Like reference symbols in the various drawings indicate like elements.

DETAILED DESCRIPTION

Figure 1A:
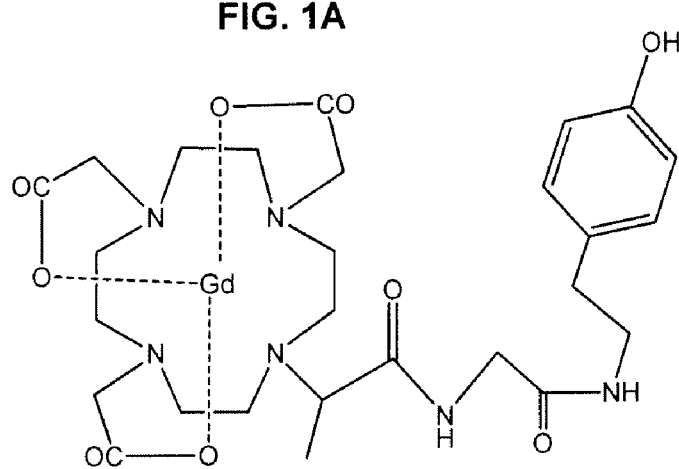
FIGS. 1A, 1B, and 1C are diagrams showing the electron-donating paramagnetic substrates for peroxidase-mediated reactions of $H_2O_2$ reduction.

This invention relates to compounds (e.g., monomeric substrates) and compositions thereof as well as methods of making and using the compounds and compositions for noninvasive, magnetic resonance imaging of enzymatic activity (e.g., oxidoreductase activity; e.g., myeloperoxidase activity, e.g., magnetic resonance imaging of myeloperoxidase activity in arteries where the myeloperoxidase activity indicates the presence of a vulnerable plaque).

The methods and compositions feature compounds (e.g., monomeric substrates (MS)), which are capable of chelating a metal atom or ion (e.g., gadolinium (Gd) or gallium (Ga)) and, upon interaction with an enzyme (e.g., a target enzyme), are capable of being chemically modified (e.g., converted into free radical intermediates) and subsequently undergoing one or more chemical reactions that result in the formation of (MS)-containing product(s) having a higher molecular weight than that of the starting monomeric substrate itself (e.g., 2, 3, 4, 5, 6, 7, 8, 9, 10, 20, 50, 100, 1,000, 5,000, 10,000, 50,000, 100,000, 300,000, 500,000, or 1,000,000 times higher than that of the substrate itself).

Substrate monomers can undergo, for example (and without limitation), one or more or more of the following processes:

(a) enzyme-dependent polymerization or co-polymerization of the monomeric substrate, resulting in the formation of polymeric products having monomeric substrate repeat subunits (e.g., polymers or co-polymers, having structures such as -MS-[MS]-MS- or MS-[MS]-MS-, in which "MS" is a monomer substrate subunit); such oligomers or polymers can also be crosslinked); and/or (b) enzyme-mediated binding (e.g., covalent binding) of the monomeric substrate (or oligomers or polymers thereof) to high molecular weight molecules (e.g., macromolecules) other than the oligomerized or polymerized intermediates or products formed in process (a) (i.e., a macromolecule that is substantially free of monomeric substrate repeat subunits, e.g., a macromolecule present in biological systems, such as a protein) to form addition products (e.g., complexes) resulting from the interaction and attachment of the substrate (or oligomers or polymers thereof) to the high molecular weight chemical compounds; for example, one or more monomeric substrates can each bind to separate sites on a macromolecule or polymerized substrates can bind to a macromolecule (e.g., a protein, (A-A-A-A-A)) to form products having structures, for example, such as A(MS)-A-A-A(MS)-A or MS-[MS]-MS-A-A-A-A-A.

The basis of some of the compounds, methods, and compositions described herein is an enhancement of the effect on local proton relaxation rates (decrease in T1 and T2 relaxation times) exerted by a chelated (super)paramagnetic metal or metal oxide. This enhancement can occur when a monomeric substrate containing a chelated (super)paramagnetic metal or metal oxide is converted to (super)paramagnetic substance(s) or product(s) that are larger in size and have a higher molecular weight than that of the substrate (e.g., via enzyme-mediated (e.g., catalyzed) polymerization of the monomeric substrate or binding of one or more monomeric substrates to a macromolecule (e.g., a protein). The decreased relaxation times (increased relaxivity) associated with the polymerized or bound products, relative to an equivalent amount of unchanged (e.g., unpolymerized or unbound) substrate, translates into an amplified MRI signal at the site of enzymatic activity.

While not intending to be bound by theory of the invention's mechanism, the inventors believe the increased relaxivity occurs because the polymerized product has an increased rotational correlation time ($\tau_r$), relative to that of the monomeric substrate.

In some embodiments, the methods and compositions described herein can be used for noninvasive, magnetic resonance imaging of myeloperoxidase. While not wishing to be bound by theory, it is believed that myeloperoxidase contributes to the progression of atherosclerotic plaque from stable to vulnerable. By using, for example, paramagnetic electron donor compounds that rapidly oxidize and polymerize in the presence of myeloperoxidase, with resulting change in signal characteristics, the presence of myeloperoxidase in a lesion can be detected to report on the state of the atherosclerotic plaque.

Monomeric Substrates

In general, monomeric substrates include (i) a chelator moiety for chelating a metal atom or ion (as such, a chelator moiety can further include a chelated metal atom or ion; and (ii) one or more (e.g., 1, 2, 3, 4, 5, 6, 7, 8, 9, or 10) polymerizing moieties, which upon interaction with an enzyme (e.g., a target enzyme), can be chemically modified. Monomeric substrates can also include (iii) one or more linker moieties to connect the chelator moiety to the polymerizing moiety(ies).

Each of the three structural moieties (i.e., the chelator moiety, each of the polymerizing moieties, and each of the linker moieties) performs a separate function. The chelator moiety binds to or chelates the paramagnetic or superparamagnetic metal atom or metal oxide (e.g., transition metal atom or ion or lanthanide atom or ion, e.g., iron ion, a dysprosium ion, a europium ion, and a manganese ion, a gadolinium ion); or a radionuclide or a moiety that includes a radionuclide (e.g., 111In, 99mTc, 94mTc, 67Ga, or 68Ga). In general, the polymerizing moiety renders the monomeric substrate chemically modifiable (e.g., polymerizable or capable of binding to a macromolecule) when the monomeric substrate interacts with a target enzyme. As such, the polymerizing moiety typically serves as the site of reaction when the monomeric substrate undergoes the enzyme-mediated polymerization, co-polymerization, or binding processes as described herein. In some embodiments, the polymerizing moieties serve as electron donors that participate in free radical bond forming reactions (e.g., polymerization reactions) catalyzed by the target enzyme. The linker moiety can provide a chemical bond between the chelator moiety and the polymerizing moiety, so for example when the polymerizing moiety undergoes polymerization, the chelating moiety, with its bound paramagnetic, superparamagnetic, or radioactive label, is polymerized concomitantly.

In some embodiments, monomeric substrates include a chelator moiety (e.g., a polycarboxylic macrocycle or an open polycarboxylic chelate), a linker moiety, and a single polymerizing moiety (see, e.g., formula (I)). In other embodiments, monomeric substrates include a chelator moiety (e.g., a polycarboxylic macrocycle or an open polycarboxylic chelate) and at least two polymerizing moieties, in which each polymerizing moiety is, independently of one another, attached directly, or indirectly with a linker moiety, to the chelator moiety. In certain embodiments, monomeric substrates can further include a bound paramagnetic or superparamagnetic metal atom or metal oxide. In other embodiments, monomeric substrates can further include a bound radionuclide.

Chelator Moieties

Various chelator moieties are known, and can be incorporated into a monomeric substrate useful in the invention, without undue experimentation. In addition, novel chelating moieties may be discovered in the future, and can be used in the invention. In some embodiments, the chelator moiety does not form a covalent bond with the paramagnetic or superparamagnetic metal or metal oxide; or the radionuclide or the moiety that includes a radionuclide. In certain embodiments, the chelating moiety forms a thermodynamically and kinetically stable, non-covalent coordination complex or ionic complex with, e.g., $Fe^{3+}$, $Gd^{3+}$, $Dy^{3+}$, $Eu^{3+}$, $Mn^{2+}$, or other useful metal or metal oxide; or with (e.g., 111In, 99mTc, 94mTc, 67Ga, or 68Ga).

Numerous chelating moieties suitable for incorporation into a monomeric substrate useful in the invention are known in the art. In some embodiments, the chelator moiety can be a polycarboxylic macrocycle or an open polycarboxylic chelate, e.g., 1,4,7,10-tetraazacyclododecane-N,N',N'',N'''-tetraacetic acid (DOTA); 1,4,7,10-tetraaza-cyclododecane-N,N',N''-triacetic acid; 1,4,7-tris(carboxymethyl)-10-(2'-hydroxypropyl)-1,4,7,10-tetraazocyclodecane; 1,4,7-triazacyclonane-N,N',N''-triacetic acid; 1,4,8,11-tetraazacyclotetra-decane-N,N',N'',N'''-tetraacetic acid; diethylenetriamine-pentaacetic acid (DTPA); triethylenetetraamine-hexaacetic acid; ethylenediamine-tetraacetic acid (EDTA); 1,2-diaminocyclohexane-N,N,N',N'-tetraacetic acid; N-(hydroxyethyl)ethylenediaminetriacetic acid; nitrilotriacetic acid; and ethylene-bis(oxyethylene-nitrilo)tetraacetic acid. In certain embodiments, the chelator moiety can be diethylenetriamine-pentaacetic acid (DTPA).

In some embodiments, the chelator moiety can include one or more —C(O)N(OH)— functional groups (e.g., deferoxamine or desferrioxamine).

Polymerizing Moieties

A polymerizing moiety can be any biocompatible moiety that can undergo enzyme-dependent chemical modification (e.g., activatable in the presence of a target enzyme to undergo the polymerization and/or binding processes described herein). Typically, a polymerizing moiety is a moiety that is capable of undergoing enzyme-dependent polymerization. However, the monomeric substrates described herein need not undergo polymerization exclusively or at all upon interaction with a target enzyme. In some embodiments, some or essentially all of the monomeric substrates contacted with a sample or administered to a subject (e.g., as described in the methods described herein) can bind to a macromolecule instead of undergoing polymerization. In general, when monomeric substrates are converted to the (super)paramagnetic or radioactive higher molecular weight (MS)-containing product(s), such products can form via the enzyme-dependent polymerization and/or non-polymerization (e.g. binding to a macromolecule) processes described herein (a combination of processes can include, e.g., a polymerized or oligomerized monomeric substrate binding to a macromolecule). All such monomeric substrates and methods are within the scope of this invention. The target enzyme and each of polymerizing moieties are selected for functional compatibility, i.e., each of the polymerizing moieties is recognized as a substrate by the target enzyme.

As used herein, "phenolic moiety" means a moiety containing a phenolic ring. As used herein, a "phenolic ring" is a (i) phenyl ring (monocyclic) or (ii) a phenyl ring fused to another carbocyclic or heterocyclic ring (bicyclic or tricyclic ring system), in which at least one of the phenyl ring carbons is substituted with a hydroxyl (OH) group, and the other phenyl ring carbons are optionally substituted, provided that at least one phenyl ring carbon is unsubstituted. A phenolic ring can participate in a free radical polymerization reaction, under certain conditions.

In some embodiments, a polymerizing moiety can have formula (II) (e.g., a phenolic moiety having formula (II-A), in which a phenolic ring is fused to a second cyclic moiety A):

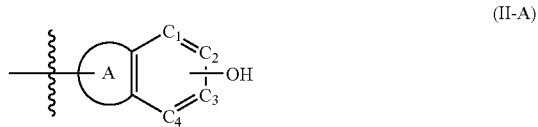

(II-A)

In all embodiments, at least one of $C_1$, $C_2$, $C_3$, and $C_4$ in Formula (II-A) is substituted with a hydroxyl (OH) group, and other ring positions are optionally substituted, e.g., with $C_1$-$C_6$ (e.g., $C_1$, $C_2$, $C_3$, $C_4$, $C_5$, or $C_6$) alkoxy, $C_6$-$C_{18}$ (e.g., $C_6$-$C_{14}$, $C_6$-$C_{10}$, phenyl) aryloxy, amino, $C_1$-$C_6$ alkylamino, $C_1$-$C_6$ dialkylamino, $C_1$-$C_6$ alkylcarboxamido, or another hydroxy group, provided that at least one ring carbon of the phenolic ring is unsubstituted (i.e., substituted with a hydrogen atom). For purposes of clarification, $C_1$, $C_2$, $C_3$, and $C_4$ in Formula (II-A) correspond to the carbons substituted by $R^1$, $R^2$, $R^3$, $R^4$ in formula (II). It is understood that permissible substituents for attachment $C_1$, $C_2$, $C_3$, and $C_4$ in Formula (II-A) can also be permissible substituents for $R^1$, $R^2$, $R^3$, $R^4$, respectively in formula (II).

Numerous structural variations are permissible in the phenolic ring. In certain embodiments, a second hydroxy group or a $C_1$-$C_6$ alkoxy group is located at an ortho position relative to the requisite hydroxy group.

In certain embodiments, an amino group, a $C_1$-$C_6$ alkylamino or dialkylamino group or a $C_1$-$C_6$ carboxamido group (e.g., $C_1$, $C_2$, $C_3$, $C_4$, $C_5$, or $C_6$ carboxamido group) is located at an meta position relative to the requisite hydroxy group.

In some embodiments, one of $C_2$ and $C_3$ is substituted with the hydroxy group and the other can be substituted with a hydrogen atom. In certain embodiments, the remaining carbons $C_1$ and $C_4$ are each substituted with a hydrogen atom.

In some embodiments, $C_4$ is substituted with hydroxy, $C_1$-$C_6$ alkoxy, or $C_6$-$C_{18}$ (e.g., $C_6$-$C_{14}$, $C_6$-$C_{10}$, phenyl) aryloxy.

The second cyclic moiety, A, can be a monocyclic, bicyclic, tricyclic, or polycyclic moiety and can further include one or more double bonds and/or can be optionally inserted with one or more heteroatoms (e.g., nitrogen, oxygen, and sulfur). One of the constituent atoms (e.g., a carbon atom) of the second cyclic moiety serves as the point of attachment for the linker moiety. For purposes of clarification, the second cyclic moiety, A, in formula (II-A) corresponds to the second cyclic moiety, A, in formula (II). It is understood that permissible ring systems for A in formula (II-A) and in the formulae that follow can also be permissible ring systems in formula (II).

In some embodiments, the polymerizing moiety includes a phenolic ring fused to a second cyclic moiety that is monocyclic. Examples of such polymerizing moieties include, without limitation, those having formulas (IV) and (V). Each of atoms B, D,

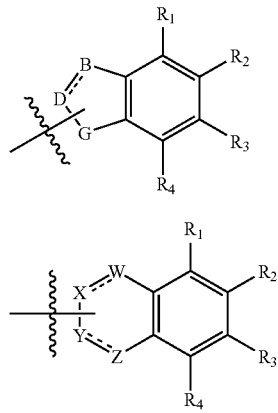

and G in the second cyclic moiety portion of Formula (IV) can be, independently of one another, a carbon atom or a heteroatom, e.g., nitrogen, oxygen, or sulfur. Each of atoms W, X, Y, and Z in the second cyclic moiety portion of formula (V) can be, independently of one another, a carbon atom or a heteroatom, e.g., nitrogen, oxygen, or sulfur. Polymerizing moieties having formulas (IV) and (V) can be partially or fully saturated ring systems.

In some embodiments, the polymerizing moiety can have formula (VI), in which B can be $CR^aR^b$ or $NR^c$; $R^d$ can be hydrogen or $R^d$ together with one of $R^a$, $R^b$, or $R^c$ can be a bond; and G can be $NR^e$, O, or S.

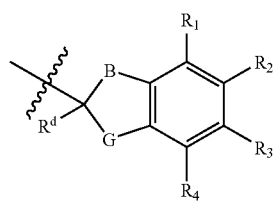

In some embodiments, each of $R^a$ and $R^b$ can be, independently, hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, di($C_1$-$C_4$ alkyl)aminocarbonyl, $C_1$-$C_6$ alkoxycarbonyl, cyano, nitro, amino, $C_1$-$C_4$ alkylamino, di($C_1$-$C_4$ alkyl)amino, mercapto, $C_1$-$C_6$ thioalkoxy, SO$_3$H, sulfate, or phosphate.

In some embodiments, one of $R^a$ and $R^b$ is hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, di($C_1$-$C_4$ alkyl)aminocarbonyl, $C_1$-$C_6$ alkoxycarbonyl, cyano, nitro, amino, $C_1$-$C_4$ alkylamino, di($C_1$-$C_4$ alkyl)amino, mercapto, $C_1$-$C_6$ thioalkoxy, SO$_3$H, sulfate, or phosphate, and the other together with $R^d$ is a bond.

In some embodiments, $R^a$ and $R^b$ can be independently further substituted by one or more substitutents (e.g., hydroxy, $C_1$-$C_6$ alkyl, amino, $C_1$-$C_6$ alkoxy, oxo, halo).

$R^c$ can be hydrogen or $C_1$-$C_6$ alkyl; or $R^c$ together with $R^d$ can be a bond. $R^e$ can be hydrogen or $C_1$-$C_6$ alkyl.

The phenolic ring substituents $R_1$, $R_2$, $R_3$, and $R_4$ can be as described herein in Formula (II-A).

In some embodiments, G can be $NR^e$ (e.g., NH) and B can be $CR^aR^b$, in which $R^a$ is hydrogen and $R^b$ together with $R^d$ is a bond. In some embodiments, one of $R_1$, $R_2$, $R_3$, and $R_4$ is hydroxy, and the other three are hydrogen. In certain embodiments, the polymerizing moiety can have formula (VI-A):

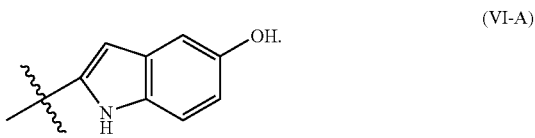

In some embodiments, the polymerizing moiety can have formula (VII), in which D can be $CR^gR^h$ or $NR^j$; $R^f$ can be hydrogen or $R^f$ together with one of $R^g$, $R^h$ or $R^j$ is a bond; G can be $NR^e$, O, or S; and $R^e$ can be hydrogen or $C_1$-$C_6$ alkyl; or $R^e$ together with one of $R^g$ or $R^h$ can a bond.

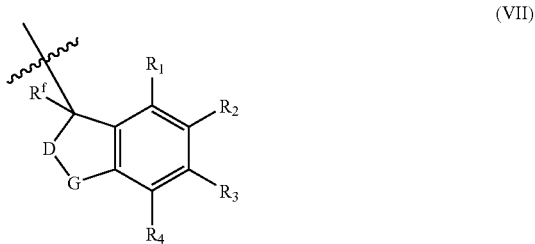

In some embodiments, each of $R^g$ and $R^h$ is, independently, hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, di($C_1$-$C_4$ alkyl)aminocarbonyl, $C_1$-$C_6$ alkoxycarbonyl, cyano, nitro, amino, $C_1$-$C_4$ alkylamino, di($C_1$-$C_4$ alkyl)amino, mercapto, $C_1$-$C_6$ thioalkoxy, SO$_3$H, sulfate, or phosphate.

In some embodiments, one of $R^g$ and $R^h$ is hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, di($C_1$-$C_4$ aminocarbonyl, $C_1$-$C_6$ alkoxycarbonyl, cyano, nitro, amino, $C_1$-$C_4$ alkylamino, di($C_1$-$C_4$ alkyl)amino, mercapto, $C_1$-$C_6$ thioalkoxy, SO$_3$H, sulfate, or phosphate, and the other together with $R^e$ or $R^f$ is a bond.

In some embodiments, $R^g$ and $R^h$ can be independently further substituted by one or more substituents (e.g., hydroxy, $C_1$-$C_6$ alkyl, amino, $C_1$-$C_6$ alkoxy, oxo, halo).

$R^i$ can be hydrogen or $C_1$-$C_6$ alkyl; or $R^i$ together with $R^e$ or $R^f$ is a bond.

The phenolic ring substituents $R_1$, $R_2$, $R_3$, $R_4$ can be as described elsewhere in Formula (II-A).

In some embodiments, G can be $NR^e$ (e.g., NH) and D can be $CR^gR^h$, in which $R^g$ is hydrogen and $R^h$ together with $R^f$ is a bond. In some embodiments, one of $R_1$, $R_2$, $R_3$, and $R_4$ is hydroxy, and the other three are hydrogen. In certain embodiments, the polymerizing moiety can have formula (VII-A):

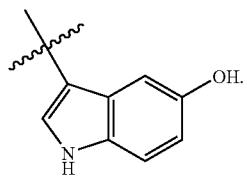

(VII-A)

In some embodiments, monomeric substrates having two or more polymerizing moieties can include one or more polymerizing moieties having formula (III):

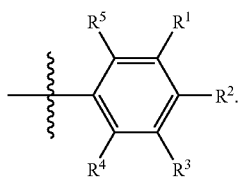

(III)

In all embodiments, at least one of $R^1$, $R^2$, $R^3$, $R^4$, and $R^5$ is a hydroxy group (OH), and the other are each, independently of one another, H; $C_1$-$C_6$ alkyl; $C_1$-$C_6$ alkoxy, amino, $C_1$-$C_6$ alkylamino, $C_1$-$C_6$ dialkylamino, $C_1$-$C_6$ alkylcarboxamido, or another hydroxy group, provided that at least one of $R^1$, $R^2$, $R^3$, $R^4$ and $R^5$ is hydrogen.

Numerous structural variations are permissible in the phenolic ring. In some embodiments, a second hydroxy group or a $C_1$-$C_6$ alkoxy group, can be located at an ortho position relative to the requisite hydroxy group.

In some embodiments, an amino group, a $C_1$-$C_6$ alkylamino or dialkylamino group, or a $C_1$-$C_6$ alkylcarboxamido group can be located at an meta position relative to the requisite hydroxy group.

In some embodiments, $R^2$ can be hydroxy, and each of $R^1$, $R^3$, $R^4$, and $R^5$ can be hydrogen.

In some embodiments, $R^2$ can be hydroxy; $R^1$ can be hydroxy group or a $C_1$-$C_6$ alkoxy group; and each of $R^3$, $R^4$, and $R^5$ can be hydrogen. In certain embodiments, each of $R^1$ and $R^2$ can be hydroxy, and each of $R^3$, $R^4$, and $R^5$ can be hydrogen.

The effect(s) of the various substitutions possible on the phenolic ring can be predicted by one of skill in the art according to known principles of organic chemistry, based on the identities of the substituents and their relative positions on the ring. See, e.g., L. G. Wade, Jr., 1988, *Organic Chemistry*, Prentice-Hall, Inc., Englewood Cliffs, N.J. at 666-669. For example, an amino group at the meta position (relative to the hydroxyl group) is strongly activating, i.e., it makes the ring a better electron donor, and thus more reactive.

A phenolic ring can undergo oxidation to form free radical intermediates, which in turn can participate in bond forming reactions (e.g., carbon-carbon bond forming reactions, e.g., free radical polymerization reactions) under certain conditions. Based on well-known chemistry, it is predicted, for example, that phenolic polymerization occurs when a phenolic free radical is generated by loss of an electron from a phenolic moiety.

This occurs, for example, when each of two phenolic moieties donates one electron apiece in the reaction $H_2O_2 \rightarrow 2H_2O$ catalyzed by myeloperoxidase. Two phenolic free radicals then react with each other to form a covalent linkage.

The phenolic free radicals can be described by several resonance forms in which the unpaired electron is delocalized among different positions on the aromatic ring, as well as on the oxygen. It is understood that the actual electronic structure of some chemical entities cannot be adequately represented by only one canonical form (i.e. Lewis structure). The actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species.

Covalent coupling of the free radicals in various linkages, can give rise to a mixture of different polymerized products. Information concerning phenolic polymerization reactions and mechanisms of enzymes such as peroxidases, laccases, and tyrosinases is known in the art. See, e.g., Akkara et al., 1994, *Biomimetics* 2:331-339; Saunders et al., 1963, *Peroxidase*, Butterworth, Washington, D.C.; Akkara et al., 1991, *J. Polymer. Sci.* 29:1561-1574; Crestini et al., 2000, *Bioorg. Med. Chem.* 8:433-438; Guerra et al., 2000, *Enzyme Microb. Technol.* 26:315-323.

Linker Moieties

Because its function is simply to connect the chelating moiety to the polymerizing moiety, there are no strict structural requirements for the linker moiety, when present. Once incorporated in the monomeric substrate, the linker moiety need not participate in any chemical reaction or any particular binding interaction. Thus, the linker moiety can be chosen or designed primarily based on factors such as convenience of synthesis, lack of steric hindrance, and biodegradation properties. A linker moiety containing one or more, e.g., 2-6, L-amino acids is preferred, because their carboxyl groups and amino groups are convenient for employment in synthesis of the monomeric substrate, the peptide bonds are biodegradable, and the products of polypeptide degradation are non-toxic. Amino acids such as glycine and alanine are preferred amino acids, because they do not have bulky or reactive side chains. In certain embodiments, linker moieties include one or more amide groups (—C(O)NH—), which can be flanked by branched or unbranched alkylene groups.

Structure of Monomeric Substrates

In general, a monomeric substrate can have the following general structur (A):

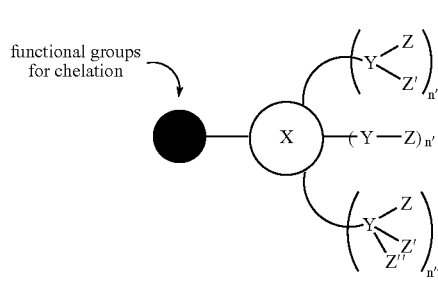

(A)

in which X is a chelator moiety (e.g., any chelator moiety described herein); each Y is a linker moiety (e.g., any linker moiety described herein); each of Z, Z', and Z" are polymerizing moieties, (e.g., each of which can be a polymerizing moiety having formula (II), (III), (IV), (V), (VI), (VII), or (VIII), or any polymerizing moiety described herein), and can be the same or different. Each of n', n", and n'" can be, independently of one another, 0, 1, 2, 3, 4, 5, 6, 7, 8, 9, or 10.

In some embodiments, a substrate moiety can have a single polymerizing moiety, i.e., n' is 1, and n", and n'" are both 0. Z can be a polymerizing moiety having formula (II), (IV), (V), (VI), (VII), or (VIII).

In other embodiments, a substrate moiety can have at least two polymerizing moieties. Each of n', n", and n'" can be, independently of one another, 0, 1, 2, 3, 4, 5, 6, 7, 8, 9, or 10, provided that n' is $\geq 2$ when n" and n'" are both 0, and further provided that one of n" or n'" is 1 when n' is 0.

In certain embodiments, n' can be 3, 2, or 1, and each of n" and n'" can be, independently of one another, 0, 1, or 2, provided that both n" and n'" are other than 0.

By way of example, a monomeric substrate can have formula (B):

(B)

in which X is a chelator moiety (e.g., any chelator moiety described herein); each Y is a linker moiety (e.g., any chelator moiety described herein); each Z is a polymerizing moiety (e.g., a polymerizing moiety having formula (I), (II), (III), (IV), (V), (VI), or (VII), e.g., any polymerizing moiety described herein); each m can be, independently of one another, 1, 2, 3, 4, 5, 6, 7, 8, 9, or 10 (e.g., 1, 2, or 3); and n can be 2, 3, 4, 5, 6, 7, 8, 9, or 10 (e.g., 2, 3, 4, 5, or 6). In certain embodiments, a monomeric substrate can include 2, 3, 4, 5, 6, 7, 8, or 9 polymerizing moieties, which can be the same or different (e.g., the monomeric substrate can include two or more different polymerizing moieties).

In certain embodiments, m can be 1. In certain embodiments, n can be 2. In certain embodiments, m can be 1 and n can be 2.

In some embodiments, monomeric substrates containing one or more polymerizing moieties can have formula (IX):

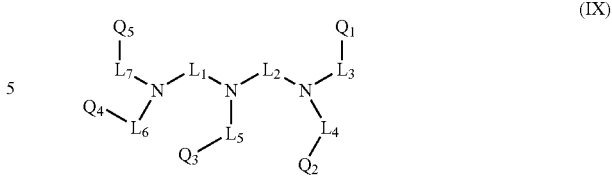

(IX)

Each of $L_1$ and $L_2$ can be, independently of one another:

(i) $C_1$-$C_{20}$ (e.g., $C_1$-$C_{10}$, $C_1$-$C_6$, $C_1$-$C_3$; $C_{10}$-$C_{20}$) alkylene, optionally inserted (for alkylene moieties having 2-20 carbons) with 1-10 (e.g., 1-5, 1-4, 1-3, 1-2, 1) heteroatoms (e.g., $NR^N$, O, or S) and/or optionally substituted with 1-10 (e.g., 1-5, 1-4, 1-3, 1-2, 1) $R^i$; or (ii) $C_2$-$C_{20}$ (e.g., $C_2$-$C_{12}$, $C_2$-$C_8$, $C_2$-$C_6$; $C_{10}$-$C_{20}$) alkenylene, optionally inserted (for alkenylene moieties having 2-20 carbons) with 1-10 (e.g., 1-5, 1-4, 1-3, 1-2, 1) heteroatoms (e.g., N, O, or S) and/or optionally substituted with 1-10 (e.g., 1-5, 1-4, 1-3, 1-2, 1) $R^i$; or (iii) $C_2$-$C_{20}$ (e.g., $C_2$-$C_{12}$, $C_2$-$C_8$, $C_2$-$C_6$; $C_{10}$-$C_{20}$) alkynylene, optionally inserted (for alkynylene moieties having 2-20 carbons) with 1-10 (e.g., 1-5, 1-4, 1-3, 1-2, 1) heteroatoms (e.g., N, O, or S) and/or optionally substituted with 1-10 (e.g., 1-5, 1-4, 1-3, 1-2, 1) $R^i$; or (iv) $C_3$-$C_{20}$ (e.g., $C_3$-$C_{16}$, $C_3$-$C_{12}$, $C_3$-$C_8$) cycloalkylene, each of which can be optionally inserted with 1-10 (e.g., 1-5, 1-4, 1-3, 1-2, 1) heteroatoms (e.g., N, O, or S) and/or optionally substituted with 1-10 (e.g., 1-5, 1-4, 1-3, 1-2, 1) $R^i$.

Each of $L_3$, $L_4$, $L_5$, $L_6$, and $L_7$ can be, independently of one another: (i) any one of the substituents defined for $L^1$ and $L^2$; or (ii) a bond.

Each of $Q_1$, $Q_2$, $Q_3$, $Q_4$, and $Q_5$ can be, independently of one another:

(i) Z (e.g., a polymerizing moiety having formula (II), (III), (IV), (V), (VI), (VII), or (VIII), or any polymerizing moiety described herein);

(ii) Q'-Z; or (iii) $OR^m$; $O^-R^+$; $O^-R^{(+)}$; $NR^jR^k$; —$C(O)NR^jR^k$; —$OC(O)NR^jR^k$; —$C(O)R^m$, —$C(O)OR^m$; —$C(O)O^-R^+$; —$C(O)O^-R^{(+)}$; —$OC(O)R^m$; —$C(O)SR^m$; —$C(O)S^-R^+$; —$C(O)S^-R^{(+)}$; —$SC(O)R^m$; —$C(S)SR^m$; —$C(S)S^-R^+$; —$C(S)S^-R^{(+)}$; —$SC(S)R^m$; —$NR''C(O)R^m$; —$NR''C(O)OR^m$; —$NR''C(O)NR^jR^k$; —$S(O)_sOR^m$; —$S(O)_sO^-R^+$; —$S(O)_sO^-R^{(+)}$; —$NR''S(O)_sOR^m$; —$NR''S(O)_sO^-R^+$; —$NR''S(O)_sO^-R^{(+)}$; —$C(NR^o)R^m$; —$P(O)(OR^p)(OR^q)$; —$P(O)(OR^p)(O^-R^+)$; —$P(O)(OR^p)(O^-R^{(+)})$; —$P(O)(O^-R^+)(O^-R^+)$; —$P(O)(O^-R^+)(O^-R^{(+)})$; or —$P(O)(O^-R^{(+)})(O^-R^{(+)})$, in which Z, $R^j$, $R^k$, $R^m$, $R^n$, $R^o$, $R^p$, $R^q$, $R^+$, and $R^{(+)}$ are as defined elsewhere herein.

Each Q' can be, independently of one another, —$C(O)NR^jL^{10}$-; —$OC(O)NR^jL^{10}$-; —$C(O)L^{10}$-, —$C(O)OL^{10}$-; —$OC(O)L^{10}$-; —$OC(O)OL^{10}$-; —$C(O)SL^{10}$-; —$SC(O)L^{10}$-; —$C(S)SL^{10}$-; —$SC(S)L^{10}$-; —$NR^jC(O)L^{10}$-; —$NR^jC(O)OL^{10}$-; —$NR''C(O)NR^jL^{10}$-; —$S(O)_sOL^{10}$; —$OS(O)_sL^{10}$-; —$NR''S(O)_sOL^{10}$-; —$O(O)_sSNR''L^{10}$-; —$C(NR^o)L^{10}$-; —$P(O)(OR^p)L^{10}$-; or —$(OR^p)P(O)L^{10}$-, in which $R^j$, $R''$, and $R^p$, are as defined elsewhere herein, and $L^{10}$ is attached to Z.

Each $R^i$ can be, independently of one another:

(i) Z (e.g., a polymerizing moiety having formula (II), (III), (IV), (V), (VI), (VII), or (VIII), or any polymerizing moiety described herein); or (ii) halo; $OR^m$; $O^-R^+$; $O^-R^{(+)}$; halo; $NR^jR^k$; nitro; azido; oxo; thioxo; $C_1$-$C_{12}$ alkoxy; $C_1$-$C_{12}$ haloalkoxy; —$C(O)NR^jR^k$; —$OC(O)NR^jR^k$; —$C(O)R^m$, —$C(O)OR^m$; —$C(O)O^-R^+$; —$C(O)O^-R^{(+)}$; —$OC(O)R^m$; —$C(O)SR^m$; —$C(O)S^-R^+$;

—C(O)S⁻R$^{(+)}$; —SC(O)R$^m$; —C(S)SR$^m$; —C(S)S⁻R⁺; —C(S)S⁻R$^{(+)}$; —SC(S)R$^m$; —NR″C(O)R$^m$; —NR″C(O)OR$^m$; —NR″C(O)NR$^j$R$^k$; —S(O)$_s$OR$^m$; —S(O)$_s$O⁻R⁺; —S(O)$_s$O⁻R$^{(+)}$; —NR″S(O)$_s$OR$^m$; —NR″S(O)$_s$O⁻R⁺; —NR″S(O)$_s$O⁻R$^{(+)}$; —C(NR$^o$)R$^m$; —P(O)(OR$^p$)(OR$^q$); —P(O)(OR$^p$)(O⁻R⁺); —P(O)(OR$^p$)(O⁻R$^{(+)}$); —P(O)(O⁻R⁺)(O⁻R⁺); —P(O)(O⁻R⁺)(O⁻R$^{(+)}$); or —P(O)(O⁻R$^{(+)}$)(O⁻R$^{(+)}$), in which Z, R$^j$, R$^k$, R$^m$, R$^n$, R$^o$, R$^p$, R$^q$, R⁺, and R$^{(+)}$ can be as defined elsewhere herein.

Each R$^j$, R$^k$, and R$^o$ can be, independently of one another, H, $C_1$-$C_{10}$ (e.g., $C_1$-$C_6$, $C_1$-$C_3$) alkyl, OH, O⁻R⁺, or O⁻R$^{(+)}$. Each R$^m$, R$^n$, R$^p$, R$^q$, and R$^N$ can be, independently of one another, H or $C_1$-$C_{10}$ (e.g., $C_1$-$C_6$, $C_1$-$C_3$) alkyl, $C_1$-$C_{10}$ (e.g., $C_1$-$C_6$, $C_1$-$C_3$) haloalkyl, or $C_6$-$C_{20}$ aryl. Each s can be 0, 1, or 2. Each L$^{10}$ can be, independently of one another, as defined for $L_3$, $L_4$, $L_5$, $L_6$, and $L_7$.

Each R⁺ can be, independently of one another, an inorganic or organic cationic moiety, e.g., an alkali metal (e.g., sodium (Na⁺), potassium (K⁺)), alkaline earth metal (e.g., magnesium (Mg$^{2+}$), calcium (Ca$^{2+}$)), ammonium (NH$_4^+$), or any quaternized basic nitrogen-containing group, (e.g., N(alkyl)$_4^+$, NH(alkyl)$_3^+$, pyridinium). In certain embodiments, R⁺ can be the conjugate acid that forms as a result of contacting a relatively acidic moiety (e.g., when R$^i$ is —COOH) with an inorganic or organic base (e.g., NaOH or pyridine).

R$^{(+)}$ refers to a chelated (super)paramagnetic or radioactive metal atom or ion.

In some embodiments, each R$^i$ can be, independently of one another:

(i) Z (e.g., a polymerizing moiety having formula (II), (III), (IV), (V), (VI), (VII), or (VIII), e.g., any polymerizing moiety described herein); or (ii) C(O)OR$^m$, in which R$^m$ can be H; —C(O)O⁻R⁺; or —C(O)O⁻R$^{(+)}$; or (iii) —P(O)(OR$^p$)(OR$^q$); —P(O)(OR$^p$)(O⁻R⁺); —P(O)(OR$^p$)(O⁻R$^{(+)}$); —P(O)(O⁻R⁺)(O⁻R⁺); —P(O)(O⁻R⁺)(O⁻R$^{(+)}$); or —P(O)(O⁻R$^{(+)}$)(O⁻R$^{(+)}$), in which each of R$^p$ and R$^q$ can be H; or (iv) —C(O)NR$^j$R$^k$, in which one of R$^j$ and R$^k$ is H, and the other is OH, O⁻R⁺, O⁻R$^{(+)}$, or (v) oxo.

In some embodiments, each of $L_1$, $L_2$, $L_3$, $L_4$, $L_5$, $L_6$, and $L_7$ can be, independently of one another:

(i) unsubstituted $C_1$-$C_6$ alkylene (e.g., —CH$_2$—, —CH$_2$CH$_2$—, or CH$_2$CH$_2$CH$_2$—), or (ii) $C_1$-$C_6$ alkylene substituted with 1-3 R$^i$ (e.g., —CH$_2$CH(R$^i$)—, —CH(R$^i$)CH$_2$—, —CH(R$^i$)CH(R$^i$)—, —CH$_2$CH$_2$CH(R$^i$)—, —CH(R$^i$)CH$_2$CH$_2$—, —CH(R$^i$)CH$_2$CH(R$^i$)—, or —CH(R$^i$)CH(O)CH(R$^i$)—).

In certain embodiments, each of $L_1$ and $L_2$ can be independently of one another, unsubstituted $C_1$-$C_6$ alkylene (e.g., —CH$_2$—, —CH$_2$CH$_2$—, or CH$_2$CH$_2$CH$_2$—). In certain embodiments, $L_1$ and $L_2$ can both be —CH$_2$CH$_2$—.

In certain embodiments, each of $L_3$, $L_4$, $L_5$, $L_6$, and $L_7$ can be, independently of one another, unsubstituted $C_1$-$C_6$ alkylene (e.g., —CH$_2$—, —CH$_2$CH$_2$—, or CH$_2$CH$_2$CH$_2$—). In certain embodiments, $L_3$, $L_4$, $L_5$, $L_6$, and $L_7$ can each be —CH$_2$—.

In certain embodiments, $L_1$ and $L_2$ can both be —CH$_2$CH$_2$—, and $L_3$, $L_4$, $L_5$, $L_6$, and $L_7$ can each be —CH$_2$—.

In some embodiments, each of $L_1$ and $L_2$ can be, independently of one another (i) unsubstituted $C_1$-$C_{12}$ alkylene (e.g., $C_1$-$C_6$ alkylene or $C_7$-$C_{12}$ alkylene), or (ii) $C_1$-$C_{12}$ alkylene (e.g., $C_1$-$C_6$ alkylene or $C_7$-$C_{12}$ alkylene, $C_4$ or $C_9$ alkylene) substituted with 1-5 (e.g., 1, 2, or 3) R$^i$ (e.g., oxo) and inserted with from 1-3 (e.g., 1 or 2) heteroatoms (e.g., NR$^N$, e.g., NH).

In some embodiments, both $L_3$ and $L_4$ can be a bond, or one of $L_3$ and $L_4$ can be a bond, and the other can be: (i) unsubstituted $C_1$-$C_{10}$ alkylene (e.g., $C_1$-$C_8$, $C_1$-$C_6$ alkylene), or (ii) $C_1$-$C_{10}$ (e.g., $C_1$-$C_8$, $C_1$-$C_6$) alkylene substituted with 1-3 R$^i$.

In some embodiments, both $L_6$ and $L_7$ can be a bond, or one of $L_6$ and $L_7$ can be a bond, and the other can be: (i) unsubstituted $C_1$-$C_{10}$ alkylene (e.g., $C_1$-$C_8$, $C_1$-$C_6$ alkylene), or (ii) $C_1$-$C_{10}$ (e.g., $C_1$-$C_8$, $C_1$-$C_6$) alkylene substituted with 1-3 R$^i$.

In some embodiments, $L_5$ can be a bond.

In certain embodiments, each of $L_1$ and $L_2$ can be, independently of one another, $C_1$-$C_{12}$ alkylene (e.g., $C_1$-$C_6$, $C_7$-$C_{12}$ alkylene, e.g., $C_4$ or $C_9$ alkylene) substituted with 1-5 (e.g., 1, 2, or 3, e.g., 2) R$^i$ (e.g., oxo) and inserted with from 1-3 (e.g., 1 or 2) heteroatoms (e.g., 1 heteroatom, e.g., NR$^N$, e.g., NH). For example, each of $L_1$ and $L_2$ can be independently of one another, $C_1$-$C_{12}$ alkylene (e.g., $C_1$-$C_6$, $C_7$-$C_{12}$ alkylene, e.g., $C_4$ or $C_9$ alkylene) substituted with 2 oxo groups and inserted with —NH—. The oxo groups can be substituted on carbon atoms adjacent to nitrogen atoms. In certain embodiments, $L_1$ and $L_2$ can both be —C(O)CH$_2$CH$_2$C(O)NH(CH$_2$)$_5$— (either terminus can be attached to the nitrogen between $L_1$ and $L_2$).

In certain embodiments, both $L_3$ and $L_4$ can be a bond; and one of $L_6$ and $L_7$ can be a bond, and the other can be unsubstituted $C_1$-$C_{10}$ alkylene (e.g., $C_1$-$C_8$, $C_1$-$C_6$ alkylene, e.g., $C_5$ alkylene) (or one of $L_3$ and $L_4$ can be a bond, and the other can be unsubstituted $C_1$-$C_{10}$ alkylene (e.g., $C_1$-$C_8$, $C_1$-$C_6$ alkylene, e.g., $C_5$ alkylene), and both $L_6$ and $L_7$ can be a bond).

In certain embodiments: $L_1$ and $L_2$ can both be $C_1$-$C_{12}$ alkylene (e.g., $C_1$-$C_6$, $C_7$-$C_{12}$ alkylene, e.g., $C_4$ or $C_9$ alkylene) substituted with 1-5 (e.g., 1, 2, or 3, e.g., 2) R$^i$ (e.g., oxo) and inserted with from 1-3 (e.g., 1 or 2) heteroatoms (e.g., $L_1$ and $L_2$ can be the same or different, e.g. $L_1$ and $L_2$ can both be —C(O)CH$_2$CH$_2$C(O)NH(CH$_2$)$_5$—); and $L_3$ and $L_4$ can both be a bond; and one of $L_6$ and $L_7$ can be a bond, and the other can be unsubstituted $C_5$ alkylene (or one of $L_3$ and $L_4$ can be a bond, and the other can be unsubstituted $C_5$ alkylene, and both $L_6$ and $L_7$ can be a bond); and $L_5$ can be a bond.

In some embodiments, each of $Q_1$, $Q_2$, $Q_3$, $Q_4$, and $Q_5$ can be, independently of one another:

(i) Z (e.g., a polymerizing moiety having formula (II), (III), (IV), (V), (VI), (VII), or (VIII), e.g., any polymerizing moiety described herein);

(ii) Q'-Z, in which Q' can be —C(O)OL$^{10}$-, —OC(O)L$^{10}$-, —C(O)NR$^j$L$^{10}$- (e.g., R$^j$ can be H), —NR$^j$C(O)L$^{10}$- (e.g., R$^j$ can be H), —OC(O)OL$^{10}$-, or —NR″C(O)NR$^j$L$^{10}$- (e.g., R$^j$ and R″ can each be H); Z can be a polymerizing moiety (e.g., a polymerizing moiety having formula (II), (III), (IV), (V), (VI), (VII) or (VIII), e.g., any polymerizing moiety described herein; and L$^{10}$ can be —CH$_2$—, —CH$_2$CH$_2$—; or (iii) C(O)OR$^m$, in which R$^m$ can be H; —C(O)O⁻R⁺; or —C(O)O⁻R$^{(+)}$; or (iv) —P(O)(OR$^p$)(OR$^q$); —P(O)(OR$^p$)(O⁻R⁺); —P(O)(OR$^p$)(O⁻R$^{(+)}$); —P(O)(O⁻R⁺)(O⁻R⁺); —P(O)(O⁻R⁺)(O⁻R$^{(+)}$); or —P(O)(O⁻R$^{(+)}$)(O⁻R$^{(+)}$), in which each of R$^p$ and R$^q$ can be H; or (v) —C(O)NR$^j$R$^k$, in which one of R$^j$ and R$^k$ is H, and the other is OH, O⁻R⁺, or O⁻R$^{(+)}$; or (vi) OH, O⁻R⁺, or O⁻R$^{(+)}$; or (vii) —C(O)R$^m$, in which R$^m$ is $C_1$-$C_6$ alkyl (e.g., CH$_3$), provided that one of $Q_1$, $Q_2$, $Q_3$, $Q_4$, and $Q_5$ is Z or Q'-Z.

In certain embodiments, one of $Q_1$, $Q_2$, $Q_3$, $Q_4$, and $Q_5$ (e.g., $Q_1$ or $Q_2$ or $Q_4$ or $Q_5$) can be Q'-Z, and the other four can be, independently of one another:

(iii) $C(O)OR^m$, in which $R^m$ can be H; $-C(O)O^-R^+$; or $-C(O)O^-R^{(+)}$; or (iv) $-P(O)(OR^p)(OR^q)$; $-P(O)(OR^p)(O^-R^+)$; $-P(O)(OR^p)(O^-R^{(+)})$; $-P(O)(O^-R^+)(O^-R^+)$; $-P(O)(O^-R^+)(O^-R^{(+)})$; or $-P(O)(O^-R^{(+)})(O^-R^{(+)})$, in which each of $R^p$ and $R^q$ can be H; or (v) $-C(O)NR^jR^k$, in which one of $R^j$ and $R^k$ is H, and the other is OH, $O^-R^+$, $O^-R^{(+)}$; or (vi) OH, $O^-R^+$, $O^-R^{(+)}$; or (vii) $-C(O)R^m$, in which $R^m$ is $C_1$-$C_6$ alkyl (e.g., $CH_3$).

In certain embodiments, each Q' can be, independently of one another, $-C(O)OL^{10}-$, $-OC(O)L^{10}-$, $-C(O)NR^jL^{10}-$ (e.g., $R^j$ can be H), $-NR^jC(O)L^{10}-$ (e.g., $R^j$ can be H), $-OC(O)OL^{10}-$, or $-NR''C(O)NR^jL^{10}-$ (e.g., $R^j$ and $R''$ can each be H); Z can be a polymerizing moiety (e.g., a polymerizing moiety having formula (II), (III), (IV), (V), (VI), (VII) or (VIII), e.g., any polymerizing moiety described herein; and $L^{10}$ can be $-CH_2-$, $-CH_2CH_2-$.

In certain embodiments, two of $Q_1$, $Q_2$, $Q_3$, $Q_4$, and $Q_5$ (e.g., $Q_1$ or $Q_2$ and $Q_4$ or $Q_5$) can be Q'-Z, and the other three can be, (iii) $C(O)OR^m$, in which $R^m$ can be H; $-C(O)O^-R^+$; or $-C(O)O^-R^{(+)}$; or (iv) $-P(O)(OR^p)(OR^q)$; $-P(O)(OR^p)(O^-R^+)$; $-P(O)(OR^p)(O^-R^{(+)})$; $-P(O)(O^-R^+)(O^-R^+)$; $-P(O)(O^-R^+)(O^-R^{(+)})$; or $-P(O)(O^-R^{(+)})(O^-R^{(+)})$, in which each of $R^p$ and $R^q$ can be H; or (v) $-C(O)NR^jR^k$, in which one of $R^j$ and $R^k$ is H, and the other is OH, $O^-R^+$, $O^-R^{(+)}$; or (vi) OH, $O^-R^+$, $O^-R^{(+)}$; or (vii) $-C(O)R^m$, in which $R^m$ is $C_1$-$C_6$ alkyl (e.g., $CH_3$).

In certain embodiments, each Q' can be, independently of one another, $-C(O)OL^{10}-$, $-OC(O)L^{10}-$, $-C(O)NR^jL^{10}-$ (e.g., $R^j$ can be H), $-NR^jC(O)L^{10}-$ (e.g., $R^j$ can be H), $-OC(O)OL^{10}-$, or $-NR''C(O)NR^jL^{10}-$ (e.g., $R^j$ and $R''$ can each be H); Z can be a polymerizing moiety (e.g., a polymerizing moiety having formula (II), (III), (IV), (V), (VI), (VII) or (VIII), e.g., any polymerizing moiety described herein; and $L^{10}$ can be $-CH_2-$, $-CH_2CH_2-$.

In certain embodiments, three of $Q_1$, $Q_2$, $Q_3$, $Q_4$, and $Q_5$ (e.g., $Q_1$ or $Q_2$; $Q_3$; and $Q_4$ or $Q_5$) can be Q'-Z, and the other two can be:

(iii) $C(O)OR^m$, in which $R^m$ can be H; $-C(O)O^-R^+$; or $-C(O)O^-R^{(+)}$; or (iv) $-P(O)(OR^p)(OR^q)$; $-P(O)(OR)(O^-R^+)$; $-P(O)(OR^p)(O^-R^{(+)})$; $-P(O)(O^-R^+)(O^-R^+)$; $-P(O)(O^-R^+)(O^-R^{(+)})$; or $-P(O)(O^-R^{(+)})(O^-R^{(+)})$, in which each of $R^p$ and $R^q$ can be H; or (v) $-C(O)NR^jR^k$, in which one of $R^j$ and $R^k$ is H, and the other is OH, $O^-R^+$, $O^-R^{(+)}$; or (vi) OH, $O^-R^+$, $O^-R^{(+)}$; or (vii) $-C(O)R^m$, in which $R^m$ is $C_1$-$C_6$ alkyl (e.g., $CH_3$).

In certain embodiments, each Q' can be, independently of one another, $-C(O)OL^{10}-$, $-OC(O)L^{10}-$, $-C(O)NR^jL^{10}-$ (e.g., $R^j$ can be H), $-NR^jC(O)L^{10}-$ (e.g., $R^j$ can be H), $-OC(O)OL^{10}-$, or $-NR''C(O)NR^jL^{10}-$ (e.g., $R^j$ and $R''$ can each be H); Z can be a polymerizing moiety (e.g., a polymerizing moiety having formula (II), (III), (IV), (V), (VI), (VII) or (VIII), e.g., any polymerizing moiety described herein; and $L^{10}$ can be $-CH_2-$, $-CH_2CH_2-$.

Representative monomeric substrates of formula (IX) are provided below.

In certain embodiments, each of $L_1$ and $L_2$ can be, independently of one another, unsubstituted $C_1$-$C_6$ alkylene (e.g., $L_1$ and $L_2$ can both be $-CH_2CH_2-$); each of $L_3$, $L_4$, $L_5$, $L_6$, and $L_7$ can be, independently of one another, unsubstituted $C_1$-$C_6$ alkylene (e.g., $L_3$, $L_4$, $L_5$, $L_6$, and $L_7$ can each be $-CH_2-$); and two of $Q_1$, $Q_2$, $Q_3$, $Q_4$, and $Q_5$ (e.g., $Q_1$ or $Q_2$ and $Q_4$ or $Q_5$) can be Q'-Z (e.g., $-C(O)NHL^{10}$-Z, in which Z can be 4-hydroxyphenyl or 5-hydroxy-3-indolyl), and the other three can be $C(O)OR^m$ (e.g., $-COOH$). $L^{10}$ can be $C_1$-$C_{10}$ alkylene (e.g., $-CH_2-$ or $-CH_2CH_2-$). By way of example, representative monomeric substrates of formula (IX) can include compounds 1 and 2:

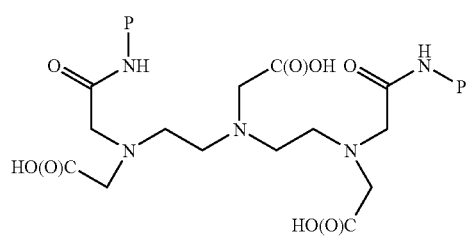

in which P can be:

1: P = 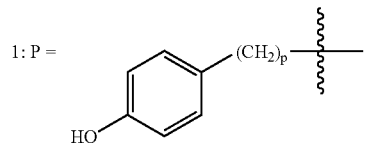

2: P = 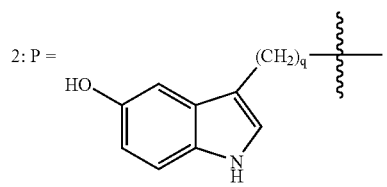

(p is 1-10, and is preferably 2; q is 1-10, and is preferably 2).

In other embodiments:

$L_1$ and $L_2$ can be $C_1$-$C_{12}$ alkylene (e.g., $C_1$-$C_6$, $C_7$-$C_{12}$ alkylene, e.g., $C_4$ or $C_9$ alkylene) substituted with 1-5 (e.g., 1, 2, or 3, e.g., 2) $R^i$ (e.g., oxo) and inserted with from 1-3 (e.g., 1 or 2) heteroatoms (e.g., 1 heteroatom, e.g., $NR^N$, e.g., NH) (e.g., $L_1$ and $L_2$ can both be $-C(O)CH_2CH_2C(O)NH(CH_2)_5-$); and $L_3$ can be a bond, and $Q_1$ can be OH, $O^-R^+$, $O^-R^{(+)}$; and $L_4$ can be a bond, and $Q_2$ can be $-C(O)R^m$ (e.g. $-C(O)CH_3$); and $L_5$ can be a bond, and $Q_3$ can be OH, $O^-R^+$, $O^-R^{(+)}$; and $L_6$ can be a bond, and $Q_4$ can be OH, $O^-R^+$, $O^-R^{(+)}$; and $L_7$ can be $C_1$-$C_{10}$ alkylene (e.g., $C_5$ alkylene), and $Q_5$ can be Q'-Z (e.g., $-C(O)NHL^{10}$-Z, in which Z can be 5-hydroxy-3-indolyl and $L^{10}$ can be $C_1$-$C_{10}$ alkylene (e.g., $-CH_2-$ or $-CH_2CH_2-$)). By way of example, representative monomeric substrates of formula (IX) can also include compounds having the structure shown below:

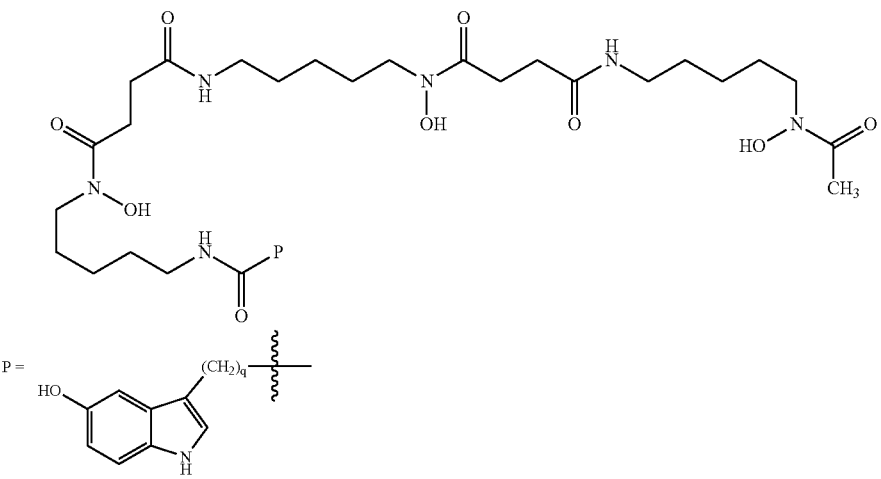

3

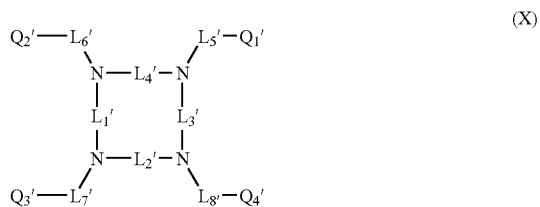

(q is 1-10, and is preferably 1, which is referred to herein as compound 3).

In some embodiments, monomeric substrates containing one or more polymerizing moieties can have formula (X):

$$Q_2'—L_6' \quad L_5'—Q_1'$$
(with structure as shown)
$$Q_3'—L_7' \quad L_8'—Q_4'$$
(X)

in which $L_{1'}$, $L_{2'}$, $L_{3'}$, $L_{4'}$ can be as defined throughout for $L_1$ and $L_2$ in formula (IX); similarly, $L_{5'}$, $L_{6'}$, $L_{7'}$, and $L_{8'}$ have the same definitions throughout as those delineated for the group of substituents $L_3$, $L_4$, $L_5$, $L_6$, and $L_7$ in formula (IX); and $Q_{1'}$, $Q_{2'}$, $Q_{3'}$, and $Q_{4'}$ can be as defined throughout for $Q_1$, $Q_2$, $Q_3$, $Q_4$, and $Q_5$ in formula (IX).

In some embodiments, each of $L_{1'}$, $L_{2'}$, $L_{3'}$, and $L_{4'}$ can be, independently of one another, unsubstituted $C_1$-$C_6$ alkylene (e.g., —CH$_2$—, —CH$_2$CH$_2$—, or CH$_2$CH$_2$CH$_2$—). In certain embodiments, $L_{1'}$, $L_{2'}$, $L_{3'}$, and $L_{4'}$ can each be —CH$_2$CH$_2$—.

In some embodiments, each of $L_{5'}$, $L_{6'}$, $L_{7'}$, and $L_{8'}$ can be, independently of one another, unsubstituted $C_1$-$C_6$ alkylene (e.g., —CH$_2$—, —CH$_2$CH$_2$—, or CH$_2$CH$_2$CH$_2$—). In certain embodiments, $L_{5'}$, $L_{6'}$, $L_{7'}$, and $L_{8'}$ can each be —CH$_2$—.

In some embodiments, one, two, three, or four of $Q_{1'}$, $Q_{2'}$, $Q_{3'}$, and $Q_{4'}$, can be Q'-Z, and the others can be:

(iii) C(O)OR$^m$, in which R$^m$ can be H; —C(O)O$^-$R$^+$; or —C(O)O$^-$R$^{(+)}$; or (iv) —P(O)(OR$^p$)(OR$^q$); —P(O)(OR$^p$)(O$^-$R$^+$); —P(O)(OR$^p$)(O$^-$R$^{(+)}$); —P(O)(O$^-$R$^+$)(O$^-$R$^+$); —P(O)(O$^-$R$^+$)(O$^-$R$^{(+)}$); or —P(O)(O$^-$R$^{(+)}$)(O$^-$R$^{(+)}$), in which each of R$^p$ and R$^q$ can be H; or (v) —C(O)NR$^j$R$^k$, in which one of R$^j$ and R$^k$ is H, and the other is OH, O$^-$R$^+$, O$^-$R$^{(+)}$; or (vi) OH, O$^-$R$^+$, O$^-$R$^{(+)}$; or (vii) —C(O)R$^m$, in which R$^m$ is $C_1$-$C_6$ alkyl (e.g., CH$_3$).

In certain embodiments, each Q' can be, independently of one another, —C(O)OL$^{10}$-, —OC(O)L$^{10}$-, —C(O)NR$^j$L$^{10}$- (e.g., R$^j$ can be H), —NR$^j$C(O)L$^{10}$- (e.g., R$^j$ can be H), —OC(O)OL$^{10}$-, or —NR$^{''}$C(O)NR$^j$L$^{10}$- (e.g., R$^j$ and R$^{''}$ can each be H); Z can be a polymerizing moiety (e.g., a polymerizing moiety having formula (II), (III), (IV), (V), (VI), (VII) or (VIII), e.g., any polymerizing moiety described herein; and L$^{10}$ can be —CH$_2$—, —CH$_2$CH$_2$—.

In certain embodiments, one or at least two of $Q_{1'}$, $Q_{2'}$, $Q_{3'}$, and $Q_{4'}$, is Q'-Z.

A representative monomeric substrate of formula (X) is provided below:

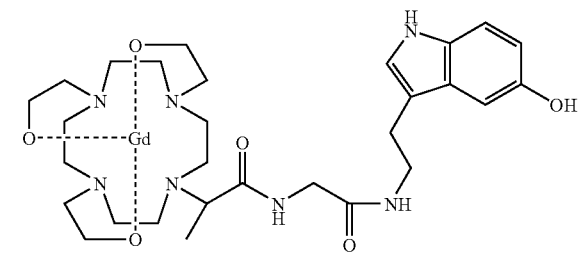

Although the invention is described here in terms of three distinct structural moieties in the monomeric substrate, those of skill in the art will recognize that there may not be a clearly defined dividing line between the chelating moiety and the linker moiety, and/or between the linker moiety and the polymerizing moiety. Whether, for example, one or more methylene groups are regarded as part of the linker moiety or part of the polymerizing moiety is essentially arbitrary. Moreover, those of skill in the art will recognize that the linking moiety does not necessarily represent a separate synthetic reagent. For example, in some embodiments, a glycine residue of the linker moiety derives from a portion of a glycylmethyl-DOTA tri-tBu ester reagent, and the other glycine residue derives from serotonin.

In the practice of this invention, in general, chelator moieties are interchangeable, polymerizing moieties are interchangeable, and linking moieties are interchangeable. Thus, numerous different combinations of a chelator moiety, polymerizing moieties, and a linking moieties are within the scope of the invention.

Synthesis of Monomeric Substrates

Each of the three structural moieties can be obtained commercially or synthesized according to methods described herein and/or conventional, organic chemical synthesis methods. Suitable covalent linkage of the three moieties can be carried out by one of skill in the art, employing conventional methods, without undue experimentation.

In general, monomeric substrates can be prepared by condensing one or more starting materials containing a nucleophilic group (e.g., a primary amine) with one or more starting material containing an electrophilic group (e.g., an activated carboxylic acid ester or a carboxylic acid anydride). Each of the aforementioned starting materials typically, but not necessarily, provides some or all of the constituent atoms for two of the three structural moieties present in the monomeric substrates. For example, a starting material (e.g., an electrophilic starting material) can provide some or all of the constituent atoms of the chelator moiety and the linking moieties. Similarly, a starting material (e.g., a nucleophilic starting material) can provide some or all of the constituent atoms of the polymerizing moieties and the linking moieties.

In some embodiments, monomeric substrates (e.g., monomeric substrates of formula (X)) can be synthesized according to the methods described in U.S. Pat. No. 6,737,247, or as described in Chen J W, Pham W, Weissleder R, Alexei Bogdanov J. Human myeloperoxidase: a potential target for molecular MR imaging in atherosclerosis. *Magn Reson Med* 2004; 52:1021-1028; and Querol M, Chen J, Weissleder R, Bogdanov A. DTPA-bisamide-based MR sensor agents for peroxidase imaging. *Org Lett* 2005; 7:1719-1722.

By way of example, the monomeric substrates 1 and 2 (described elsewhere herein) can be prepared by condensing an electrophilic starting material, DTPA-bisanhydride, with the nucleophilic starting materials, tyramine and serotonin, respectively (see Scheme 1 below).

Scheme 1

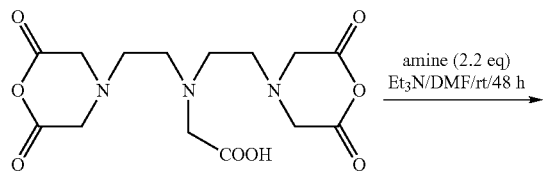

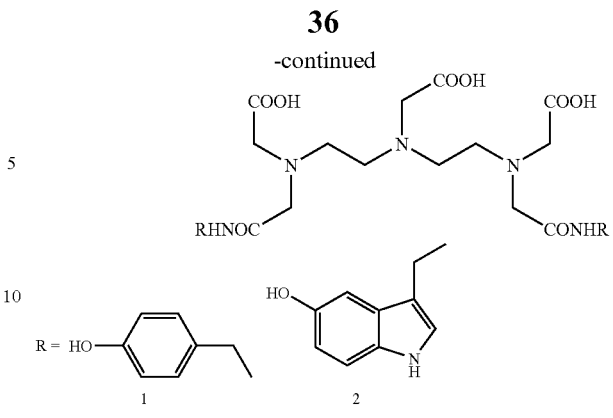

As shown in Scheme 1, freshly prepared DTPA-bisanhydride was combined with about 2.2 equivalents of tyramine and serotonin (e.g., about 2.2 equivalents) to provide compounds 1 and 2, respectively. In both cases, the reaction was conducted in DMF in the presence of an excess of $Et_3N$. Compounds 1 and 2 could each be isolated from the crude mixture by recrystallization from methanol and acetone and were used without further purification.

In some instances, the synthesis of corresponding $Gd^{3+}$ complexes was complicated by oxidation of the phenolic moieties. When compounds 1 or 2 were stirred either at rt. or at 60° C. with an excess of $Gd^{3+}$ salt (chloride or nitrate) at pH=7, the solution turned dark with the formation of insoluble products. To minimize the likelihood of excessive oxidation, the chelation was performed in the presence of citric acid (1% w/w) that resulted in a colorless reaction mixture. Attempts to precipitate the excess of $Gd^{3+}$ by raising the pH of the final solution to 10 at which $Gd^{3+}$ forms insoluble hydroxide were unsuccessful due to precipitation and decomposition of the complexes. The desired gadolinium complexes could be isolated in low yields after HPLC purification of the untreated reaction mixture, though compound $1Gd^{3+}$ always contained small amounts of its dimeric counterpart.

As a further example, monomeric substrates having structure 3 (described elsewhere herein) can be prepared with deferoxamine mesylate and 2-(5-hydroxy-1H-indol-3-yl)acetic acid according to Scheme 2 below:

Scheme 2

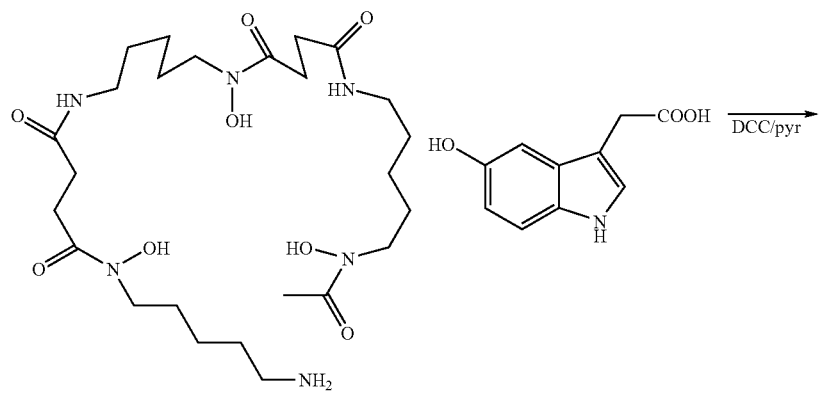

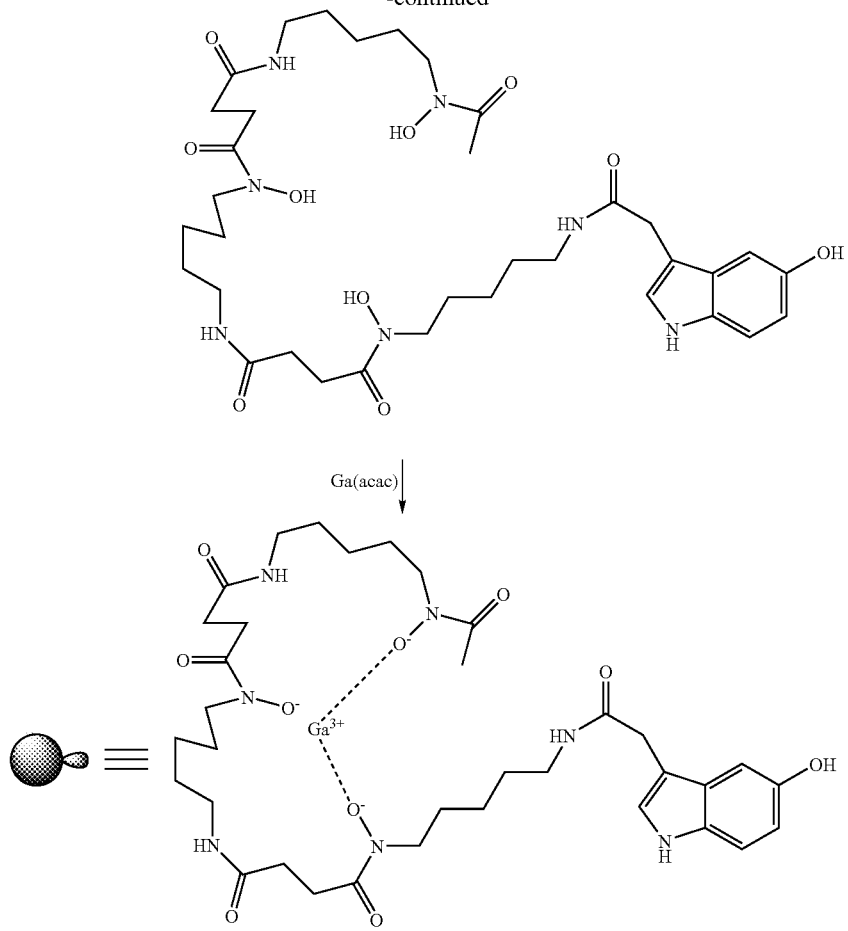

In general, the dicyclohexylcarbodiimide (DCC)-mediated coupling was carried out using an excess of the indole acetic acid to increase the likelihood of a complete reaction between the chelating moiety and exclusion of oxygen in the reaction set-up. An inert atmosphere was therefore employed to avoid undesirable oxidation of the phenolic moiety. Mixtures of DMSO/water or DMSO/acetonitrile together with the use of DCC in situ or pre-activation of the acid moiety with the pairs DCC/NHS or DCC/pyrazol were tested. The use of DCC in situ (instead of based on acid preactivation) together with a large excess of acid derivative enabled us to isolate the desired compound, after several precipitations and HPLC purification, as a white solid.

In general, the compounds described herein can be separated from a reaction mixture and further purified by a method such as column chromatography, high-pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, such as those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also contain linkages (e.g., carbon-carbon bonds and carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxy groups (e.g. L-arginine, -lysine, -histidine salts).

Pharmaceutical Compositions

The compounds and compositions described herein can be mixed with pharmaceutically acceptable carriers to form pharmaceutical compositions. The term "pharmaceutically acceptable carrier or adjuvant" refers to a carrier or adjuvant that may be administered to a subject (e.g., a patient), together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The compositions described herein can be administered orally, parenterally, by inhalation spray, topically, rectally, nasally, buccally, vaginally, or via an implanted reservoir. In certain embodiments, the compositions are administered by oral administration or administration by injection. The compositions can contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, can also be typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The new compositions may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions described herein can be useful when the desired treatment involves areas or organs readily accessible by topical application. For application topically to the skin, the composition should be formulated with a suitable ointment containing the active components suspended or dissolved in a carrier. Carriers for topical administration of the compounds described herein include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of this invention may also be topically applied to the lower intestinal tract by rectal suppository formulation or in a suitable enema formulation. Topically-transdermal patches are also included in this invention.

The compositions described herein may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The compounds and compositions described herein and an additional agent (e.g., a therapeutic agent) can also be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Enzyme-Mediated Reactions of Monomeric Substrates and Magnetic Resonance/SPECT Imaging of Target Enzymes General A target enzyme can be any enzyme capable of catalyzing polymerization of a monomeric substrate containing a chelated (super)paramagnetic metal or metal oxide or binding of the substrate to a macromolecule (e.g., a protein). This means that the target enzyme is chosen for compatibility with a given monomeric substrate, or that the monomeric substrate is designed for compatibility with a given type of target enzyme.

For example, the target enzyme can be a template-independent RNA or DNA polymerase, and the monomeric substrate can be a polymerizable nucleotide derivative.

Alternatively, the target enzyme can be an oxidoreductase, and the monomeric substrate can be an electron donor that undergoes, e.g., polymerization upon oxidation by the oxidoreductase. Useful oxidoreductases include peroxidases such as hydrogen peroxide-oxidoreductase (E.C. 1.11.1.7), lactoperoxidase, and horseradish peroxidase. In certain embodiments, the target enzyme can be a myeloperoxidase.

When a peroxidase is used, methods of the invention include providing a suitable amount of hydrogen peroxide in the tissue to be imaged. The hydrogen peroxide can be supplied directly. Alternatively, it can be generated in situ, e.g., using glucose oxidase. If the hydrogen peroxide is enzymatically generated in situ, the generating enzyme can be administered directly (as a pre-formed enzyme) or can be expressed in the tissue from a suitable nucleic acid vector introduced into the tissue.

In principle, the target enzyme can be an endogenous enzyme that occurs naturally in the tissue to be imaged. Typically, however, the target enzyme is an exogenous enzyme linked to a targeting moiety. The targeting moiety causes selective accumulation of the marker enzyme in the tissue to be imaged. In general, the targeting moiety binds selectively to a molecule exposed in an extracellular matrix or on the surface of one or more cell types found in the tissue to be imaged. An example of a useful targeting moiety is an antibody directed against a cell surface protein or carbohydrate. Alternatively, the targeting moiety can be, for example, a cell adhesion molecule, a cytokine, a cell surface receptor molecule, or a fragment thereof that recognizes the intended binding partner. In some embodiments, the targeting moiety and marker enzyme are covalently linked to form a single molecule. For example, a peroxidase enzyme can be covalently coupled to a primary targeting antibody, using a conventional coupling reaction. In other embodiments, the marker enzyme is coupled to a secondary targeting moiety, e.g., a secondary antibody, which recognizes a primary targeting moiety, e.g., a primary antibody. This approach represents an adaptation of conventional "sandwich ELISA" techniques.

Enzyme-catalyzed reactions that result in polymeric products are not limited to oxidation-reduction reactions. Many enzymes (polymerases) catalyze formation of chemical bond between individual monomers.

In general, when substrate monomers are converted to the (super)paramagnetic or radioactive higher molecular weight (MS)-containing product(s), such products can form via the enzyme-dependent polymerization and/or non-polymerization (e.g. binding to a macromolecule) processes described herein. This is summarized generally in Scheme 3 below:

Scheme 3

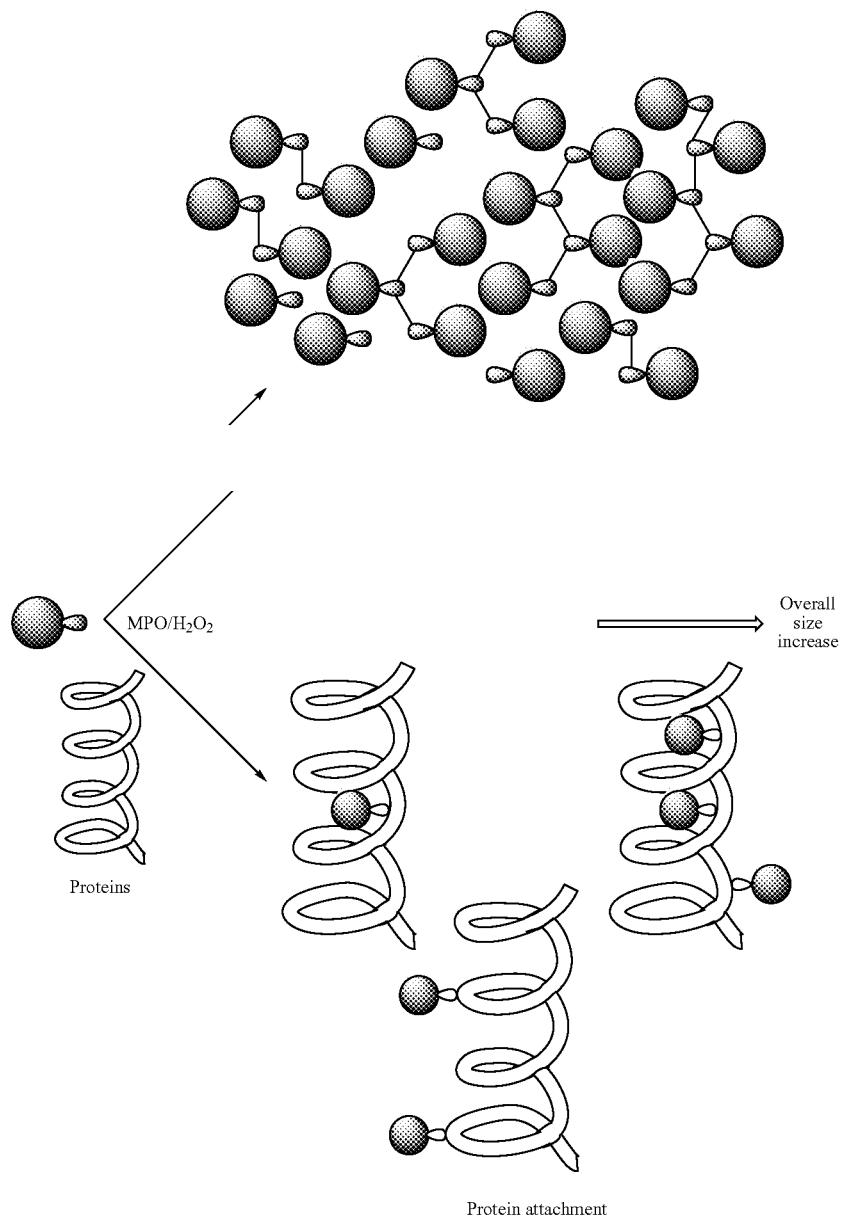

In some embodiments, the monomeric substrate can undergo polymerization to form a polymer having a plurality of monomeric substrate subunits, in which at least one pair of monomeric substrate subunits is cross-linked, and/or the monomeric substrate can undergo copolymerization with one or more macromolecules, which are substantially free of monomeric substrate subunits (e.g., a protein, e.g., a matrix protein), to form a copolymer having a plurality of monomeric substrate subunits and one or more macromolecules, in which at least one of the monomeric substrate subunits is cross-linked with another monomer subunit or the macromolecule (see, e.g., Scheme 4).

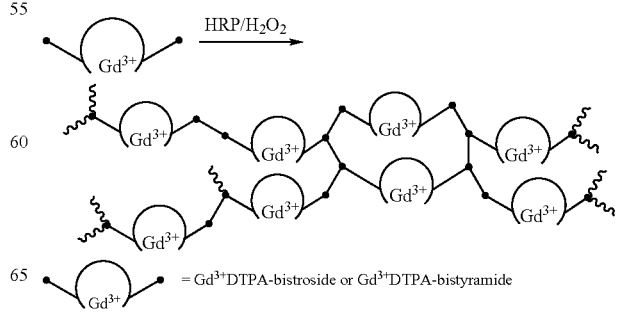

In certain embodiments, at least one pair (e.g., 2 pairs, 5 pairs, 10 pairs, 50 pairs, 100 pairs, or 1,000 pairs) of monomeric substrate subunits can be cross-linked. Each of the monomeric substrate subunits, including cross-linked monomeric substrate subunits, can be connected to one another by one or more chemical bonds (e.g., covalent bonds) between each of the constituent polymerizing moities.

In certain embodiments, at least one (e.g., 2, 5, 10, 50, 100, or 1,000) of the monomeric substrate subunits can be cross-linked with another monomer subunit or the macromolecule. Each of the monomeric substrate subunits, including cross-linked monomeric substrate subunits, can be connected to one another or to a macromolecule by one or more chemical bonds (e.g., covalent bonds) between each of the constituent polymerizing moities or between one or more constituent polymerizing moities and the macromolecule(s).

In some embodiments, the monomeric substrate can undergo polymerization or co-polymerization to form a relatively large polymer or co-polymer, respectively. In certain embodiments, the polymer or co-polymer can have a degree of polymerization (N) of at least about 2 (e.g., 3, 4, 5, 6, 7, 8, 9, 10, 20, 30, 40, 50, 100, 500, or 1,000). In certain embodiments, N can be determined using mass spectroscopy (e.g., MALDI-MS).

In some embodiments, the monomeric substrate can undergo polymerization or co-polymerization to form a polymer or co-polymer, respectively having a relatively large relaxivity (similarly, a monomeric substrate (or oligomer or polymer thereof) can bind to a macromolecule to form a product having a large relaxivity). In certain embodiments, the relaxivity can be at least about 10 mM-1s-1 (e.g., 15 mM-1s-1, 16 mM-1s-1, 17 mM-1s-1, 18 mM-1s-1, 19 mM-1s-1, or 20 mM-1s-1).

In certain embodiments, the polymer or co-polymer or macromolecule product can have a relaxivity that is greater (e.g., measurably greater, e.g., fitting measured T1 values according to the following expression: $(1/T_i)=(1/T_0)+r_{1p}[C]$; in which [C] is concentration expressed as mM, $T_i$ is the relaxation time in s and $r_{1p}$ is the relaxivity expressed in $mM^{-1}s^{-1}$) than that of the monomeric substrate at about 1.5 T and/or at about 0.47 T (e.g., from about 1.1 times greater to about 10 times greater, from about 1.1 times greater to about 5 times greater, from about 1.5 times greater to about 4 times greater, from about 1.7 times greater to about 3.7 times greater, or from about 2.4 times greater to about 3.7 times greater).

In certain embodiments, formation of the polymer or co-polymer can result in an increase in relaxivity of at least about 20% (e.g., 30%, 40%, 50%, 60%, 70%, 80%, or 90%).

In some embodiments, the monomeric substrate can undergo polymerization or co-polymerization to form a polymer or co-polymer, respectively, having a relatively low in vivo clearance rate (similarly, a monomeric substrate (or oligomer or polymer thereof) can bind to a macromolecule to form a product having a low clearance rate). In certain embodiments, the clearance rate of the polymer or co-polymer or macromolecule product is different than the clearance rate of the monomeric substrate. In certain embodiments, the polymer or co-polymer or macromolecule product can have a clearance rate that is less than the clearance rate of the monomeric substrate (e.g., the polymer or co-polymer or macromolecule product is cleared from the body at a rate that is slower relative to the rate that the monomeric substrate is cleared from the body). In certain embodiments, the polymer or co-polymer or macromolecule product can have a clearance rate that is at least about 3 times less (e.g., 4, 5, 6, 7, 8, 9, 10, 15, 20, 30, 40, 50) than the clearance rate of the monomeric substrate.

In some embodiments, the methods described herein can detect a target enzyme at a relatively low specific enzyme activity (U). In certain embodiments, U can be at most about 0.001 (e.g., 0.001, 0.004, 0.01, 0.04, 0.1, 0.4, 1, or 4). In general, the methods described herein can detect a target enzyme at a specific enzyme activity of from about 0.001 U to about 10 U (e.g., about 0.004 U to about 4 U, or about 0.04 U to about 4 U).

In certain embodiments, the monomeric substrate can undergo polymerization to form a polymer having a relatively low solubility. MALDI-TOF (mass spectrometry) of reaction products can indicate the formation of polymerized products (e.g., cross linked) with relatively high m/z parameter values.

In practicing the present invention, knowledge of the exact structure of the (super)paramagnetic or radioactive higher molecular weight (MS)-containing product(s) (e.g., polymerized or bound products) is not necessary. Without wishing to be bound by theory, it is believed that operation of the invention relates to the difference in atomic relaxivity between the monomeric substrate and the polymerized product, and does not depend on any particular structural arrangement of the subunit residues in the polymer or any of the other products. It is predicted that the polymerized products when formed are a mixture of numerous, differently branching (e.g., cross-linked) polymers.

Although the structural arrangement of the substrate residues in the polymerized product usually is not known, the range in the number of residues per polymer molecule can be determined in in vitro reactions, e.g., by size exclusion (gel filtration) chromatography. Such in vitro tests utilizing a particular substrate/enzyme combination can be employed to make useful predictions concerning the size of the polymers that will be formed in vivo. While the exact number of residues (or range of number of residues) per polymer is not critical, preferably the product mixture contains polymers whose length ranges up to 6, 7, 8, 10, 12, or 14 residues. In general, longer polymers are preferred. In certain embodiments of the invention, the monomeric substrate is chosen so that: (1) neither the monomer nor the resulting polymers display significant toxicity in the amounts used for imaging, and (2) both the monomer and the resulting polymer are excreted or biologically degraded within hours to days after the monomer is administered to a patient, although the monomer and the resulting polymer need not necessarily be degraded or excreted at the same rate.

Myeloperoxidase (MPO) Mediated Polymerizations

Vascular diseases, e.g., cardiovascular diseases, cerebrovascular diseases, and peripheral vascular diseases, carry relatively high mortality and morbidity. The process common to these diseases is atherosclerosis, e.g., the formation of unstable plaques, e.g., vulnerable plaques, that rupture and cause thromboembolic diseases and in some instances sudden death.

Advanced human atherosclerotic plaques contain relatively high numbers of neutrophils and other phagocytes expressing and actively secreting the heme-containing enzyme myeloperoxidase (MPO, EC 1.11.1.7). It has been shown that MPO is secreted in abundance by activated neutrophils and macrophages in vulnerable plaques and is implicated in mediating plaque rupture. MPO consumes hydrogen peroxide and generates hypochlorite, a pro-oxidant that contributes to erosion and rupture of atherosclerotic plaques. In addition to the catalysis of chloride oxidation to hypochlorite, MPO is capable of generating other highly reactive molecular species, e.g., chlorine, tyrosyl radicals, and aldehydes. These molecules participate in covalent modification, e.g., oxidation, of low density lipoproteins (LDLs), which exist in a variety of oxidized forms implicated in the pathogenesis of human atherosclerosis due to their role in foam cell formation. It has been shown that antibodies raised against hypochlorite-oxidized LDL react with numerous cells in atherosclerotic lesions, including monocyte/macophages, smooth muscle, and endothelial cells. Myeloperoxidase usually co-localizes with oxidized LDLs. Myeloperoxidase activity also has been linked to the activation of matrix metalloproteinase-7 pro-enzyme (MMP-7, matrilysin) suggesting that HOCl may regulate the activity of matrilysin in vivo, potentially inducing plaque rupture.

MPO is found in high abundance in vulnerable plaques and in culprit lesions. Within atherosclerotic plaques, it is believed that MPO uses $H_2O_2$ generated by NADPH oxidase to activate these agents. MPO can covalently modify and oxidize LDL to render it more atherogenic. MPO can also convert HDL to a form that diminishes its lipid scavenging effect. MPO oxidation products can activate matrix metalloproteinases to cause basement membrane rupture. Some studies have found that serum MPO levels predict cardiovascular risk in patients with acute coronary syndrome and chest pain. Furthermore, MPO-deficient humans appear to have decreased risk for cardiovascular diseases.

In general, the main reactions catalyzed by MPO can be described by the following set of reactions:

$$MPO+H_2O_2 \rightarrow MPO\text{-}I+H_2O \quad (1)$$

$$MPO\text{-}I+Cl^- \rightarrow MPO+HOCl \quad (2)$$

$$MPO\text{-}I+AH_2 \rightarrow MPO\text{-}II+AH\cdot \quad (3)$$

$$MPO\text{-}II+AH_2 \rightarrow MPO+AH\cdot \quad (4)$$

The pathways (2) and (3)-(4) both can result in the regeneration of the reduced enzyme, and could compete for the enzyme in the presence of both electron donor types (i.e., chloride anion and an aromatic electron donor $AH_2$). Without wishing to be bound by theory, the major pathway in vivo is believed to be pathway (2) which results in regenerated reduced MPO as a consequence of MPO-I reduction with two electrons of chloride anion. Due to the natural abundance of chloride, the probability of MPO-I reduction by a competing electron donor $AH_2$ would seem relatively low. However, it has been demonstrated previously that pathways (3)-(4) can out compete pathway (2) if a proper donor of electrons $AH_2$ is chosen. For example, it has been established that the kinetic constant of the MPO-I reaction with serotonin (5-hydroxytryptamine, 5-HT) at neutral pH is about 10 times higher than that of the reaction with chloride (see e.g., Dunford H B, et al., Kinetics of oxidation of serotonin by myeloperoxidase compounds I and II. *Biochem Cell Biol.* 1999; 77:449-57). Even in the presence of about 5,000 times higher excess of chloride over 5-HT the reaction of MPO-mediated oxidation of 5-HT could not be completely stopped (see, e.g., Dunford H B, et al., Kinetics of oxidation of serotonin by myeloperoxidase compounds I and II. *Biochem Cell Biol.* 1999; 77:449-57). We hypothesized that if 5-HT could be conjugated with a chelated paramagnetic cation, the oxidized products of the reactions (3) and (4) could form oligomers as a result of radical condensation (reaction 5):

$$nAH\cdot \rightarrow (AH)_n \quad (5)$$

Reaction (5) typically has relatively rapid kinetics and can yield dimers as well as polymers as final products (see, e.g., Michon, T., et al. Horseradish peroxidase oxidation of tyrosine-containing peptides and their subsequent polymerization: a kinetic study. *Biochemistry*. 1997; 36:8504-13 and Heinecke J W, et al., Dityrosine, a specific marker of oxidation, is synthesized by the myeloperoxidase-hydrogen peroxide system of human neutrophils and macrophages. *J Biol Chem.* 1993; 268:4069-77). These polymers can have a higher imaging signal than the initial monomeric substrate because the polymer is more paramagnetic than the monomer thus enabling the detection of the enzyme.

The reaction between serotonin and MPO in the presence of $H_2O_2$ is known to produce a distribution of oligomers with low N value. In general, the main product of the above reaction is a dimer. To test whether oligomerization of the monomeric substrates extend beyond N=2, $2Gd^{3+}$ was incubated with MPO (see Examples).

EXAMPLES

The invention is further illustrated by the following Examples. The Examples are provided for illustrative purposes only, and are not to be construed as limiting the scope or content of the invention in any way.

Example I

General

Figure 1B:
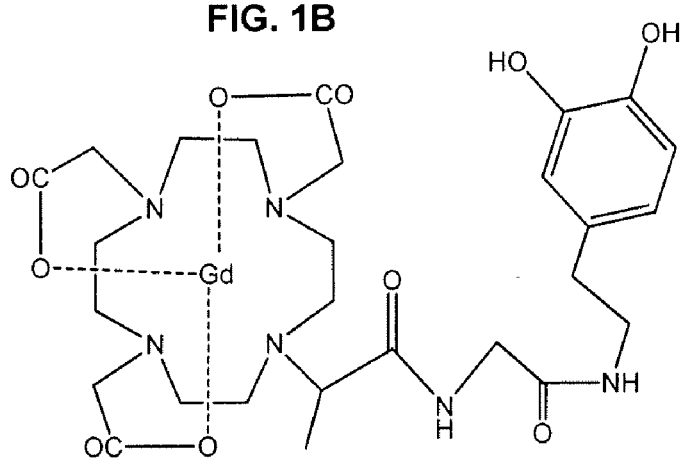
Figure 1C:
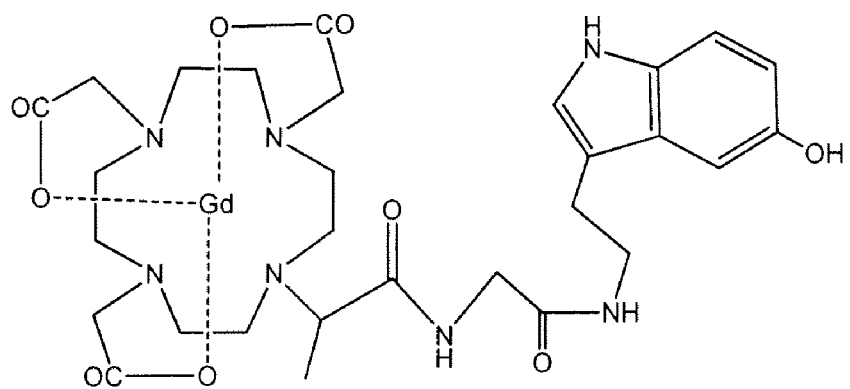

Three potential substrates for MPO were synthesized and evaluated by utilizing magnetic resonance and imaging techniques (see FIG. 1). Of these, an MPO-responsive "smart" probe was discovered consisting of a covalent conjugate of GdDOTA analog with serotonin (3-(2-aminoethyl)-5-hydroxyindole). The obtained probe (5-HT-DOTA(Gd)) was rapidly polymerized in the presence of human neutrophil MPO resulting in a 1.7-2 fold increase in proton relaxivity (R1 and R2). As a result, MPO activity could be imaged at 1.5T. Using a Matrigel™ tissue model system we observed the delineation of the interface between the gel and substrate solution suggesting the accumulation of MPO-converted polymerized 5-HT-DOTA(Gd) in the Matrigel™.

Our results revealed that 5-HT-DOTA(Gd) demonstrated relatively fast kinetics with MPO. As a result of the MPO-mediated polymerization, the resultant polymer product showed a relatively large increase in relaxivity, which was a larger increase when compared to that of tyramide-DOTA (Gd) in an equivalent amount of MPO (1.7 times for 5-HT-DOTA(Gd) versus 1.4 times tyramide-DOTA(Gd) at clinical imaging strength). In addition, 5-HT-DOTA(Gd) also has a relatively higher sensitivity to the amount of myleperoxidase present, showing visible imaging signal changes with 250 U of activity.

Our observation of a concentration dependence of relaxivity (R1 and R2) changes from the enzymatic conversion suggests that it may be possible to determine the relative amount of MPO present in atherosclerotic lesions for assessing the risk of rupture. For this purpose, despite the lower T1 changes found for the tyramide-DOTA(Gd) substrate compared with the 5-HT-DOTA(Gd) substrate at the same amount of MPO used, tyramide-DOTA(Gd) may offer a larger dynamic range to determine MPO activity (compare FIGS. 3A and 3B and 4A and 4B). While not wishing to be bound by theory, it is believed that for unstable plaques in vivo, the amount of MPO present would substantially exceed the amount needed to attain maximum substrate conversion for either substrate. In some embodiments, the slower kinetics of the tyramide-DOTA(Gd) can also limit its clinical utility.

Figure 8:
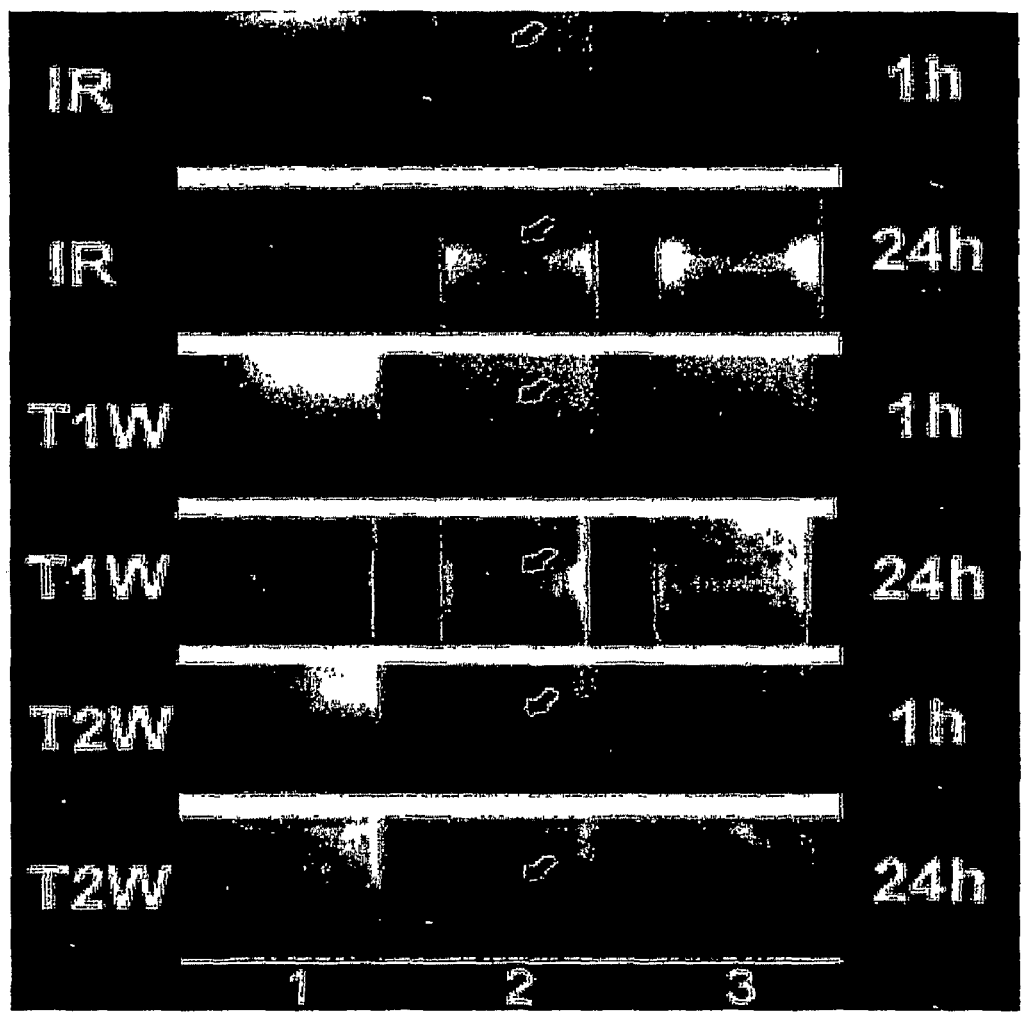
FIG. 8 is an image of 5-HT-DOTA(Gd) layered on top of Matrigel™ which contains MPO. The result is the delineation of the interface between the aqueous substrate layer and the Matrigel™ layer that increased over time (indicated by arrows in cell 2). No such delineation was observed in the control cell #1. Each cell contained 6 µg MPO in the gel and 650 nmol 5-HT-DOTA(Gd) solution on top of the gel, and in addition: 1—control, no glucose oxidase, 2—0.5 µg glucose oxidase, and 3—1 µg glucose oxidase. Imaging parameters: IR: TR=700 ms, TI=200 ms, TE minutes. T1W: TR=300, TE=9 ms. T2W: TR=300 ms, TE=200 ms.

Visible signal changes were detected for the 5-HT-DOTA (Gd) agent when it is oligomerized by MPO in aqueous solutions (see FIGS. 6A-6F and 7A-7F). We expanded these imaging experiments by using a tissue model made with Matrigel™ for determining that the substrates could delineate tissues containing MPO. Matrigel™ is a solubilized basement membrane preparation, which gels at room temperature to form a reconstituted biologically active material resembling the mammalian basement membrane. We tested this model with 5-HT-DOTA(Gd) in the presence with MPO and glucose oxidase supplying hydrogen peroxide. The results (see FIG. 8) revealed selective delineation of the margin of the Matrigel™. These findings are consistent with the accumulation of MPO-converted oligomers at the interface. The accumulation may be explained by larger molecular diameters of MPO-converted products which cannot diffuse rapidly in the Matrigel™. The MR signal intensity changes were visible soon after sample preparation, supporting the results of the kinetics experiment. The 24-hour delayed images showed a slight increase in the area highlighted by the enzyme-converted oligomers, consistent with slight interval diffusion of the oligomers in the Matrigel™.

There was visible signal change at the interface not only on T1-weighted, but also on T2-weighted spin echo as well as on inversion recovery (IR) images (FIG. 8) with the changes being more prominent on inversion recovery images. While not wishing to be bound by theory, these findings suggest that both post-contrast T1- and T2-weighted images can be useful to the delineation of tissues such as unstable plaques that contain MPO. In addition, optimized inversion recovery sequences may also be a sensitive method to detect MPO activity utilizing 5-HT-DOTA(Gd). That visible changes are seen on these different post-contrast sequences imply that in clinical imaging, an atherosclerotic lesion that changes signal characteristics on all three types of sequences has an abundance of enzymatically active MPO, and would therefore represent an unstable plaque that may rupture.

Example I-A

Substrate Synthesis

Synthesis of Glycylmethyl DOTA(Gd) Tyramide (T-DOT-AGd)

Tert-butyl ester of glycylmethylDOTA (tri tBu-10-(3-aza-4-carboxy-2-oxo-1-methyl-butane-1-yl)-1,4,7,10-tetraaza-cyclododecane-1,4,7-tris-acetic acid tert-butyl ester) was provided by Schering AG. Tyramidyl-glycylmethylDOTA, Gd salt was obtained as follows: a solution of carboxylic derivative: 10-(3-aza-4-carboxy-2-oxo-1-methyl-butane-1-yl)-1,4,7,10-tetraazacyclododecane-1,4,7-tris-acetic acid tert-butyl ester (GlyMetDOTA tri tBu) (I) 500 mg, 0.78 mmol), dicyclohexyl carbodiimide (193.64 mg, 0.94 mmol) and N-hydroxysuccinimide (179.54 mg, 1.56 mmol) in dimethylformamide (10 ml) at 0° C. in the presence of argon. The mixture was stirred for 48 hours, the precipitate was filtered and the filtrate was supplemented with tyramine (96.03 mg, 0.70 mmol). After being stirred for 2 hours at room temperature, the reaction mixture was combined with 50 ml of water and the crude product was extracted with $CH_2Cl_2$ (3×15 ml), washed with water (30 ml), dried over $MgSO_4$ and concentrated.

The crude product was treated with a deprotection solution consisting of 90% TFA for 2 hours. The carboxylic product was precipitated with diethyl ether to yield 420 mg (91%) of the corresponding DOTA-tyramide. Solid $GdCl_3$ (100.3 mg, 0.27 mmol) was added to a solution of DOTA-tyramide (110 mg, 0.18 mmol) in triethylammonium acetate (2 mL, pH=5). The mixture was stirred at room temperature for 8 hours and the product was crystallized at 4° C. in trimethylammonium acetate. The precipitate was washed with cold water to provide 101.3 mg (75% yield) of crystalline compound. LRMS (MALDI-TOF) calculated for $C_{27}H_{39}N_6O_9Gd$ $(M+H)^+$ 748.89. Found 749.96. The resultant crystalline product was determined to be pure by HPLC.

Synthesis of Glycylmethyl DOTA(Gd) 5-Hydroxytryptamide (5-HT-DOTAGd) and Glycylmethyl DOTA(Gd) Hydroxytyramide 5-hydroxytryptamide-DOTA(Gd) was obtained using the scheme above by substituting tyramide with serotonin (5-HT) or hydroxytyramide (dopamine). The final purification was achieved by using a Vydac C18 HPLC column eluted with a gradient of acetonitrile in water (10-80%). The peak fractions were pooled and T1 relaxation times of water in these fractions were measured. Fractions with short T1 were collected and tested using HRP reaction (see below). Gadolinium concentration in these fractions was approximated using GdDTPA as a standard.

Example I-B

Specific Activity of Myeloperoxidase

Myeloperoxidase was obtained from BioDesign Inc. Horseradish peroxidase (HRP) (type XII) was obtained from Sigma-Aldrich. The specific activities of myeloperoxidase and horseradish peroxidase were determined by UV/vis spectrophotometry on a Hitachi U3000 spectrometer, against guaiacol, and monitored at 470 nm according to the method of Klebanoff et al., Antimicrobial activity of myeloperoxidase. *Methods Enzymol.* 1984; 105:399-403.

Example I-C

Enzyme-Mediated Polymerization

Reactions with HRP and MPO were carried out at room temperature in the presence of 0.5-1 mM substrate dissolved in 0.5 ml PBS containing $H_2O_2$ (2 mM). Reaction was initiated by adding an aliquot containing the enzyme (either HRP or MPO) and vortexing. After at least a 30 min incubation period T1 was measured using inversion-recovery pulse sequence Bruker Minispec (Buker Analytics, North Bellirica Mass.) at 0.47 T (20 MHz). Size-exclusion HPLC of reaction products was performed on TSK G3000SWXL macroporous column (Supelco) eluted with 0.1 M triethylammonium acetate, pH 7.0 at 1 ml/min.

Example I-D

Kinetics

Kinetics of the samples were observed by measuring T1 and T2 at 0.47 T and 40° C. of the samples over at least a 24 hour period. At different time points, 1 M of sodium azide (final concentration=0.17 M) was added to stop the enzyme mediated reaction. The resultant progress curve was fitted with an empirical mathematical model and analyzed according to the Guggenheim method to obtain the pseudo-first-order rate constants (Guggenheim E A. *Philos. Mag.* 1926; 2:538).

Example I-E

MR Relaxation and Imaging

Standard 96-well plates were prepared and imaged on a 1.5 T whole body clinical General Electric Signa MRI scanner utilizing a standard 3 inch surface coil. Inversion recovery sequences were used to measure T1 relaxation and spin echo sequences were utilized to measure T2 relaxation. T2 weighted images were obtained with TR=5000 ms and TE=100 ms with a fast spin echo sequence. T1 weighted images were obtained with spin echo sequences with the following parameters: TR=100, 200, 350, or 500, TE=11. For the Matrigel™ experiments, a relatively T2 weighted image was obtained at TR=300 ms and TE=200 ms. Single-exponential models were used to obtain T1 and T2. The relaxivities were computed by normalizing relaxation rates to the concentration of gadolinium in each sample, obtained by inductive coupled plasma (ICP) analysis performed by Galbraith Laboratories.

Example I-F

Enzyme Activity and Substrates

The specific activity was measured using guaiacol oxidation by the enzymes. Specific activities were: 36,000 U/mg for horseradish peroxidase (HRP) and 7,900 U/mg for myeloperoxidase (MPO). Three substrates were synthesized using a protected DOTA analog as the chelating moiety for gadolinium: tyramide-DOTA(Gd), hydroxytyramide-DOTA (Gd), and 5-hydroxytryptamide-DOTA(Gd) (5-HT-DOTA (Gd). The structures of each candidate substrate is shown in FIG. 1.

Example I-G

Hydrogen Peroxide Concentration

Heinecke et al. disclosed that for tyrosine and MPO there is a dependence between the concentration of the tyrosine and the amount of hydrogen peroxide added (Heinecke J W, et al., Dityrosine, a specific marker of oxidation, is synthesized by the myeloperoxidase-hydrogen peroxide system of human neutrophils and macrophages. *J Biol. Chem.* 1993; 268:4069-77). According to Heinecke et al., for a 2 mM tyrosine solution, the amount of hydrogen peroxide that yielded the highest rate of reaction was 50 μM. To determine the optimal concentration of hydrogen peroxide needed, we successively added hydrogen peroxide to a 1.5 mM solution of 5-HT-DOTA(Gd), and measured T1 and T2 at 0.47 T after each aliquot of hydrogen peroxide was added. The results are summarized in FIG. 2, starting with 50 μM of hydrogen peroxide. We observed that T1 and T2 continued to shorten significantly until approximately 2 mM of hydrogen peroxide was added. Both T1 and T2 responded similarly to the amount of hydrogen peroxide added. Therefore, for the reactions in this work, we used 2 mM of hydrogen peroxide.

Example I-H

Figure 3A:
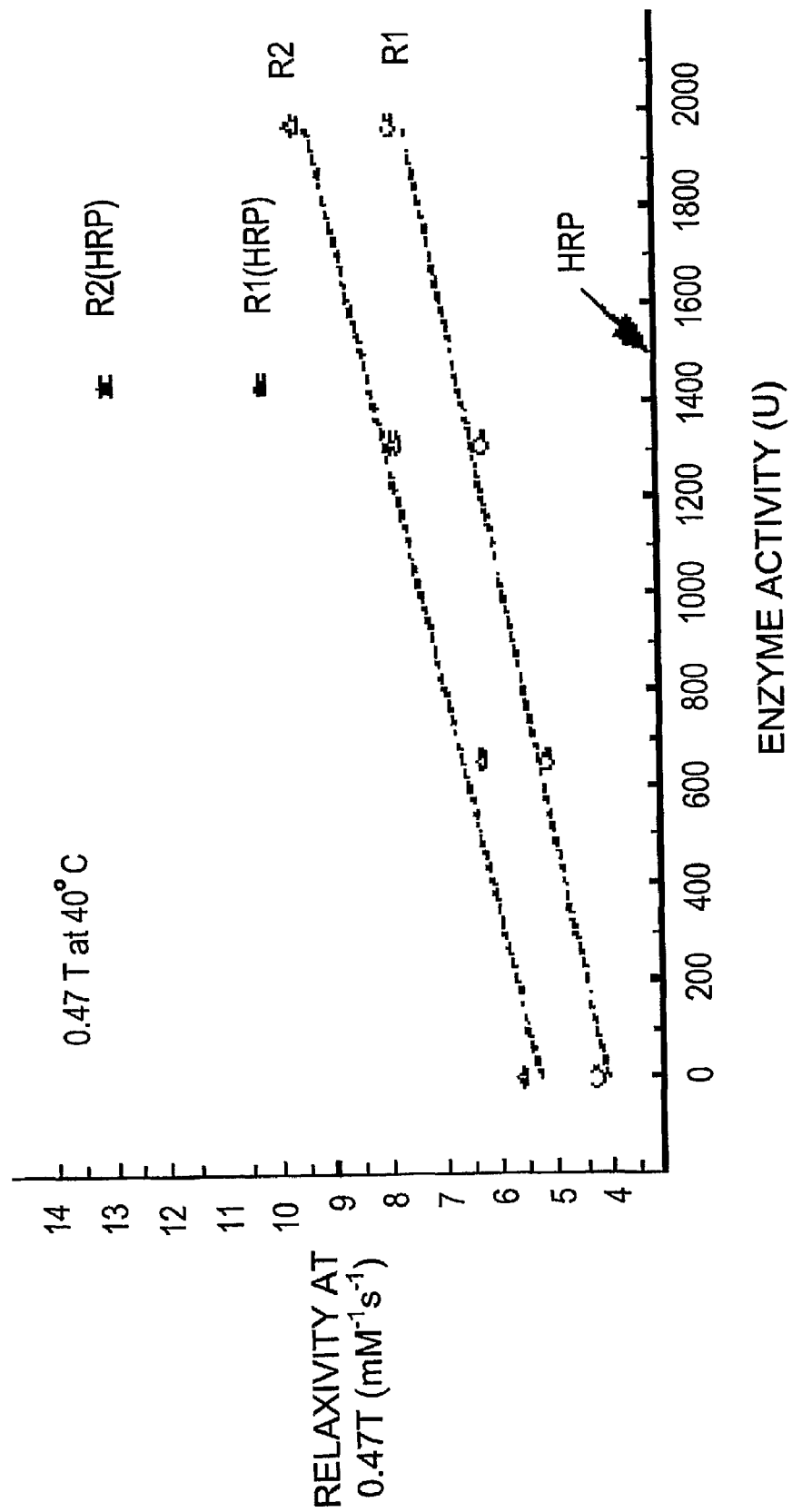
FIGS. 3A and 3B are graphical representations of the concentration dependence of tyramide-DOTA(Gd) relaxivity (R1 and R2) from myeloperoxidase activity in the reaction at 0.47 T (40° C.) and 1.5 T (25° C.), respectively. The second from the last point in the figures is the relaxivity achieved by horseradish peroxidase used as positive control (solid symbols, arrow). R1 is the longitudinal relaxivity, R2 is the transverse relaxivity.
Figure 3B:
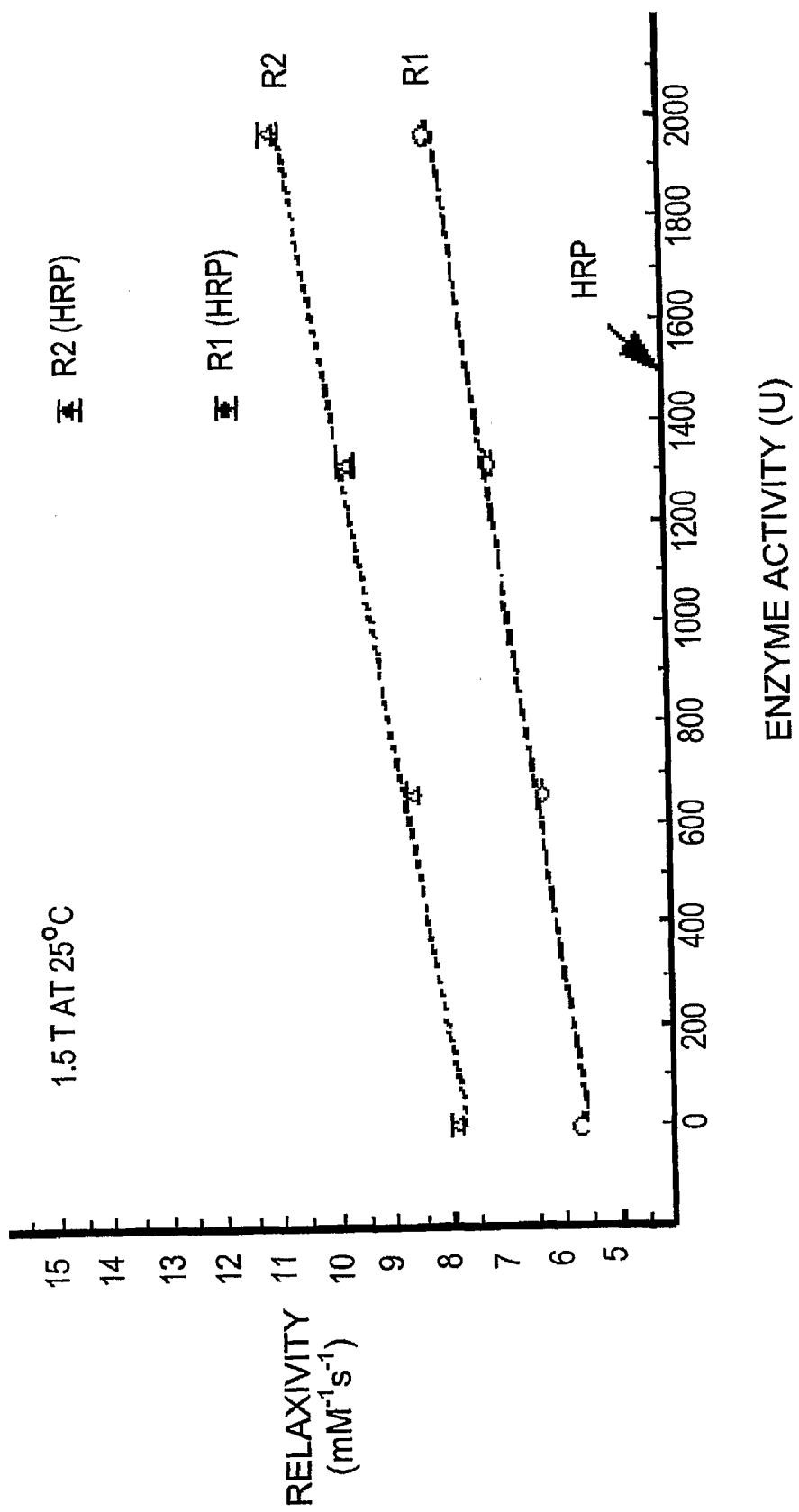
Figure 4A:
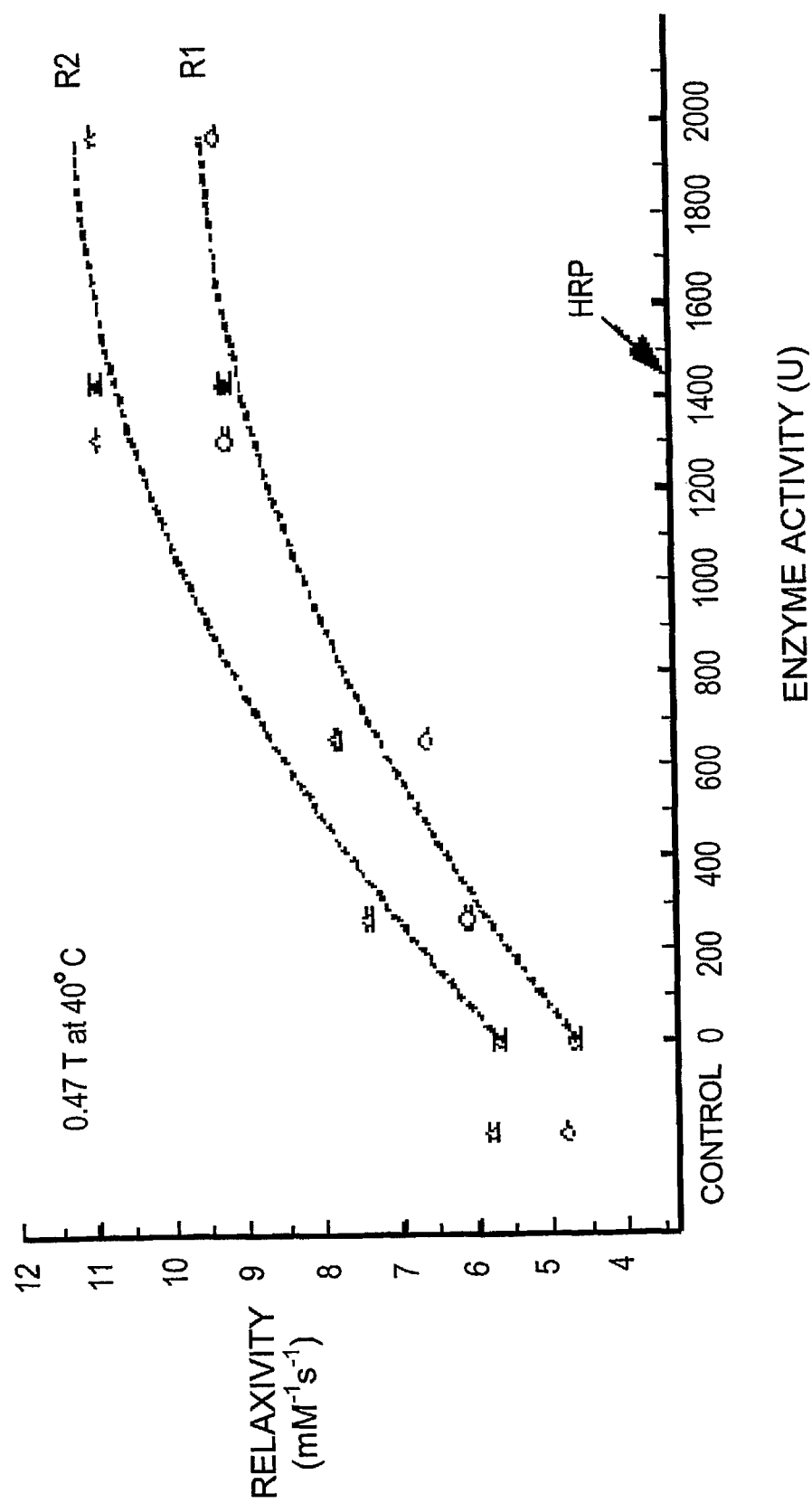
FIGS. 4A and 4B area graphical representations of the concentration dependence of 5-HT-DOTA(Gd) relaxivity (R1 and R2) from myeloperoxidase activity in the reaction at 0.47 T (40° C.) and 1.5 T (25° C.), respectively. The second from the last point in the figure is the relaxivity achieved by horseradish peroxidase as reference (solid symbols, arrow). R1 is the longitudinal relaxivity, R2 is the transverse relaxivity. Control is substrate with MPO but without $H_2O_2$.
Figure 4B:
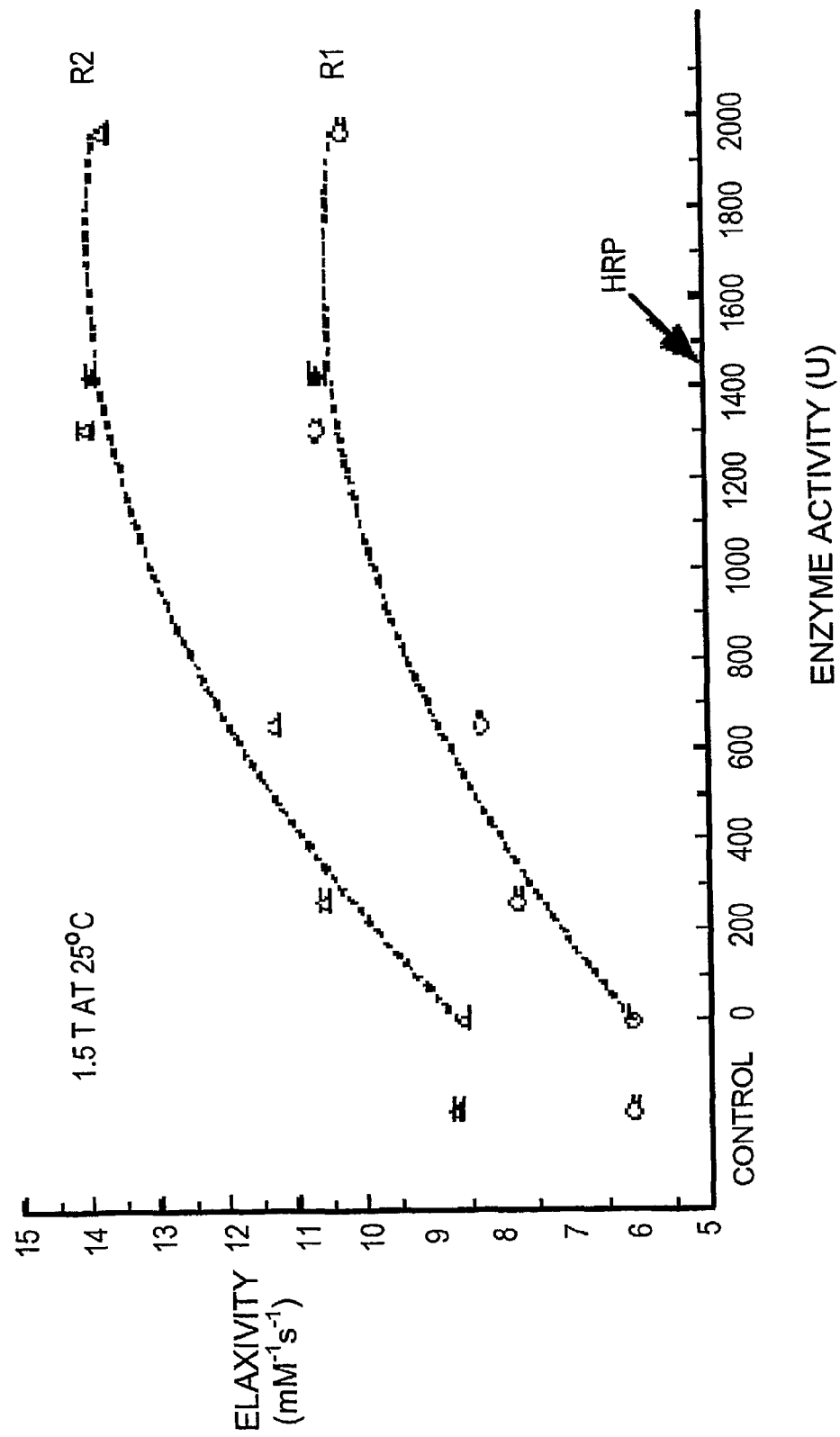

Relaxivity Increases Significantly from MPO-Mediated Reactions for 5-HT-DOTA(Gd) But not for the Other Substrates To determine the effect of myeloperoxidase on the substrates, we performed T1 and T2 relaxivity measurements in aqueous solutions, with and without MPO and hydrogen peroxide, at 0.47 T and 1.5 T (the results are summarized in FIGS. 3A and 3B for tyramide-DOTA(Gd) and FIGS. 4A and 4B for 5-HT-DOTA(Gd)). For reference, the two substrates were also reacted with HRP (solid symbols in FIGS. 3A and 3B and FIGS. 4A and 4B). Because of the relatively slow kinetics with MPO (described elsewhere), the reaction with hydroxytyramide-DOTA(Gd) did not result in a substantially significant relaxivity increase.

For 5-HT-DOTA(Gd), the maximum ratio of relaxivity increase between the MPO-converted product and the substrate is about 1.9-2 times at 0.47 T and about 1.6-1.7 times at 1.5 T for both longitudinal and transverse relaxivity (FIGS. 3A and 3B). This occurred at 1300-1400 U of enzyme activity. For comparison, with ~2000 U of activity, tyramide-DOTA(Gd) exhibited a lower relaxivity ratio of 1.7 times at 0.47 T and 1.4 times at 1.5 T. These results are in contrast to the reaction in horseradish peroxidase, where tyramide-DOTA(Gd) reached a relaxivity ratio of about 2.3 times at 0.47 T and about 2.1 times at 1.5 T (FIGS. 4A and 4B).

There is a concentration dependence of the relaxivities on the amount of MPO used in the reactions for both 5-HT and tyramide substrates. For the batch of MPO used in this work, for the 5-HT-DOTA(Gd) substrates, utilizing horseradish peroxidase (HRP) as a benchmark, at 10 μL of MPO (1.6 mg/ml) we reached 100% of the T1 shortening by 1 μL HRP (4 mg/ml). Approximately 70% of the HRP-mediated T1 shortening was observed at 250-650 U. However, for the tyramide-DOTA(Gd) substrate, only 70-75% of the HRP result was obtained at 2000 U. Assuming a linear response to the amount of MPO added until the effect plateaus estimated that >3000 U is needed to reach >90% of the T1 shortening seen with HRP for the tyramide-DOTA(Gd) substrate.

Example I-I

MPO Mediated Reactions Result in the Formation of Larger Complexes

Figure 5:
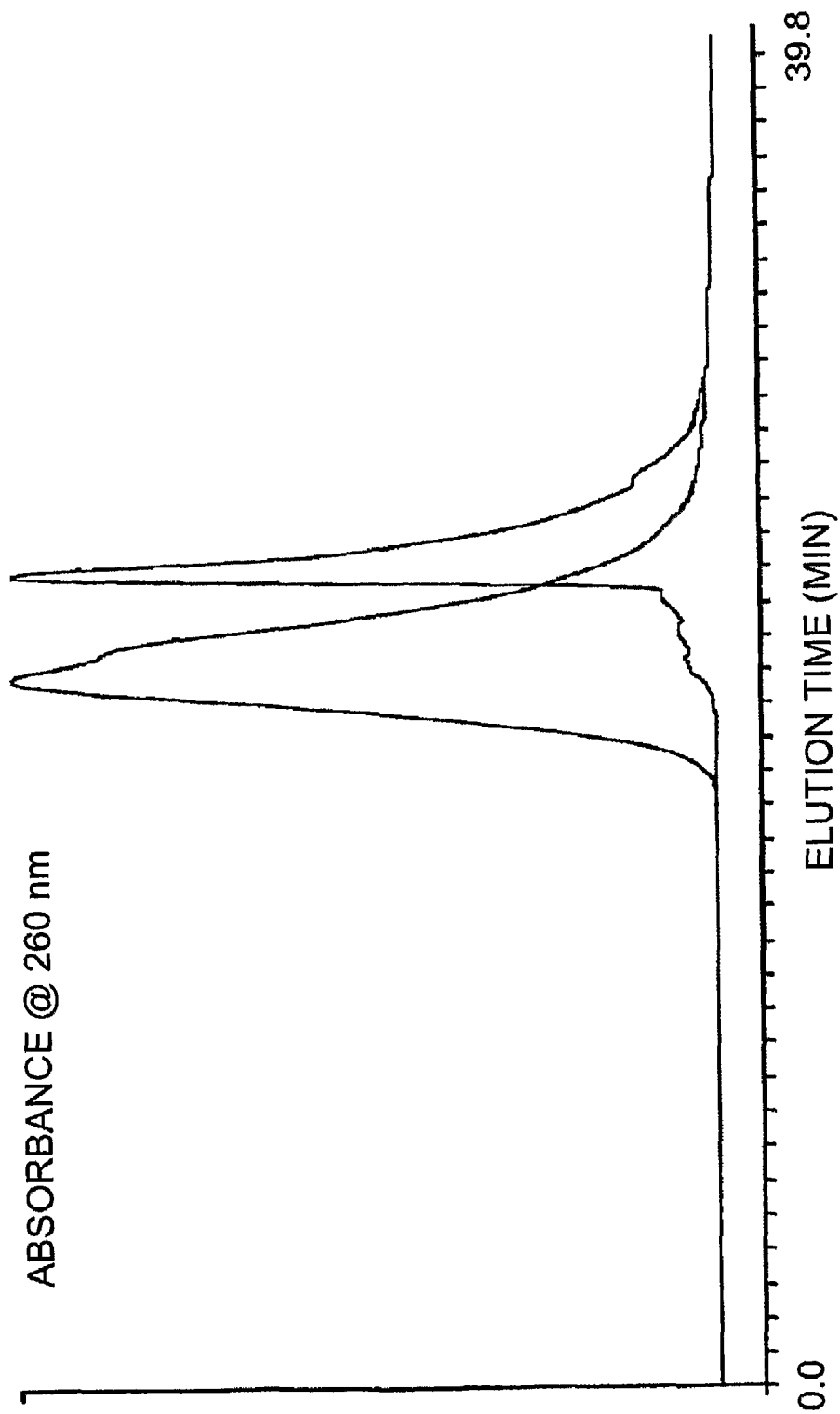
FIG. 5 is a size-exclusion HPLC trace (TSK G3000SWXL, Supelco) of 5-HT-DOTA(Gd) and the MPO-converted product. Peak 1, eluted at 20.8 minutes, is the MPO-converted substrate. Peak 2, eluted at 23.9 minutes, is the enzyme-free substrate 5-HT-DOTA(Gd).

To determine whether the shortening of the relaxation times was from the formation of larger complexes, e.g., oligomers, we performed size-exclusion HPLC on the 5-HT-DOTA(Gd) and its MPO-converted product. FIG. 5 shows the HPLC profile of the substrate 5-HT-DOTA(Gd) and the MPO-converted product superimposed on each other. The MPO-converted product was eluted first and distinct from the substrate, consistent with the formation of relatively larger oligomers. A similar profile was also obtained for the tyramide-DOTA(Gd) substrate and its MPO-converted product (not shown).

Example I-J

Kinetics of MPO-Mediated Reactions is Fast for 5-HT-DOTA(Gd)

An important property of a suitable substrate for an enzyme is the kinetics of enzymatic reaction. To determine the utility of the paramagnetic complexes as suitable substrates for human myeloperoxidase (MPO), we measured the pseudo-first-order rate constant of these substrates in MPO, and compared to the same substrates' reactions in Horse Radish Peroxidase (HRP) by monitoring the changes in relaxation time over time. Table 1 shows the pseudo-first-order rate constants for the substrates tested, in both HRP and MPO. The results shown were obtained using T1 measurements. T2 measurements yielded nearly identical results. The results are presented as mean±SD. N/A=not applicable.

TABLE 1

Pseudo first-order rate constants for the peroxidase mediated conversion of three different substrates.

| | HRP | MPO |
|---|---|---|
| 5-HT-DOTA(Gd) | $1.0 \times 10^{-2} s^{-1} \pm 3.8 \times 10^{-4} s^{-1}$ | $6.3 \times 10^{-3} s^{-1} \pm 1.3 \times 10^{-4} s^{-1}$ |
| Tyramide-DOTA(Gd) | $9.5 \times 10^{-3} s^{-1} \pm 2.5 \times 10^{-4} s^{-1}$ | $8.1 \times 10^{-4} s^{-1} \pm 1.5 \times 10^{-6} s^{-1}$ |
| Hydroxytyramide-DOTA(Gd) | $7.3 \times 10^{-4} s^{-1} \pm 1.2 \times 10^{-6} s^{-1}$ | N/A |

In HRP, tyramide-DOTA(Gd) has a pseudo-first-order rate constant of $9.5 \times 10^{-3}$ s$^{-1}$. However, in MPO, this substrate has a significantly slower kinetics with a pseudo-first-order constant that is an order of magnitude smaller than in HRP. For hydroxytyramide-DOTA(Gd), we found the kinetics to be substantially slower even in HRP, thus rendering it impractical for use with MPO or in vivo.

On the other hand, the pseudo first-order rate constant for 5-HT-DOTA(Gd) was found to be $1.0 \times 10^{-2}$ s$^{-1}$ for the HRP reaction and $6.3 \times 10^{-3}$ s$^{-1}$ for the MPO reaction, both of which are higher than those for tyramide-DOTA(Gd), suggesting that it may be a more desirable substrate for both HRP and MPO. For the 5-HT-DOTA(Gd) substrate, more than 80% of the final relaxation rate was obtained within the first 5 minutes, regardless of whether MPO or HRP was used. In addition, 5-HT has been shown to be able to out compete Cl$^-$ in vivo (see discussion elsewhere), and therefore it is expected that 5-HT-DOTA(Gd) would be a more suitable substrate for imaging MPO activity in vivo (see, e.g., Dunford H B, Hsuanyu Y. Kinetics of oxidation of serotonin by myeloperoxidase compounds I and II. *Biochem Cell Biol.* 1999; 77:449-57).

Example I-K

Imaging of 5-HT-DOTA(Gd) and its MPO-Converted Polymers can Report MPO Activity

Because of the relatively higher relaxivity and relatively faster kinetics with MPO, 5-HT-DOTA was chosen for further evaluation by imaging on a clinical 1.5 T MRI scanner. FIGS. 6A-6F and FIGS. 7A-7F illustrate the relative signal changes for typical T1- and T2-weighted images in aqueous solutions with MPO. As can be seen from the images, a visible signal difference was observed at 1.5 T between the MPO-converted product and the 5-HT-DOTA(Gd) substrate solutions with as little as 250-650 U present (see FIG. 6B). An approximately 40% signal difference was identified at 1300-2000 U (FIGS. 6C-6D), in keeping with the amount of relaxivity shortening found in the relaxation experiments ~70%).

We also designed a tissue model system with Matrigel™ to confirm that the substrates can delineate tissues containing MPO. Substrate was added on top of Matrigel™ containing MPO, and imaged at 1.5 T one hour after sample preparation (to ensure substrate conversion), and at 24 hours after sample preparation. Utilizing this tissue model system, and using glucose/glucose oxidase as the hydrogen peroxide generating system (peroxide is released by neutrophils in vivo), we observed an MPO-specific change in the MR signal (see FIG. 8) that is visible on T1-weighted, T2-weighted, and inversion recovery images, at 1 hour after sample preparation. The changes continued to increase over time, and at 24 hours, there is a 30% increase in the longitudinal relaxation rate (5.3 s$^{-1}$ to 6.9 s$^{-1}$) and a 20% increase in the transverse relaxation rate (8.8 s$^{-1}$ to 10.6 s$^{-1}$). Only the interface between the gel and the substrate solution demonstrated the signal change. No such change was identified in control systems where MPO was not present (not shown) or glucose oxidase was not present (see the first cell in FIG. 8).

Example II

Example II-A

Synthesis of Compounds 1 and 2

To a solution of freshly prepared DTPA-bis(anhydride) (0.357 g, 1 mmol) in dry DMF (30 mL) containing 2.2 eq. of dry Et$_3$N, tyramine or serotonin (2.2 eq.) were added and the mixture was stirred at room temperature for 48 hours. Upon completion, the solvent was removed in vacuo and the crude mixture was solubilized in 50 mL of 0.5M NaOH in water (50 mL). The basic solution was washed twice with 25 mL of methylene chloride and evaporated again to give a white powder. The powder was solubilized in MeOH and precipitated by slow acetone diffusion. This procedure was repeated three times to afford compounds 1 and 2 with yields of 47 and 58%, respectively.

Compound 1: $^1$H NMR (DMSO-d6, 400 MHz), δ (ppm): 2.61 (4H, t, J=7.2 Hz), 2.82 (4H, t, J=7.2 Hz), 3.06 (4H, m), 3.17 (4H, s), 3.19 (4H, s), 3.21-3.23 (4H, m), 3.39 (2H, s), 6.71 (4H, d, J=8.4 Hz), 7.02 (4H, d, J=8.4 Hz), 9.37-9.39 (2H, m). FAB-MS: 632, Compound 2: $^1$H NMR (DMSO-d6), δ (ppm): 2.70 (4H, t, J=7.6 Hz), 2.89 (4H, t, J=7.6 Hz), 3.10 (4H, m), 3.21 (4H, s), 3.24 (4H, s), 3.29-3.31 (4H, m), 3.46 (2H, s), 6.56 (2H, dd, J$_1$=6.4 Hz, J$_2$=2.2 Hz), 6.93 (2H, d, J=2.1 Hz), 7.02 (2H, d, J=2.1 Hz), 7.09 (2H, d, J=8.6 Hz), 8.42-8.45 (2H, m), 10.05 (2H, s). FAB-MS: 710, [M+H]$^+$.

Example II-B

Synthesis of the Gd(III) Complexes 0.08 mmol of either compound 1 or 2 was dissolved in 20 mL of distilled water containing 1% of citric acid. GdCl$_3$ anhydrous (1.05 eq.) was added and the solution brought to pH 7 with 0.5M NaOH solution. The mixture was stirred in dark and under argon for 72 hours. After this period, the mixture was lyophilized and resolubilized in 1.5 mL of distilled water. The complexes were isolated by HPLC (Protein and Peptide C-18 column, Vydac, s/n e950622-2-1) using a gradient of acetonitrile in water yielding 65 and 32% yield respectively.

Example II-C

Stock Solutions for Relaxivity Measurements

Stock solutions of compounds 1Gd and 2Gd were prepared by dissolving the corresponding complexes in DPBS buffer solution (pH 7.4) and were kept at −4° in the dark. Every stock solution was titrated by means of ICP-MS (Elemental Research Inc.).

Example II-D

MR Imaging and Relaxometry Parameters

Relaxation times at 0.47 T was obtained on a Bruker NMS-120 Minispec spectrometer using an inversion recovery sequence, with a TR=5$T_1$, and 15 TI points evenly spaced up to 5$T_1$.

Relaxation times at 1.5 T was measured on a 1.5 T GE Excite MR scanner utilizing an inversion recovery sequences with TR=2000 ms, TI=50, 75, 100, 150, 200, 250, 300, 350, 400, 500, 625, 750, 1000 ms. A fixed-size region of interest was drawn to obtain the signal intensity of the samples.

The data at 0.47 T and 1.5 T were fitted to the equation $I_x=I_0*(1-2e^{T1/T1})$ to obtain $T_1$, where I is the signal obtained at a certain time point TI, with $I_0$ (total signal or magnetization) and $T_1$ being fitted values.

MR imaging was performed on a 1.5 T GE Excite whole body MR scanner using a 3 inch surface coil. $T_1$-weighted images were obtained using a spin echo sequence with TR=500 ms, TE=11 ms, NEX=4.

Example II-E

Horseradish Peroxidase (HRP) Mediated Oligomerizations and

Magnetic Resonance Imaging

Horseradish peroxidase was purchased from Sigma as a lyophilized powder that was dissolved in PBS buffer (4 mg/mL) and its activity was measured using substantially the same the methods described by Klebanoff, S. J.; Waltersdorph, A. M.; Rosen, H. *Meth Enzymol.* 1984 Vol. 105, p 399-403.

Oligomerization of compounds 1$Gd^{3+}$ and 2$Gd^{3+}$ was achieved by incubating the desired solution (0.5 mL) of monomer with an excess of $H_2O_2$ 3% (2 μL) and HRP (1 μg≈4 Units) for 1 hour at 40° C. Both $T_1$ and $T_2$ were measured at two different field strengths: 0.47T and 1.5T, this last one using a clinical magnet (1.5 T Signa, GE).

The relaxivities of various polymerized products were measured using a minimum of four different gadolinium complex concentrations ranging from 2.5 mM to 0.01 mM. Horseradish peroxidase (HRP) was used in the proof-of-the-principle experiments. As used herein, the descriptors 1$Gd^{3+}$ and 2$Gd^{3+}$ refer to $Gd^{3+}$-chelated compounds 1 and 2, respectively. The synthesis of 1$Gd^{3+}$ and 2$Gd^{3+}$ are described in the Examples.

Relaxivity values of compounds 1$Gd^{3+}$ and 2$Gd^{3+}$ are shown in Table 2 under various tested conditions. While the first four rows show $T_1$ relaxivity values measured at 0.47T and at 1.5T (clinical magnet field strength) of the monomers in deionized water (measured pH=4.8) and in physiological conditions (in PBS: 10 mM sodium phosphate, 0.15 M NaCl, pH=7.4), the last two rows include relaxivities of the macromolecular aggregates resulting from enzymatic catalysis in phosphate buffered solution.

TABLE 2

Relaxivities of 1$Gd^{3+}$ and 2$Gd^{3+}$ in $H_2O$ (no HRP), PBS (no HRP), and $H_2O$/PBS (with HRP).

| Compound[a] | $r_{1p}$/mM$^{-1}$s$^{-1}$ (0.47T, 40°) | $r_{1p}$/mM$^{-1}$s$^{-1}$ (1.5T, 25°) |
|---|---|---|
| 1$Gd^{3+}$ ($H_2O$) | 4.6 | — |
| 2$Gd^{3+}$ ($H_2O$) | 4.5 | — |
| 1$Gd^{3+}$ (PBS) | 4.3 | 5.3 |
| 2$Gd^{3+}$ (PBS) | 4.3 | 5.1 |
| 1$Gd^{3+}$/HRP | 15.9 | 8.8 |
| 2$Gd^{3+}$/HRP | 10.5 | 6.6[b] |

[a]Brackets define the solvent used. When HRP is employed the solvent is PBS at pH = 7.4. $H_2O$ pH = 4.8.
[b]Fitting with three different concentrations due to precipitation at concentrations above 0.7 mM. $r^2$ = 0.98. For all the rest $r^2$ > 0.995.

As expected, based on the relaxivity values for DTPA or DTPA-bismonomethyl-amide at 0.47T, the relaxivities of compounds 1$Gd^{3+}$ and 2$Gd^{3+}$ were in the range of 4.3 mM$^{-1}$s$^{-1}$. On the other hand, all relaxivites showed an increase when the above monomers were treated with the enzyme. In this regard, the use of HRP resulted in a 3.7-fold increase in [$r_{1p}$] for 1$Gd^{3+}$ and 2.4-fold increase in [$r_{1p}$] for 2$Gd^{3+}$ at 0.47T and 40° C. The increase in [$r_{2p}$] was in the same range for both compounds (not shown). When measurements were made on a 1.5T clinical MRI unit at 25°, a 1.7 fold increase in relaxivity was observed for compound 1$Gd^{3+}$. The relaxivity of compound 2$Gd^{3+}$ could not be determined with high accuracy due to a linearity loss at high concentrations of 2$Gd^{3+}$ (~0.7 mM) when 1/$T_i$ values were plotted against Gd concentration. Nevertheless, a minimum increase of about 30% can be predicted from the obtained data (1.4-fold when concentrations below 0.5 mM were used for fitting). Similar results were obtained when transverse relaxivities [$r_{2p}$] were measured (not shown).

Figure 9A:
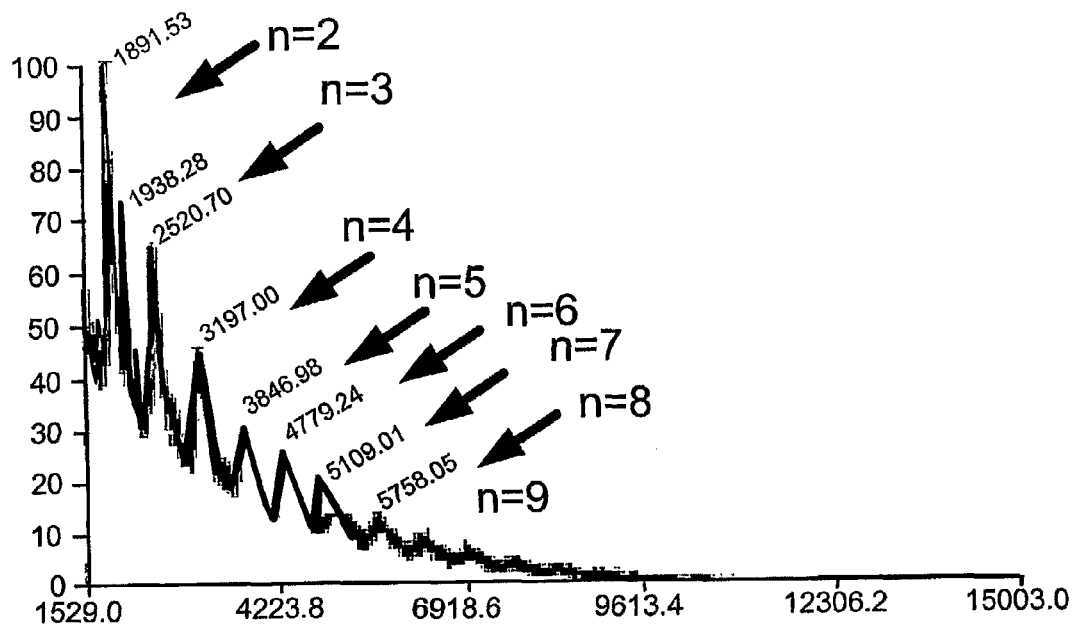
FIG. 9A is a MALDI-MS trace of the oligomerized Eu3+ salt of monomeric substrate 1. The charged species believed to correspond to oligomerized products having 2, 3, 4, 5, 6, 7, 8, or 9 as the degree of polymerization (N) are indicated with arrows on the trace.
Figure 9B:
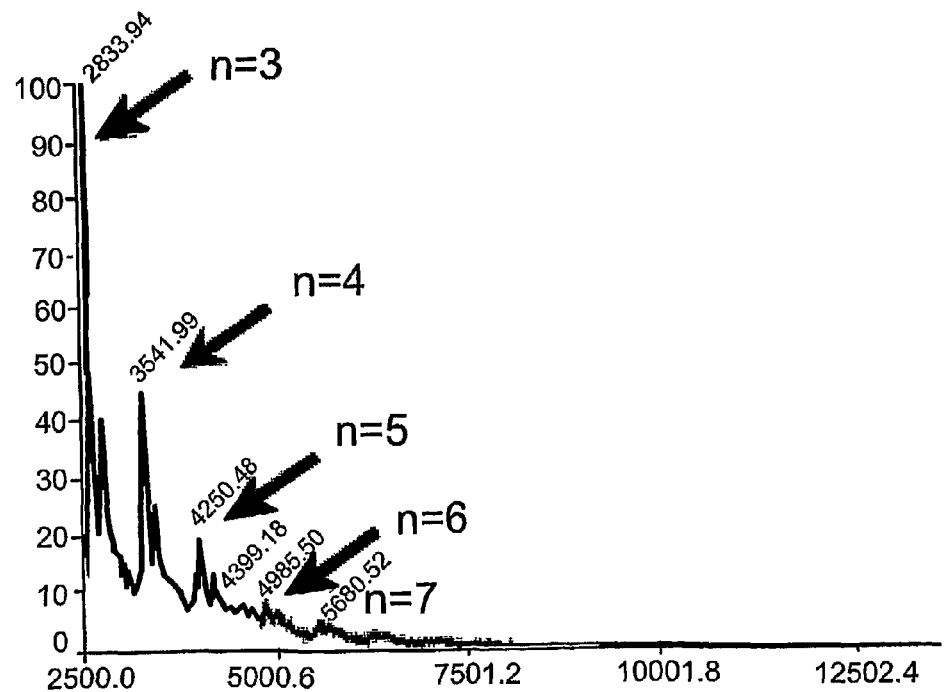
FIG. 9B is a MALDI-MS trace of the oligomerized Eu3+ salt of monomeric substrate 2. The charged species believed to correspond to oligomerized products having N=3, 4, 5, 6, or 7 are indicated with arrows on the trace.

While not wishing to be bound by theory, the above data can be explained by the formation of macromolecular aggregates, which have molecular rotational correlation times ($\tau_r$) that are longer than those of the monomeric substrates and, therefore, have higher relaxivities than those of the monomeric substrates. The observed non-linear dependence of relaxivity on concentration described above is believed to be associated with the formation of insoluble aggregates. To qualitatively demonstrate the formation of such aggregates, the mixture of the enzyme and $H_2O_2$ was added to concentrated solutions ($10^{-2}$M) of compounds 1$Gd^{3+}$ and 2$Gd^{3+}$. After incubating for a period of two hours at 40° C. followed by cooling to room temperature, we observed the initial formation of a gel-like product that gradually associated and precipitated. Similar experiments with Eu3+ salts of compounds 1 and 2 demonstrated the formation of oligomeric products with an average oligomerisation degree of 8 and 7, respectively, as shown by using MALDI-MS. The MALDI-MS traces of Eu3+ salts of compounds 1 and 2 are shown in FIGS. 9A and 9B, respectively.

In an embodiment, 2$Gd^{3+}$ at pH=7.4 (PBS buffer) has a minimum relaxivity increase of about 40% at 0.47T.

Figures 10A, 10B:
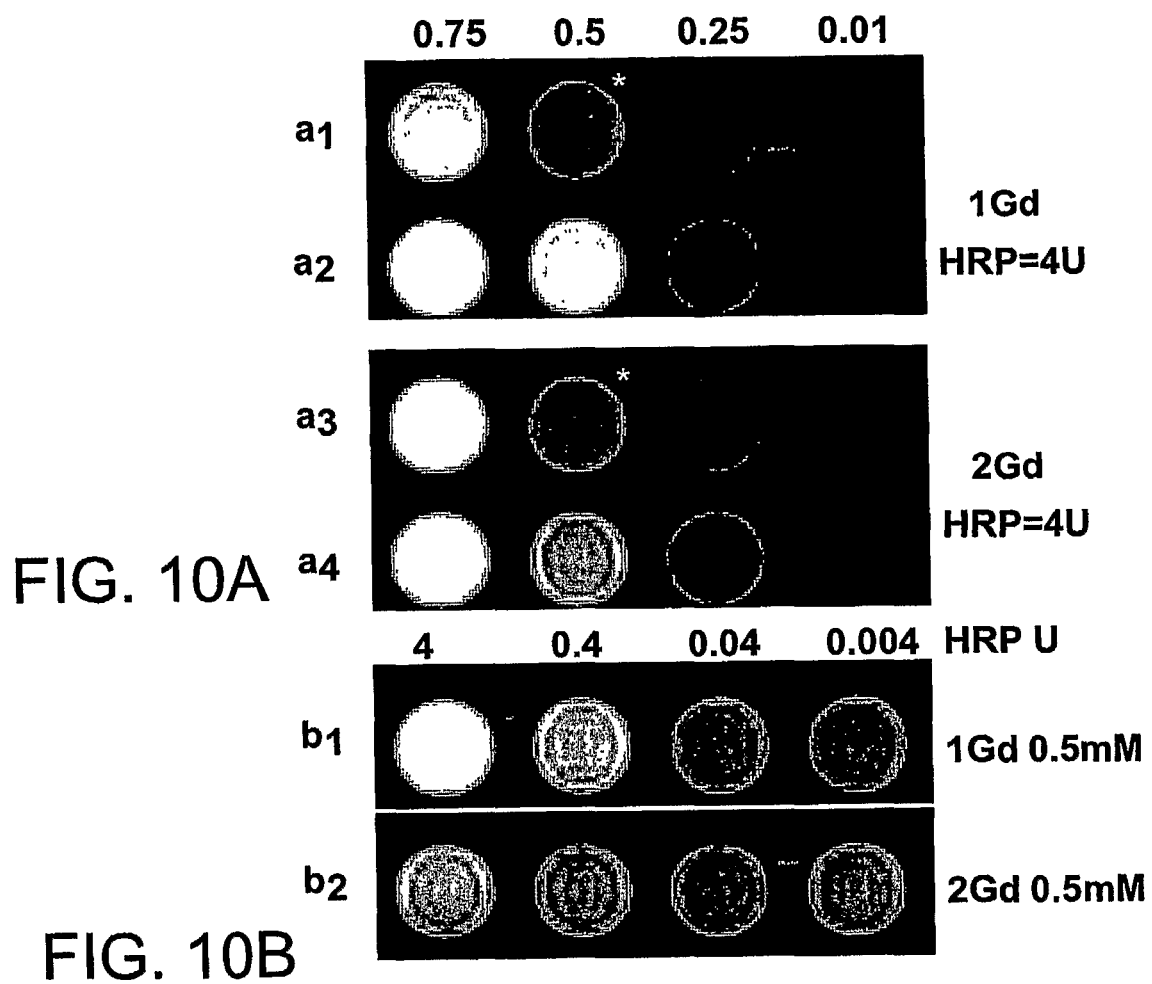
FIG. 10A is a $T_1$-weighted image of a 96-well immunoanalysis plate fragment (4×4 wells) showing a $T_1$ map of compounds $1Gd^{3+}$ and $2Gd^{3+}$ acquired at 1.5T. Rows $a_1$ in FIG. 10A contained (from left to right) 0.75, 0.5, 0.25, and 0.1 mM $1Gd^{3+}$ (300 μL) in DPBS, respectively. Samples in the row $a_2$ contained the same concentrations as above plus a fixed amount of HRP (4 units). Rows $a_3$ and $a_4$ were prepared as rows $a_1$ and $a_2$ respectively, but using compound $2Gd^{3+}$.
FIG. 10B is a $T_1$-weighted image well plate layout containing a fixed concentration of $1Gd^{3+}$ (0.5 mM, row $b_1$) and $2Gd^{3+}$ (0.5 mM, row $b_2$) supplemented with different HRP amounts (from left to right: 4, 0.4, 0.04, 0.004 U).

Further, a $T_1$-weighted image of a 96-well immunoanalysis plate fragment (4×4 wells) that contained 1$Gd^{3+}$ and 2$Gd^{3+}$ solutions was obtained to assess the contrast properties of the enzyme substrates in an MR imaging set-up at clinically relevant field strength (FIG. 10A). Rows $a_1$ in FIG. 2A contained (from left to right) 0.75, 0.5, 0.25 and 0.1 mM 1$Gd^{3+}$ (300 μL) in DPBS, respectively. Samples in the row $a_2$ in FIG. 2A contained the same concentrations as above plus a fixed amount of HRP (4 units). Rows $a_3$ and $a_4$ in FIG. 10A were prepared as rows $a_1$ and $a_2$ respectively but using compound $2Gd^{3+}$. The corresponding relaxivities measured are listed in Table 1.

FIG. 10A demonstrates predicted differences in MR signal intensity between the enzyme-containing and the enzyme-free substrate solutions, i.e., samples in the rows $a_2$ and $a_4$ show a net difference in signal when compared with the corresponding samples in rows $a_1$ and $a_3$ where no enzyme was used. The observed higher contrast is believed to be due to a 70% and 30% increase in relaxivity in the presence of peroxidase for compounds $1Gd^{3+}$ and $2Gd^{3+}$, respectively.

To estimate the detection limit of these sensor substrates, a new well plate layout containing a fixed concentration of $1Gd^{3+}$ (0.5 mM, row $b_1$) and $2Gd^{3+}$ (0.5 mM, row $b_2$) supplemented with different HRP amounts (from left to right: 4, 0.4, 0.04, 0.004 U) was imaged (FIG. 10B). The results of the this experiment are summarized in Table 3. The use of 4 U/mL of enzyme yielded a decrease in $T_1$ by 50 and 25% for compounds $1Gd^{3+}$ and $2Gd^{3+}$, respectively. Detectable decrease could be seen at enzyme specific activity levels as low as 0.04 U/mL. In this case the decrease was measured to be 15% for compound $1Gd^{3+}$ and 12% for compound $2Gd^{3+}$. In general, the use of lower enzyme activities did not yield any further improvement.

TABLE 3

HRP effect over T1 at C = 0.5 mM for $1Gd^{3+}$ and $2Gd^{3+}$

| HRP (U) | $T_1$-$1Gd^{3+}$ (ms) | $T_1$-$2Gd^{3+}$ (ms) |
| --- | --- | --- |
| 0 | 316 | 339 |
| 4 | 211 | 271 |
| 4 10-1 | 229 | 278 |
| 4 10-2 | 274 | 303 |
| 4 10-3 | 321 | 331 |

Besides the expected variations in measured relaxivity associated with differences in field strengths, the differences imaged thus far could be explained in terms of different degrees of polymerization/cross-linking due to variations in enzymatic activity and different stability of the intermediate radicals (intra-radical association kinetics is predicted to be diffusion limited). These differences in aggregation, also led to different solubility patterns along the different wells. This resulted in a loss of linearity of the dependence between relaxation time/concentration in row $a_4$ where turbidity could be observed (well 1, conc.=0.75 mM, 4 U HRP) during the course of the measurement. Those inhomogeneities proved to be more striking when $T_2$-weighted images were acquired (not shown) since paramagnetic precipitates cause strong magnetic field inhomogeneities.

Example II-F

MPO-Mediated Oligomerizations and Magnetic Resonance Imaging

Myeloperoxidase was purchased from Biodesign Int. and was used as received, activity was measured as described by Klebanoff, S. J.; Waltersdorph, A. M.; Rosen, H.; *Methods in Enzymology*. Vol. 105, p 399-403.

Figure 11:
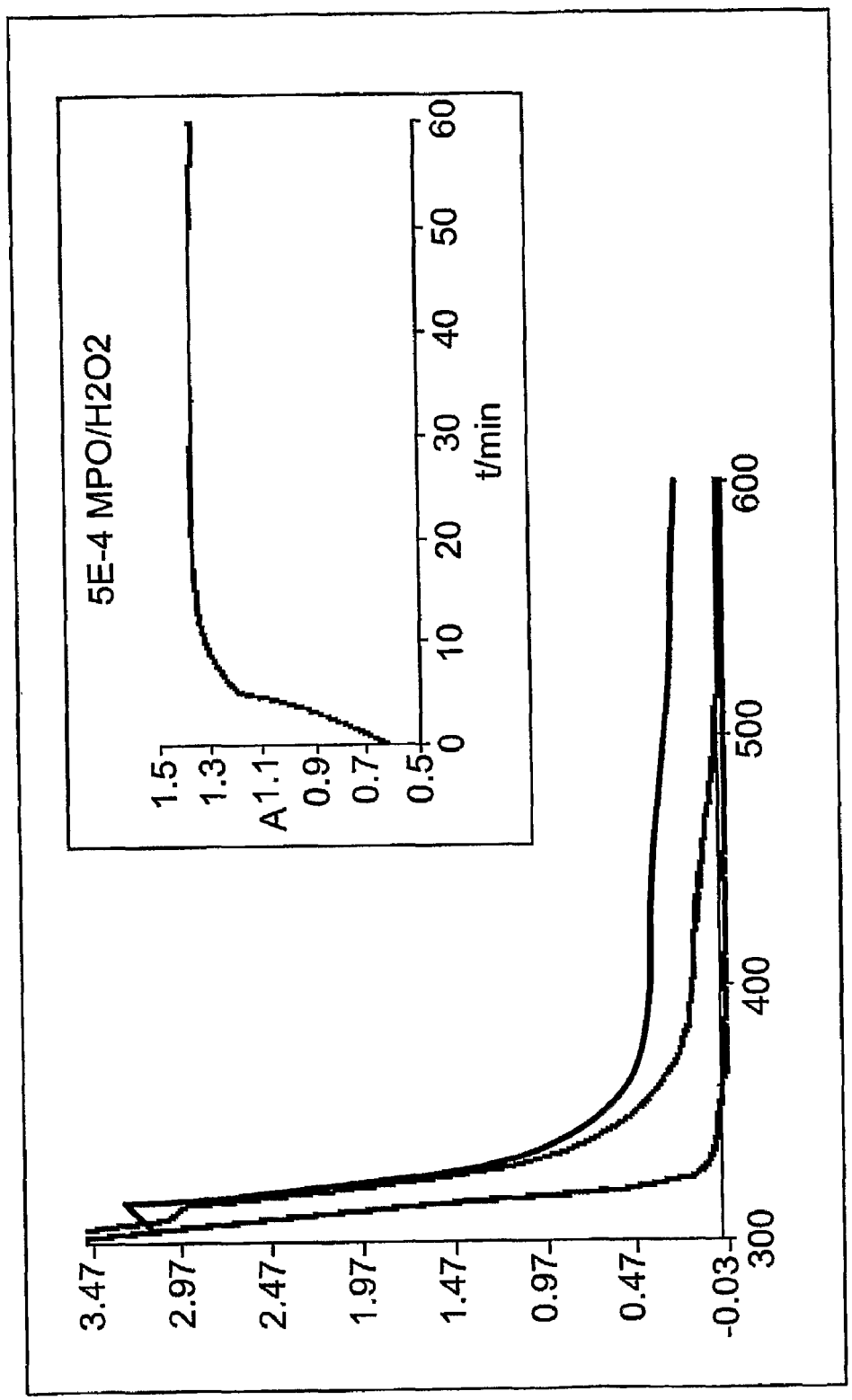
FIG. 11 shows a trace of the UV-measured conversion of $Gd^{3+}2$ upon the addition of $MPO/H_2O_2$: No enzyme (black), 20 minutes after addition (red), 24 hours after addition (yellow). Inset shows the kinetics followed by absorbance at 340 nm.
Figure 12A:
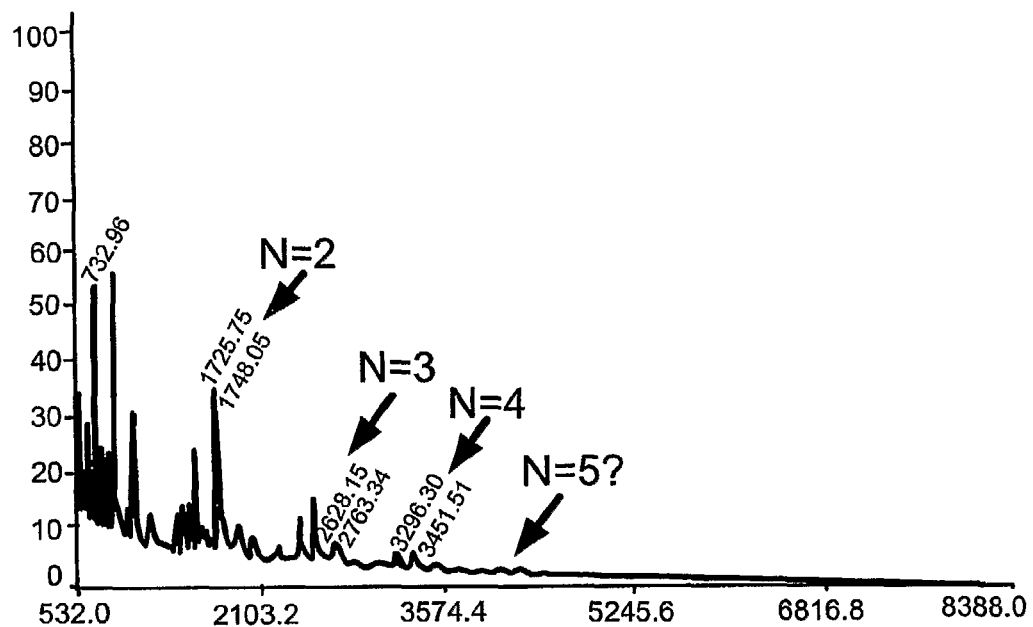
FIG. 12A is a MALDI-MS trace of the oligomerized Gd3+ salt of compound 2. The charged species believed to correspond to oligomerized products having N=2, 3, 4, and 5 are indicated with arrows on the trace.
Figure 12B:
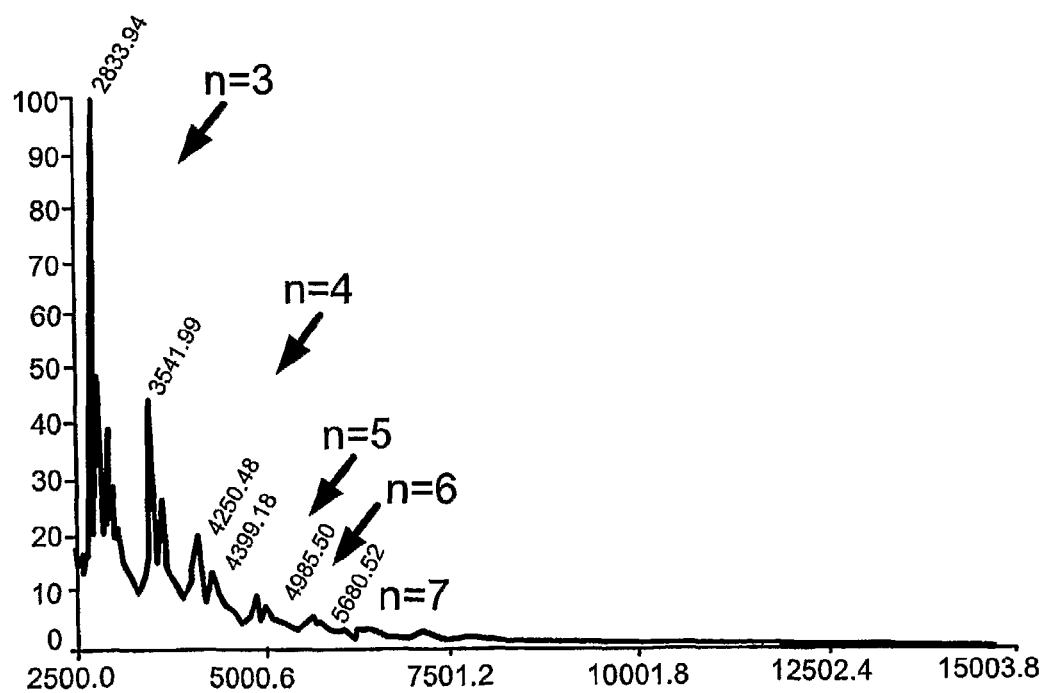
FIG. 12B is a MALDI-MS trace of the oligomerized Eu3+ salt of compound 2. The charged species believed to correspond to oligomerized products having N=3, 4, 5, 6, and 7 as the degree of polymerization (N) are indicated with arrows on the trace.
Figure 13A:
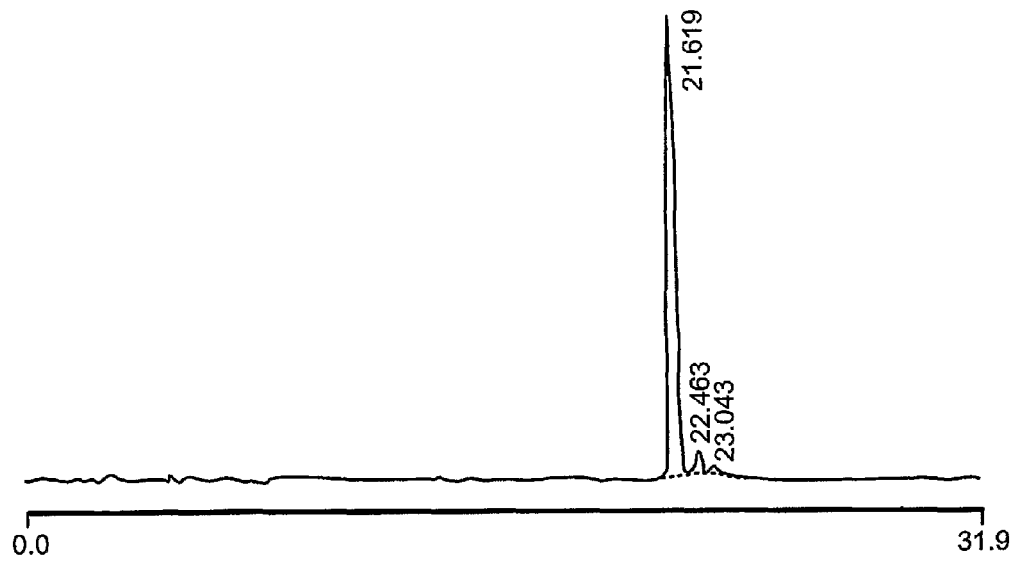
FIG. 13A is an HPLC trace of a reaction mixture containing Gd3+ salt of compound 2 before addition of MPO.
Figure 13B:
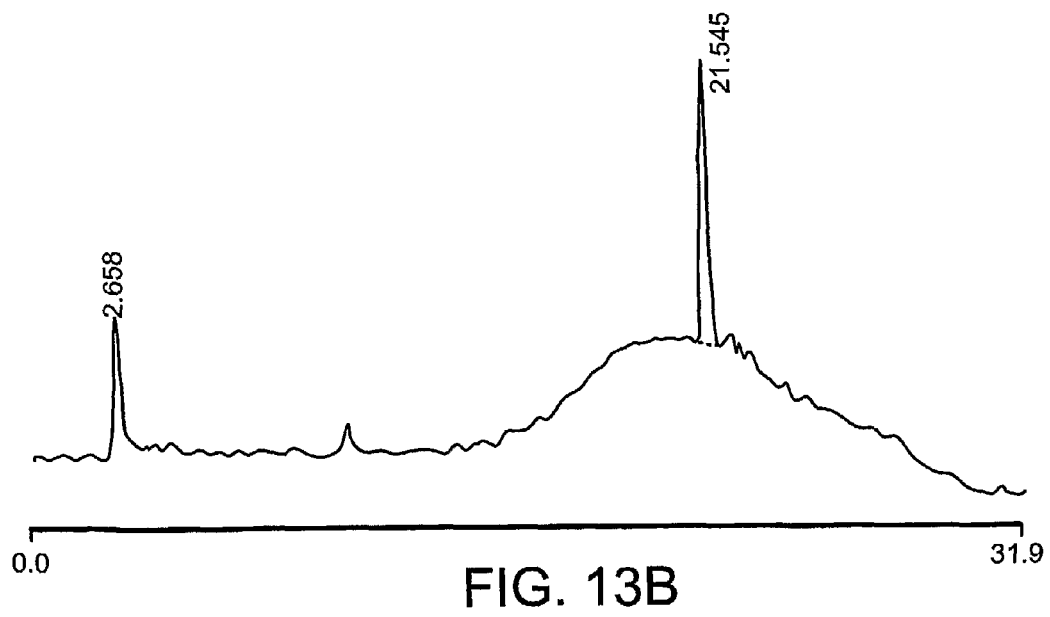
FIG. 13B is an HPLC trace of a reaction mixture containing Gd3+ salt of compound 2 after addition of MPO. Intensities, in arbitrary units, for the peaks at 21.6 minutes and 21.5 minutes, are 1 and 0.05 respectively. Conversion is 99.5%.

We incubated 0.6 mL of a solution $10^4$M of $Gd^{3+}2$ at pH=7.2/25° with 4 units of MPO and an excess of $H_2O_2$ for 90 minutes. As shown in FIG. 11, monitoring of UV spectra of the reaction mixture revealed the appearance of new absorptions beyond 300 nm where the monomer does not absorb. The intensity of these new bands increased for a period of about 90 min, and that 90% of the change could be observed within first 30 min. The reaction was quenched by freezing the mixture in liquid $N_2$. As shown in FIG. 12A, MALDI-MS data obtained for oligomerized $Gd^{3+}2$ demonstrated the presence of several species corresponding to N=1-4. However, higher N value species were undetectable. Similar experiments with the Eu3+ salt of compound 2 demonstrated the formation of higher oligomeric products (see FIG. 12B). As shown in FIGS. 13A and 13B, the HPLC analysis of the mixture showed a broad distribution of reaction products if compared with the initial substrate.

After we proved limited oligomerization of $2Gd^{3+}$ in the presence of MPO/$H_2O_2$, we tested the effects of this oligomerization on the relaxivity of the monomeric substrate. Four solutions with concentrations ranging from $10^{-4}$ to $10^{-3}$ where separately incubated as above and the T1 value were measured at 0.47T using standard inverse recovery sequence. The fitting of these values, following published procedures, yielded a $r_1$=5.9 mM$^{-1}$s$^{-1}$. This value suggests an increase of r1 by 37% if compared with the initial substrate. For longer incubation times, no linear correlation of T1 from Gd concentration could be obtained due to the precipitation of CA at millimolar concentrations. Lower relaxivity increase (32%) was observed when the activity of the enzyme was lowered to 1 unit.

Figure 14:
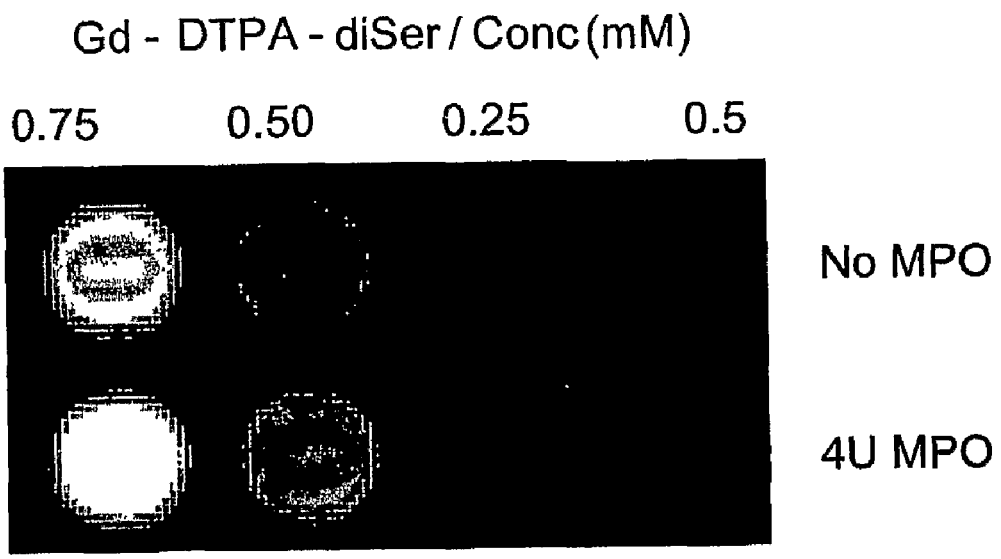
FIG. 14 is a $T_1$-weighted image of a 96-well immunoanalysis plate fragment (4×4 wells) showing a $T_1$ map of compound $2Gd^{3+}$ acquired at 1.5T. Row 1 contained 0.3 mL Gd-DTPA-diSer solutions at pH 7.2. Row 2 included the samples at the same concentrations and 4 units of MPO and 2 μL of a 3% of aqueous $H_2O_2$.

Further characterization of r1 effects modulated by MPO was accomplished by using a 4×2 well plate array of samples prepared as shown in FIG. 14: Row 1 contained 0.3 mL Gd-DTPA-diSer solutions at pH 7.2; Row 2 included the samples the same concentrations and 4 units of MPO and 2 μL of a 3% of aqueous $H_2O_2$. Fitting the $T_1$ values of the wells in row 1 afforded $r_1$ of 4.7 mM$^{-1}$s$^{-1}$. The higher $T_1$ values measured in the wells of row 2 did not show linear dependence from concentration. In this case, we observed precipitation of insoluble products during the MRI scan. The fitting of the values measured in other 3 wells, the relaxivity was 5.5 mM$^{-1}$s$^{-1}$. The latter value shows a minimum increase of 17% over the range $10^{-4}$ to 5 $10^{-4}$. The above results suggest extensive cross-linking of the monomeric substrate derived products upon the oxidation during the course of active MPO regeneration.

Figure 15:
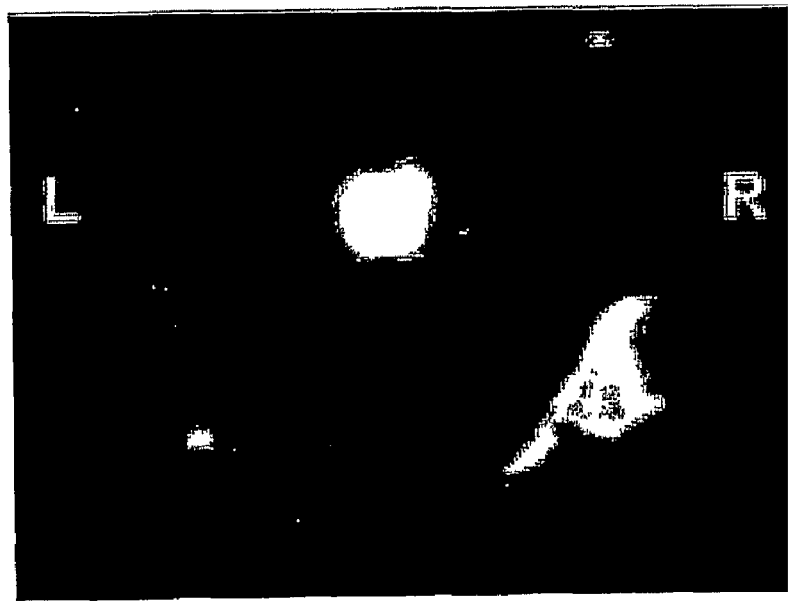
FIG. 15 is a T1 weighted image of MPO mouse model. The animals were injected with $2Gd^{3+}$ at the dose 0.3 mM/kg.
Figure 16B:
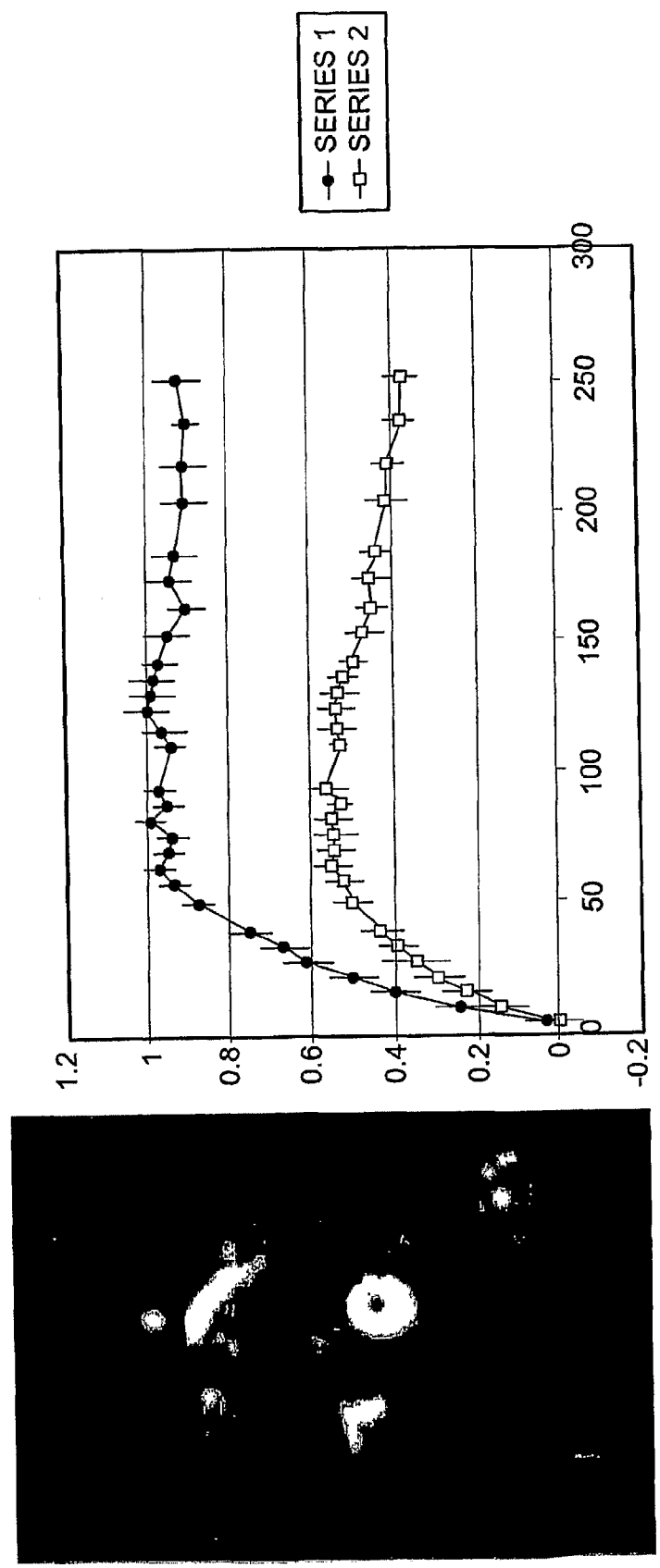
FIG. 16B is a T1 weighted image of an MPO mouse model after injection with serotonin-DOTA-$Gd^{3+}$ complex. The maximum relative CNR(CNR(right)/CNR(left)) ratio is 1.72.
Figure 16C:
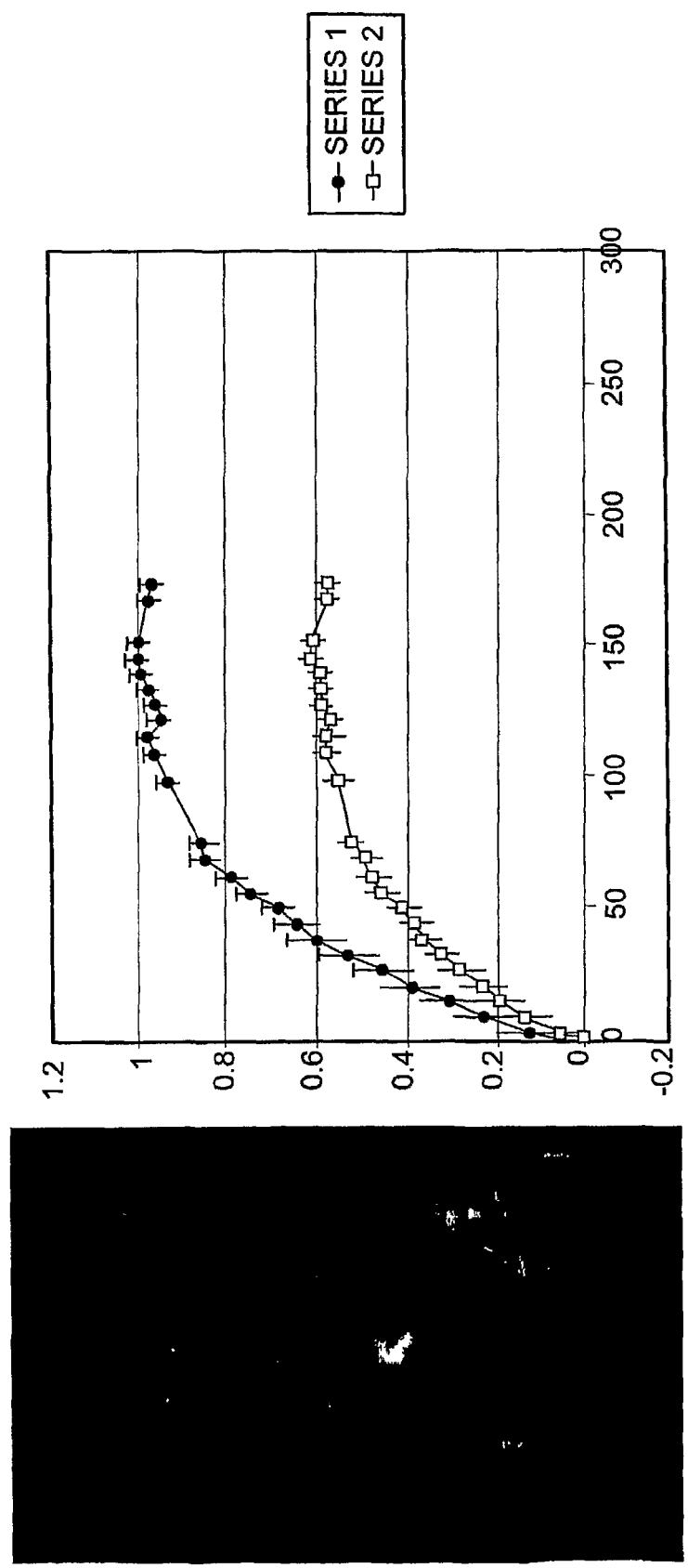
FIG. 16C is a T1 weighted image of an MPO mouse model after injection with $2Gd^{3+}$ complex. The maximum relative CNR ratio is 1.72 and is reached within 180 minutes.
Figure 16D:
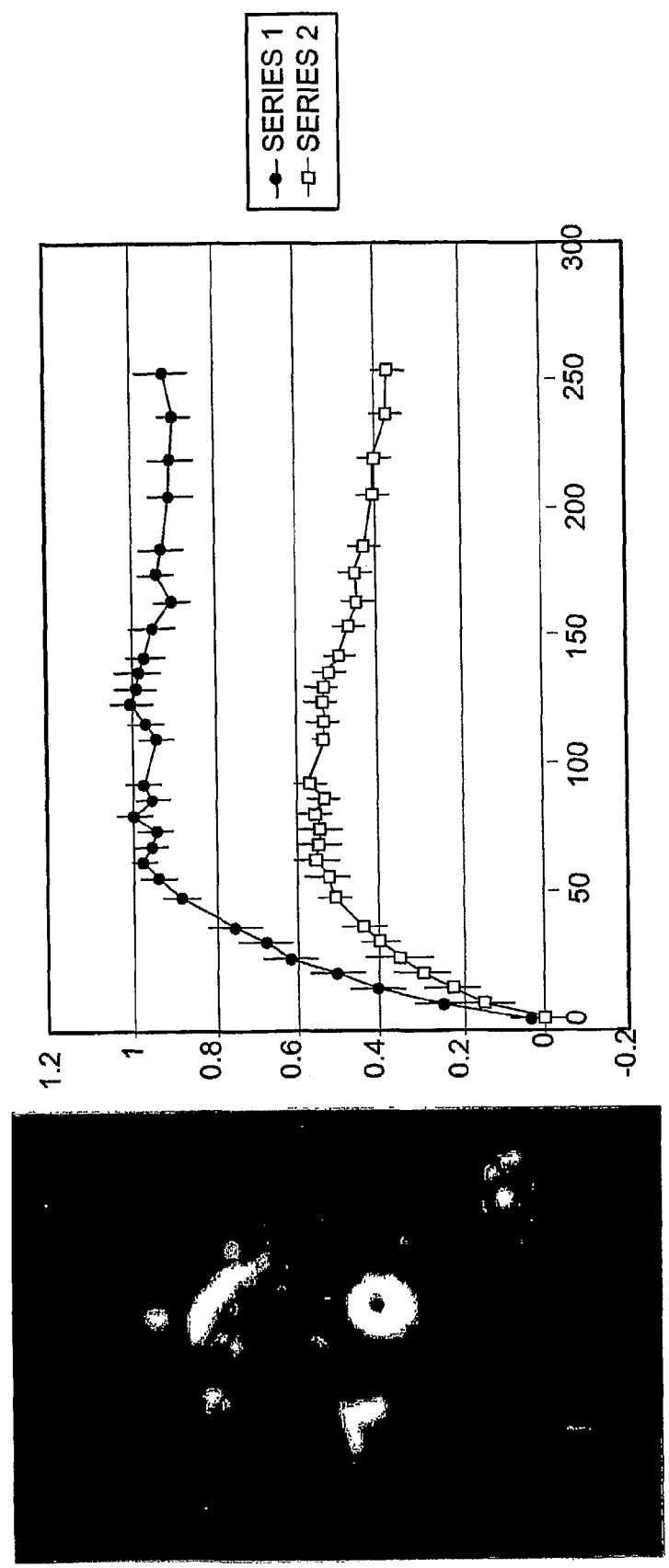
FIG. 16D is a T1 weighted image of an MPO mouse model after injection with $2Gd^{3+}$ complex. The relative CNR reached is 1.7-1.8 before the control side begins to decrease. The maximum relative CNR ratio is 2.5 and is reached at 254 minutes, 2.0 at 185 minutes.
Figure 16E:
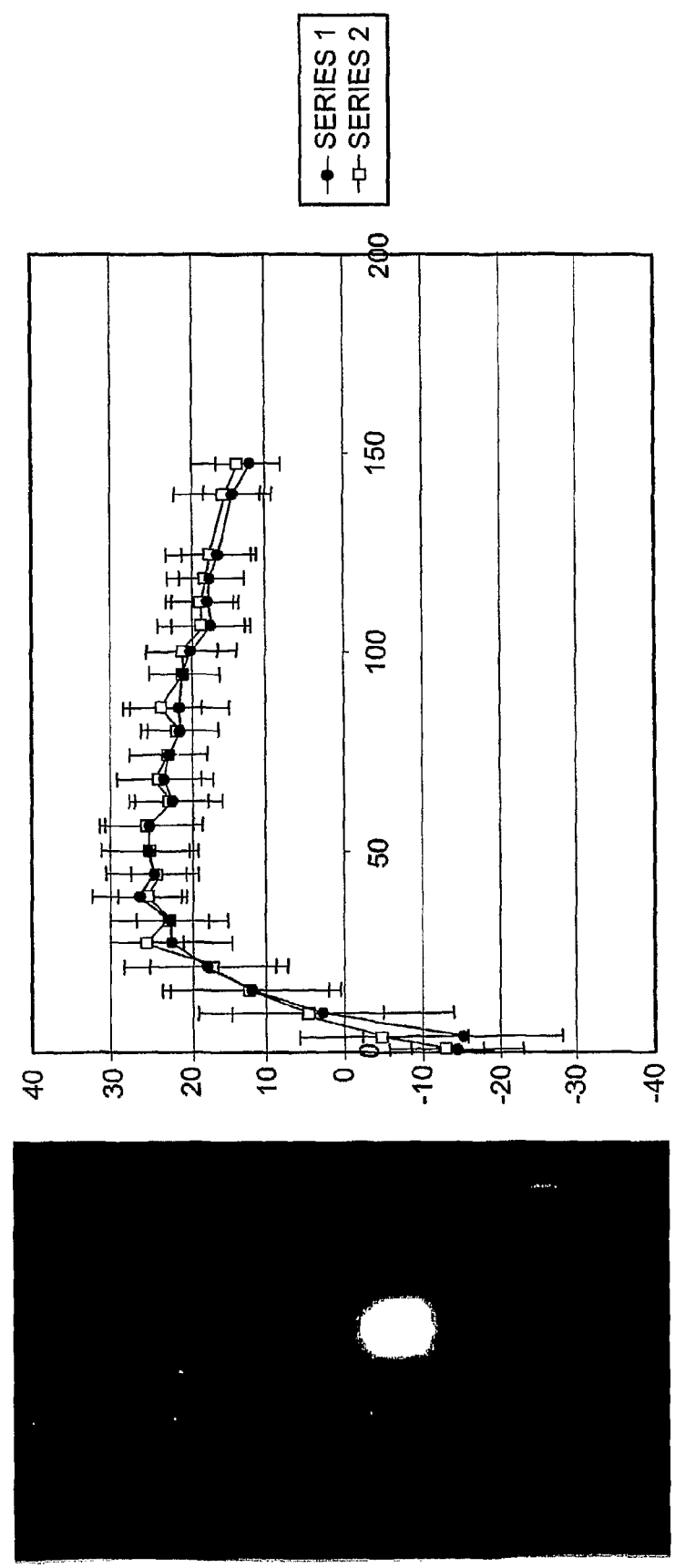
FIG. 16E is a T1 weighted image of an MPO mouse model after injection with $1Gd^{3+}$ complex.
Figure 16F:
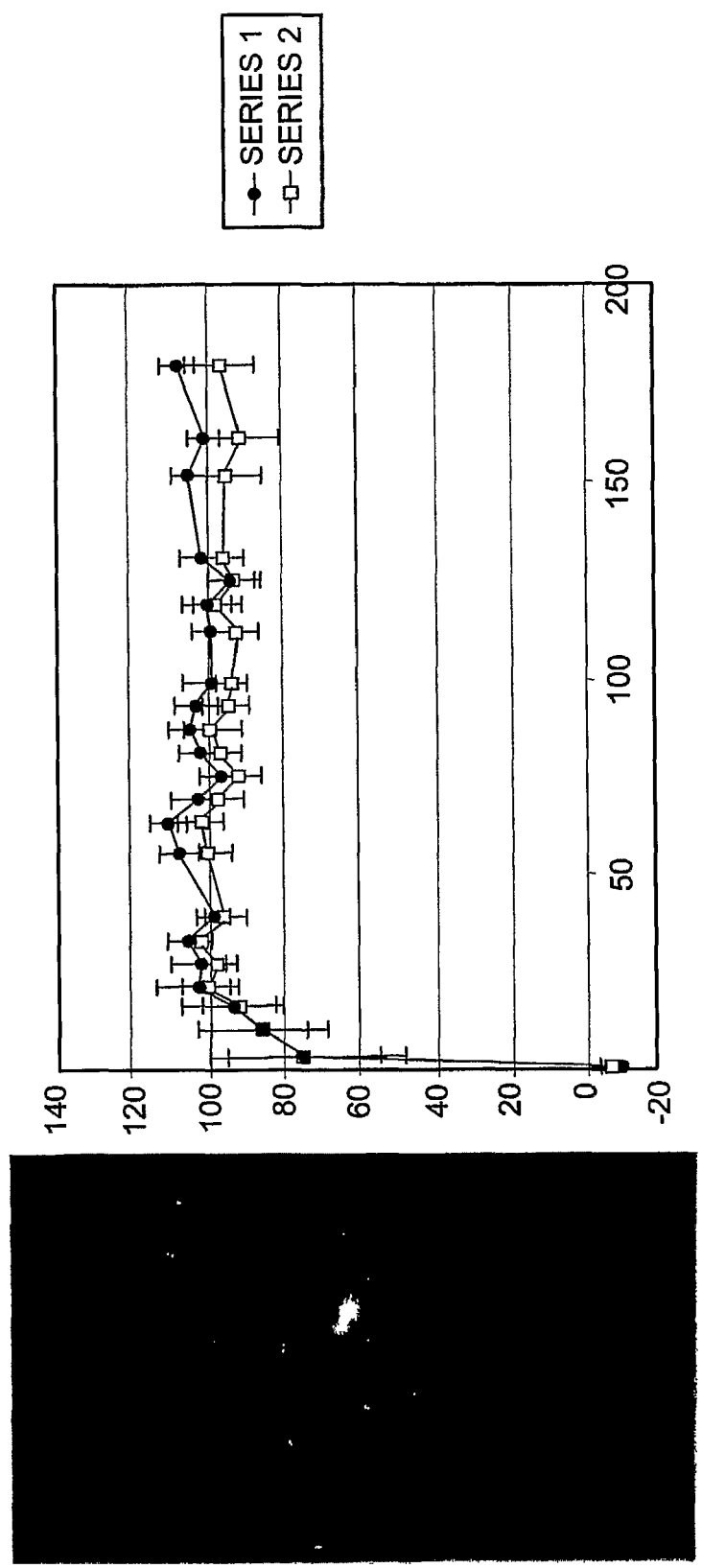
FIG. 16F shows a T1 weighted image of MPO mouse model after injection with $1Gd^{3+}$ complex.

To evaluate the monomeric substrates in vivo, we devised a mouse model that harbored 400 μL of Matrigel basement membrane matrix gel mixed 1:1 by volume with a solution containing 15 U of human MPO and glucose oxidase (as a source of hydrogen peroxide) that was injected into the right flank of the mouse. The left flank was injected with the enzyme-free Matrigel mixture. We subsequently performed T1-weighted MR imaging after the intravenous injection of Gd-DTPA-diSer substrate at the dose of 0.3 mM/Kg. FIG. 15 shows a typical MR image from this experiment. The comparison of MR signal intensities measured in the right (MPO-containing) and the left (control) flanks of the animal, showed that there was a 1.7-2.0-fold increase in the contrast-to-noise ratio over 3 hours post injection, confirming that the substrate in fact was highly sensitive for MPO activity in vivo. The same experiment performed with Magnevist (Gd-DTPA) did not show any difference in MPO-containing and control Matrigel implants measured over time. As the original in vitro results suggest, the signal increase observed in vivo could not be explained entirely by a r1 increase due to the oligomerization of oxidized substrate molecules but rather was consequence of a combined effect of: 1) longer circulation times that allowed $2Gd^{3+}$ to accumulate and get retained in Matrigel implant during the time required for MRI scan; 2) the possibility of cross-linking with matrix proteins present in the Matrigel. It has been found that MPO oxidized serotonin products bind to proteins and tissues. To determine if this was also the case for the monomeric substrate $2Gd^{3+}$, we performed eluting experiments in the presence of human plasma and, found that there is significantly more binding of the MPO-activated oligomers to plasma proteins compared to the substrate itself, by more than 3-fold.

Additional T1 weighted images of the MPO mouse model are shown in FIGS. 16A-16F. The maximum relative CNR ratio was 1.72 and was reached within 180 minutes.

Example III

General

Figure 17:
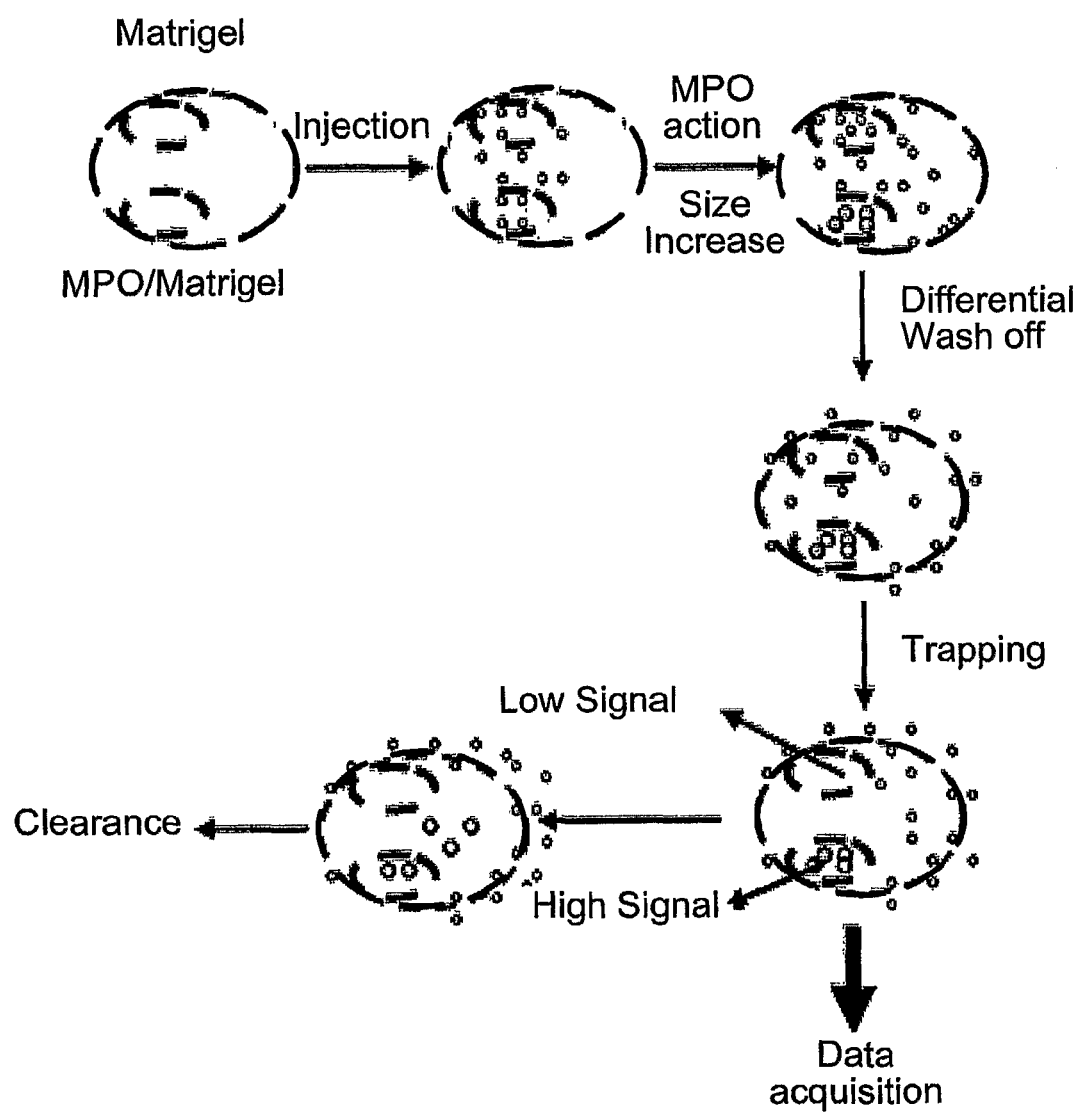
FIG. 17 is a schematic representation of a temporal accumulation believed to be involved with the "trapping" of the radiotracer substrate monomers within the MPO-rich targeted tissue.

We hypothesized that monomeric substrates (e.g., compound 3) could diffuse in the interstitium after the systemic administration and, upon in vivo reaction with MPO in presence of $H_2O_2$, could oligomerize and bind (e.g., crosslink) with proteins within the MPO-rich areas thereby creating a local increase of radioactivity. The above site-specific size increase was aimed to delay the elimination of the radiolabeled reaction product from the intersititum and, therefore, to induce a temporal specific "trapping" of the radiotracer within the MPO-rich targeted tissue (see FIG. 17).

Example III-A

Synthesis of Compound 3 and Ga Complex Formation

Synthesis of compound 3:1 mol eq of Deferoxamine mesylate (Sigma) were dissolved in dry dimethylsulfoxide. The solution was degassed with a stream of argon and kept under argon. Further, 2-(5-hydroxy-1H-indol-3-yl)acetic acid, 5 mol eq), DCC (5.5 molar eq) in dry pyridinine were added dropwise to the above solution. The solution was kept stirring under argon for 4 h followed by acetone addition and pouring of the reaction mixture into diethyl ether. The solution was kept overnight to yield a tan precipitate which was isolated by centrifugation. The solid was redissolved in a 1:2 v/v mixture of methanol:acetone (5 mL) and the solution was again poured onto 100 mL of diethyl ether to produce a yellowish precipitate which was isolated by centrifugation. The crude compound obtained by precipitation was further purified by preparative HPLC (C18, Vydac preparative column) using a gradient of acetonitrile in water from 0 to 70%.

Figure 18A:
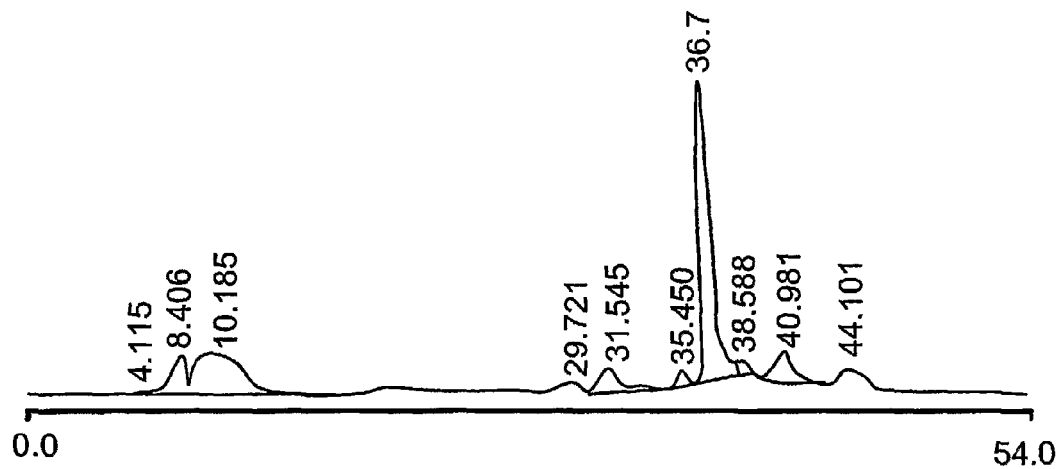
FIG. 18A is a chromatogram of the crude compound 3 reaction mixture after the precipitation with diethyl ether. The peak at 36.7 minutes was collected.
Figure 18B:
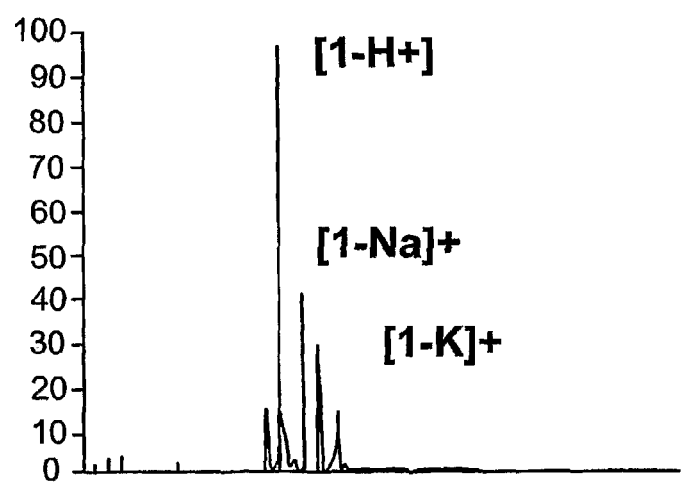
FIG. 18B is a MALDI-TOF mass spectrum of the material obtained by isolation of the peak at 36.7 minutes. The MW is coherent with the structure of 3.

FIG. 18A shows the chromatogram of the crude product after the precipitation. As can be seen from the chromatogram, the reaction yielded the desired compound alongside with minor impurities. The main peak of the chromatogram (rt=36.7 minutes) was easily isolated and submitted to MALDI-TOF which showed the main peak as corresponding protonated form of compound 3 (see FIG. 18B) The spectrum also showed minor peaks due to the formation of [Na-1]+ and [K-1]+.

Complex formation with unlabelled ("cold") Ga: Over a degassed $10^{-3}$M aqueous solution of compound 3 (1 mL), an equimolar amount of Ga(acac) (Aldrich) in 10 μL of ethanol was added. The mixture was stirred over argon at room temperature for several hours. At different time points, aliquots of the solution were extracted and brought to a concentration $5 \times 10^{-5}$ M and analyzed by using UV-visible spectrophotometry. The reaction was stopped by freezing the mixture in liquid nitrogen after the UV-visible spectra did not show further changes (approximately at 4 h). Complex formation by HPLC was >99% with no decomposition products.

Radiolabeling: Fifty μg of compound 3 (1 mg/ml [[please confirm]]) were mixed with 1 mCi $^{67}$Ga(citrate) solution in 0.7-1.0 ml saline and incubated for 2 hours under argon. Transchelation and purity was controlled by HPLC (Discovery C-18 column, 25×3 mm, Supelco) using 0-60% gradient of acetonitrile in water. The chelated product is referred to a Ga-3.

The possibility of chelate oxidation led to further labeling experiments concerning reaction optimization for exclusion of oxygen and decreasing reaction times. To assess labeling conditions, we first attempted labeling with "cold" Ga(III). During the reaction time the original UV absorption band in the range of 270-320 nm with a maximum at 280 nm increased in intensity and slightly shifted towards lower wavelengths (see FIG. 18A). After 4 hours the spectra remained unchanged at which point the product was isolated by lyophilization.

Figure 19A:
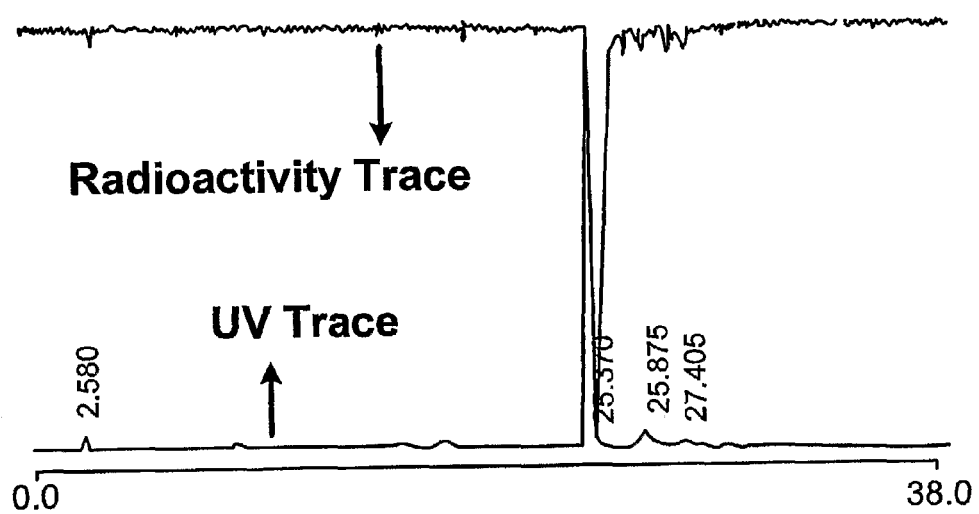
FIG. 19A shows the radio HPLC chromatogram of the [$^{67}$Ga]-3 labeling mixture superimposed on the UV-channel chromatogram of the [$^{67}$Ga]-3 labeling mixture.
Figure 19B:
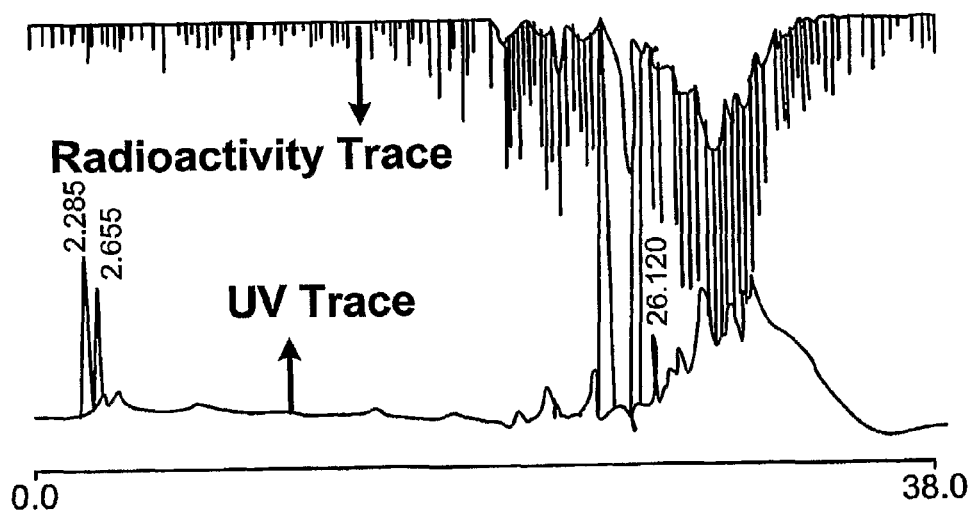
FIG. 19B shows the radio HPLC chromatogram of the [$^{67}$Ga]-3-MPO reaction mixture superimposed on the UV-channel chromatogram of the [$^{67}$Ga]-3-MPO reaction mixture.

The compound 3 was labeled with $^{67}$Ga via tranchelation from [$^{67}$Ga] citrate with the subsequent HPLC analysis shown in FIG. 19A). The chromatogram shows a complete disappearance of $^{67}$Ga(citrate) peak and a single new peak of radioactivity which allowed using labeling mixture without further purification in subsequent experiments. FIG. 19B shows the chromatogram of the labeled compound after reacting with the compound in the presence of MPO/$H_2O_2$. The latter showed several reaction products (UV absorbance trace) as well as a broad band (as opposite to a sharp peak in absence of MPO) on the radioactivity trace with no gallium activity at short retention times. This observation was consistent with the oligomerization pattern revealing no free gallium loss from the chelating unit suggesting stability of the complex.

Example III-B

In Vitro Testing and Matrigel Test

Figure 20A:
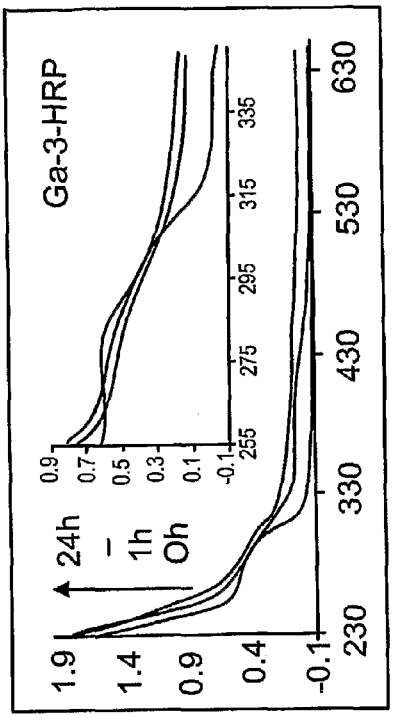
FIGS. 20A, 20B, and 20C are UV/VIS spectra of 3 and Ga-3; Ga-3+ HRP; and Ga-3+ MPO, respectively.
Figure 20C:
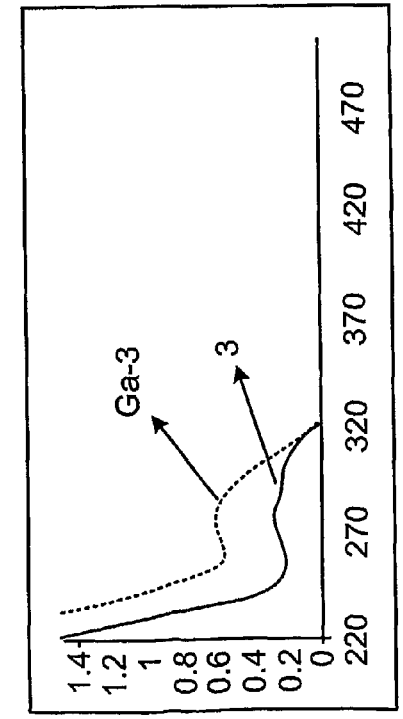
Figure 20B:
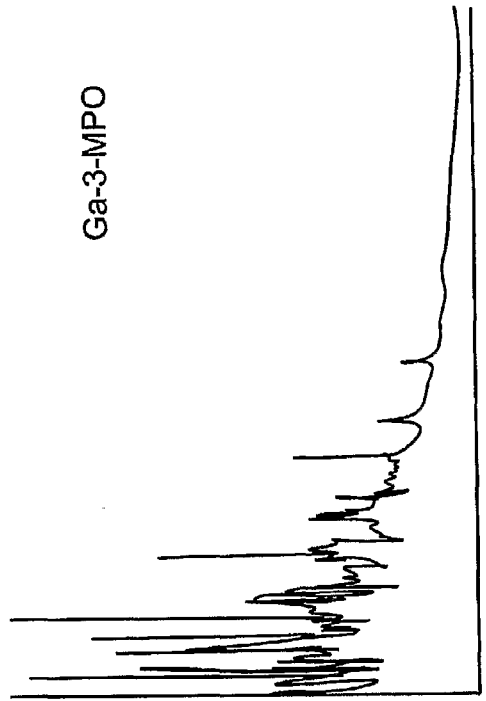
Figure 20D:
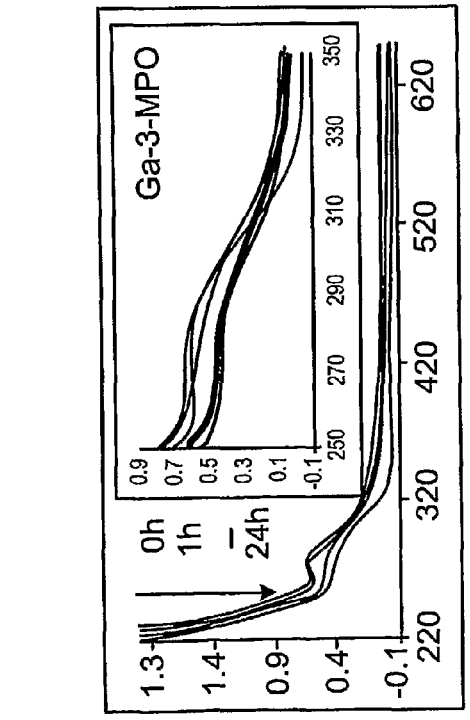
FIG. 20D is the MALDI-TOF mass spectrum of the product mixture obtained by reacting MPO with Ga-3.

Compound Ga-3 was further tested in vitro as an oxidoreductase reducing substrate. In a preliminary experiment, horseradish peroxidase (HRP), a model oxidoreductase, was used to test the possibility of enzyme-induced oligomerization. FIG. 20A shows UV-visible spectra of compounds 3 and Ga-3. FIG. 20B shows UV-visible spectra of compound Ga-3 with HRP in the presence of $H_2O_2$ at different reaction times (0, 1, 2, 4, 6 and 24 hours). Well-defined aromatic band centered at 280 nm broadened over the reaction time and extended beyond 330 nm with some residual absorption in the region 350-500 nm. Extension towards the visible range is associated with the extension of the aromatic system as could be expected in the event of oligomerization. After 6 hours no change was observed and the reaction reaches levels close to 90% of conversion after approximately 2 hours. If MPO was used instead of HRP, the obtained results (see FIG. 20C) were similar. The reaction between MPO and Ga-3 showed signs of oxidation and precipitation that were accounted for the decrease in absorbance shown in FIG. 20C. MALDI-TOF analysis of the reaction products (see FIG. 20D) showed complex mixtures of and indicated the presence of interaction between compound Ga-3 and the oxidoreductase as indicated by regular peak distributions of higher molecular weight.

Matrigel (Ewing sarcoma basal membrane extract, Beckton-Dickinson) (200 μl) was mixed with 8 μl MPO (1 mg/ml) or 1 μl HRP-positive control (1 mg/ml), 1 μl GO (1 mg/ml) and 1 μl 1M glucose on ice in a 96-well plate. The mixture was placed at 37° C. for 15 min and washed with PBS after Matrigel solidified. Two solutions containing 50 μl and 25 μl of [$^{67}$Ga]-3 (aliquots taken from a mixture of 200 μl 0.5 M ligand solution and 200 μl [$^{67}$Ga] citrate, about 200 μCi total) were added on top of Matrigel and incubated for 2 hours at 37

C with slow agitation in orbital shaker. The plate was washed 6 times with 250 µl of PBS (10 min incubation each wash) to remove non-bound [$^{67}$Ga]-3. The plate was exposed to a Phosphoimager plate (Molecular Dynamics/GE) for 3 min. After imaging, gels were removed from the wells and counted separately on a Gamma-counter (Wizard 1480, Perkin-Elmer).

Figure 21:
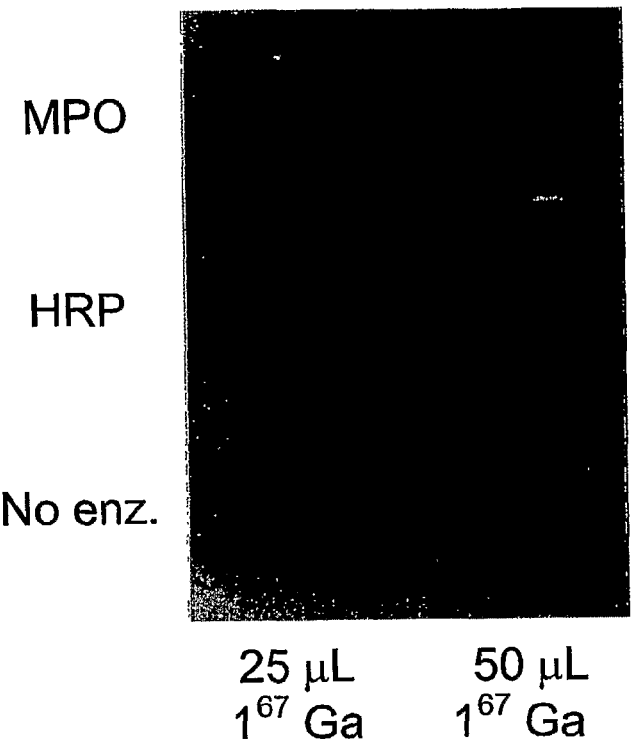
FIG. 21 is a series of images obtained from a well plate experiment monitoring the interaction of [$^{67}$Ga]-3 with MPO and HRP embedded in Matrigel. The table shows the numerical values of the plate wells in arbitrary units.

The previous experiment showed the possibility of oligomer formation. To assess further interactions, i.e., with proteins in the media, we incubated radiolabeled tracer in well-plate containing different combinations enzyme embedded in Matrigel. As hypothesized, wells containing either HRP or MPO show higher activity than the controls (FIG. 21). The signal enhancement obtained varied between 18% to 63%, depending on the enzyme used and local concentration. Wells containing HRP showed higher increase of signal which correlated with the faster kinetics characteristic to HRP-catalyzed reactions with the above class of substrates. The increase in substrate concentration led to higher signal levels.

In experiments performed in vitro we showed that upon MPO-mediated catalysis [$^{67}$Ga]-3 undergoes chemical modification that yields an overall increase of the radiotracer size. The well-plate experiment clearly demonstrated the interaction between the radiotracer with the proteins contained in the Matrigel. It is known that the oligomerization process, in absence of proteins, results in formation of short/medium oligomers with molecular weights/sizes far "smaller" than any other potential combinations resulting from the enzyme-substrate association. Upon completion of the reaction in the wells, the washing procedure resulted in the removal of most of those "small" aggregates, together with unreacted monomer, leaving mainly protein-bound radiotracer as a main source of signal intensity. The increase in size observed in vitro is likely to be associated with a drastic change in the in vivo behavior of the compound resulting in an accumulation within the inflamed tissue due to hindered elimination from the MPO-containing site.

Example III-C

In Vivo (SPECT) Imaging and Biodistribution

SPECT imaging and biodistribution: A solution of 80-100 µCi of [$^{67}$Ga]—I in 200 µl of saline were injected intravenously into mice prepared as follows: ten-week old C57BL6 male mice (Jackson Laboratories) were injected with 400 µL of a mixture of Matrigel™ (Beckton-Dickinson) and MEM (Cambrex) into the thighs of each mouse one hour prior to imaging. The right thigh mixture also contained 15 U of MPO and 4 µg of glucose oxidase (Calbiochem), while the left thigh mixture contained no enzyme to serve as an internal control. Glucose oxidase was included to ensure local generation of hydrogen peroxide. The animals were imaged 3 hours after injection on a high resolution X-SPECT/CT system (Gamma Medica). Six hours after injection, the animals were sacrificed and biodistribution was determined in major organs. The % dose accumulated per gram of major organs was determined by using a gamma counter.

To test our hypothesis in vivo, we prepared an inflammation model in mice. The model consisted in the subcutaneous implantation (1 hour before radiotracer injection) of Matrigel/MPO/GO mixture in the right thigh of each mouse. The left thigh mixture contained no enzyme and served as internal control. Matrigel is a basement membrane matrix gel that can be used for immobilizing human MPO and peroxide-generating enzyme. After injecting [$^{67}$Ga]—I intravenously, SPECT/CT imaging was performed 4 hours later.

Figure 22A:
FIGS. 22A and 22B are fused CT/SPECT images of the MPO/Matrigel implant (right) vs. control implant (left) in a mouse.
Figure 22B:
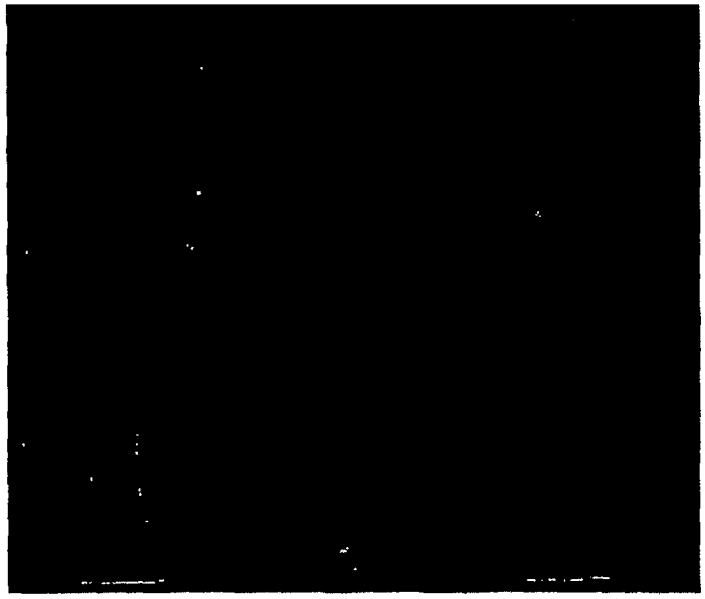

FIGS. 22A and 22B each show mouse SPECT/CT fusion images. As expected, the implant on the right in each of the figures showed higher intensity than the implant on the left (control), thereby demonstrating preferential radiotracer uptake at the site containing MPO activity. The model used included an internal control since the only difference between right and left thigh of the mouse was the presence of the enzyme and, thus, non-specific accumulation of the substrate could be easily accounted for.

Figure 23:
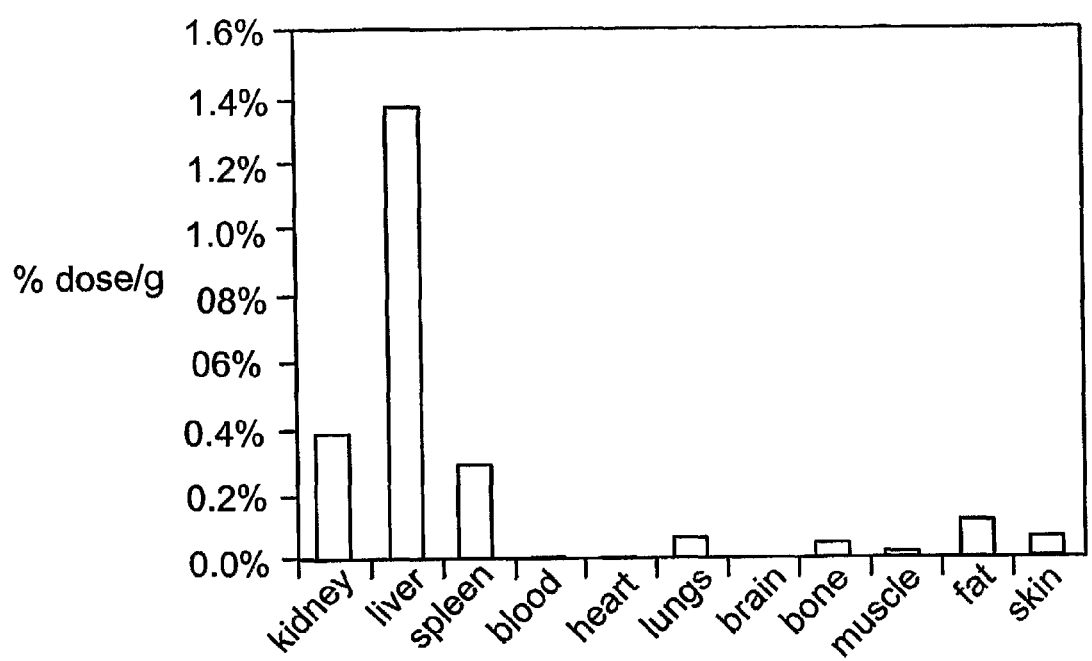
FIG. 23 is a graphical representation of biodistribution of the initial dose about 6 hours after the injection of [$^{67}$Ga]—I in mice.

Biodistribution experiments performed 6 hours after the injection (n=4 mice) showed that major fraction of the initial dose injected was efficiently eliminated. The residual radioactivity found was found in the bowel (~7.8%) with the rest of the organs showing levels below 0.5% except for liver that showed levels close to 1.4% (see FIG. 23). At this stage the difference between right and left thigh was still around 60%, showing the potential of this approach.

In vivo experiment showed that the accumulation was due to the aforementioned factors since the physiological conditions were similar in both experimental and control implants. This observation rules out the signal difference that would originate due to the non-specific accumulation as a result of enhanced vascular permeability. Furthermore, due to the experiment time-span, transferrin transchelation of Gallium in vivo could be also ruled out. Our in vivo results can be explained in terms of diffusion parameters since the radical formation/reaction is generally known to be diffusion-limited. Thus, higher local concentrations would improve the chance of radical collision and would improve the possibility of macromolecular formation as opposite to radical quenching at lower concentration.

Example IV

Example IV-A

Synthesis and Analytical Procedures

Mono (hydroxytryptamido)-DOTA, gadolinium salt (5-HT-DOTA(Gd) and dopamine-DOTA(Gd) were synthesized according the methods described herein. Bis-tyramide-DTPA(Gd) and bis-5-HT-DTPA(Gd) were synthesized according the methods described herein.

Indium-111 labeled bis-5-HT-DTPA was prepared by using transchelation from $^{111}$In-oxiquinoline complex (oxine, Cardinal Health, Cleveland Ohio). To prepare $^{111}$In-bis-5-HT-DTPA, 50 µg of bis-5-HT-DTPA (1 mg/ml) were mixed with 1 mCi $^{111}$In-oxiquinoline solution in 0.7-1.0 ml saline and incubated for 1 hour under argon. Transchelation and purity was controlled by HPLC (Discovery C-18 column, 25×3 mm, Supelco) using 0-55% gradient of acetonitrile in water. Human myeloperoxidase was obtained from BioDesign, Inc., and its activity determined by using the method described by Klebanoff. To determine if the Gd compounds were substrates for human MPO, MPO-mediated oligomerization was monitored by size exclusion HPLC and by measuring $\Delta T_1$ on a Bruker Minispec 120 NMR spectrometer using a standard inversion recovery sequence. The degree of oligomerization was determined by mass spectroscopy (MALDI-MS).

Example IV-B

Substrate Binding to Plasma Components

The follow experiments were performed to determine the effect of MPO-activated substrate oligomerization with plasma proteins to form larger aggregate. Human plasma was extracted from healthy donors by the use of Polymorphprep (Accurate Chemicals) and centrifugation according to the manufacturer's instructions. Aliquots of 3 mM solution of bis-5-HT-DTPA(Gd) was mixed with aliquots of $^{111}$In-bis-5-HT-DTPA as a tracer, with or without human plasma and with and without MPO/$H_2O_2$. These solutions were loaded on Bio-Rad Biospin P-6 minicolumns and plasma was separated according to the method suggested by the manufacturer. Radioactivity retained in the columns and the eluted material were counted separately in 1480 Wizard gamma counter (Perkin-Elmer) and the fraction of radioactivity bound to proteins was calculated (n=3 independent experiments).

Example IV-C

MR Imaging

The MR imaging experiments were performed on a 1.5 T GE Excite scanner and a 4.7 T Bruker Pharmascan scanner. For all MR imaging experiments, precontrast T2-(TR=2000, TE=100, ETL=8, NEX=4, fast spin echo sequence) and T1-weighted images (TR=500, TE=11, NEX=4, spin echo sequence) with fat saturation were initially performed to locate the gels or area of inflammation. The substrates (0.3 mmol/kg) were subsequently injected via the tail vein of the mouse. The mouse was immediately imaged after the injection of the contrast agent using multiple T1-weighted sequences with fat saturation for at least 3 hours.

Example IV-D

Mouse Models

Ten-week old C57BL6 male mice were obtained from Jackson Laboratories. A total of 22 mice were used for the study.
1. MPO/Matrigel imaging experiments: Matrigel™ (Beckton-Dickinson), a Ewing's sarcoma basement membrane matrix gel was used to immobilize human MPO and glucose oxidase (to supply $H_2O_2$ required for detecting MPO oxidative activity, Calbiochem). This was chosen to reflect deposits of human MPO in inflamed tissue in a mouse model. 400 μL of a mixture of Matrigel™ and MEM (Cambrex) was injected slowly into the thighs of each mouse one hour prior to imaging. The right thigh mixture also contained 15 U of MPO and 4 U of glucose oxidase (Calbiochem), while the left thigh mixture contained no enzyme and thus serves as an internal control. A total of 15 mice were used (3 mice each for 5-HT-DOTA(Gd), bis-5-HT-DTPA(Gd), bis-5-HT-DTPA-$^{111}$In, bis-tyramide-DTPA(Gd), and DTPA(Gd)).
2. LPS/Matrigel experiments (n=3): This model was developed to induce endogenous mouse MPO secretion and activation. 200 μL total volume Matrigel containing 10% heparin was injected slowly into the thighs of the mice 4 days prior to imaging. The right-sided mixture also contained *E. coli* lipopolysaccharide (LPS) at 10 μg/mL. One mouse was sacrificed for immunohistochemistry.
3. Myositis experiments (n=4): LPS at 100 μg/mL in PBS was injected into each mouse intramuscularly in the right flank to produce myositis. The mice are imaged 24 hours after injection.

Example IV-E

SPECT-CT Imaging and Biodistribution (n=3)

80-100 μCi of $^{111}$In-bis-5-HT-DTPA in 200 μL of saline was injected intravenously into three mice prepared in the same manner as in the MPO/Matrigel MR imaging experiments. The animals were imaged 3 hours after injection on a high resolution X-SPECT/CT system (Gamma Medica). Six hours after injection, the animals were sacrificed and biodistribution was determined in major organs. The % dose accumulated per gram of major organs was determined by using the 1480 Wizard gamma counter (Perkin-Elmer).

Example IV-F

Immunohistochemistry

The tissues were fixed in paraformaldehyde, immersed in 30% sucrose and used for paraffin embedding within several days. A diluted solution of rabbit polyclonal anti-MPO antibody (AbCam, Cambridge Mass., 1:10 in 10% horse serum/PBS) was used as primary antibody followed with anti-rabbit peroxidase conjugate and staining with diaminobenzidine. The antibodies had cross-reactivity with mouse MPO and thus were suitable for mouse tissues.

Example IV-G

Statistical Analysis

For normalized signal intensity measured on T1-weighted images, mean±standard deviation (SD) values were calculated in regions of interest (ROI). Contrast-to-noise (CNR) ratios were computed for each ROI according to the formula $$CNR = \frac{ROI(\text{site}) - ROI(\text{muscle})}{SD(\text{noise})}$$

The CNRs were then normalized. Statistical significance of the relative CNR curves induced by the injection of the agents was calculated by using the Kolmogorov-Smirnov test. P<0.05 was considered to indicate a statistically significant difference.

Figure 24:
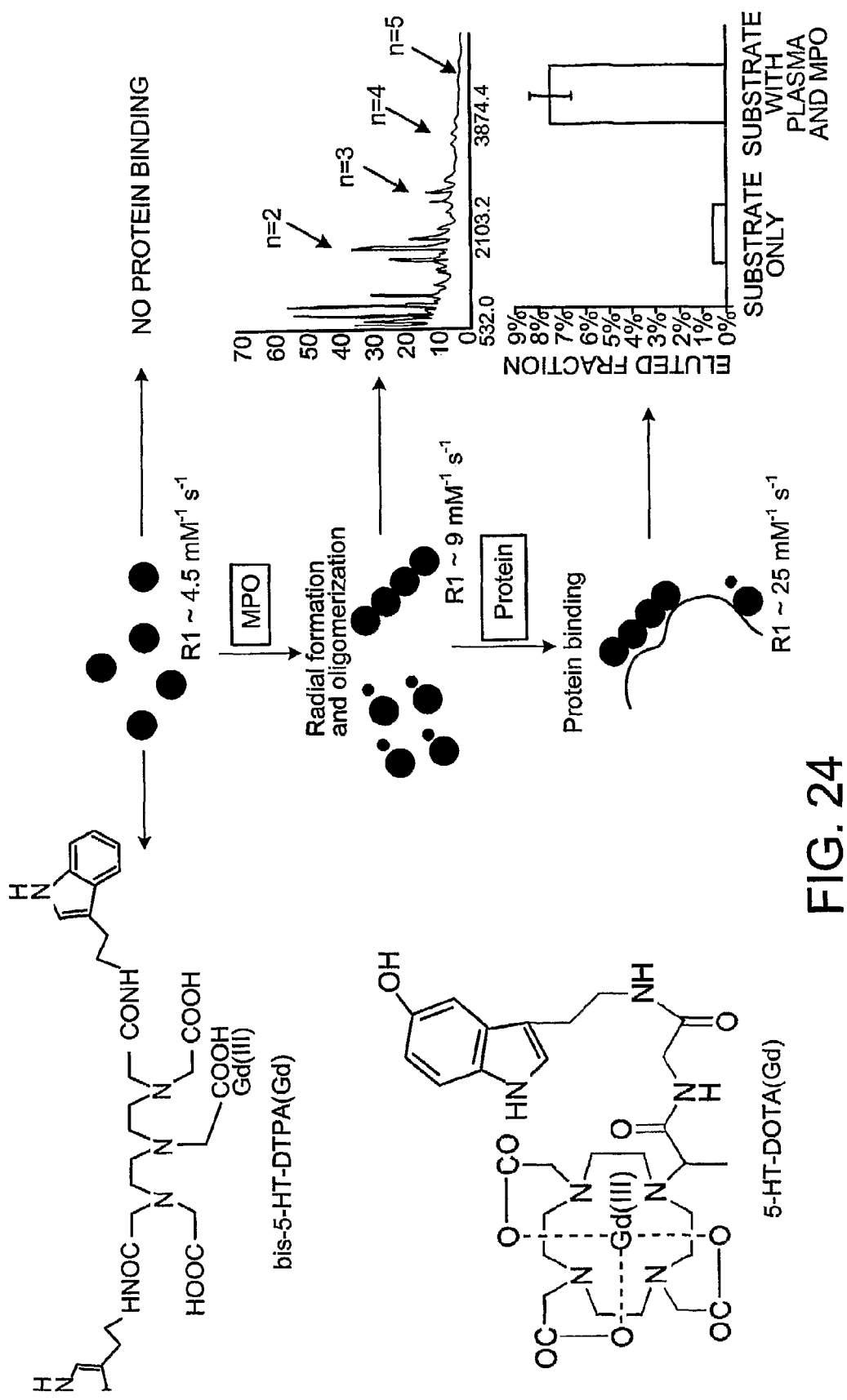
FIG. 24 is a diagram showing (i) the chemical structures of two electron-donating paramagnetic monomeric substrates for peroxidase-mediated reactions of $H_2O_2$ reduction (leftmost panel); (ii) a schematic representation of the chemical reactions that result in the formation of monomeric substrate-containing product(s) having a higher molecular weight (and increased relaxivity) than that of the starting monomeric substrate itself (middle panel); and (iii) representative mass spectrum (b) and radiolabeled elution data (c) for the oligomerized and protein bound monomeric substrates, respectively (rightmost panel).

FIG. 24 shows the structures of the MPO substrates (leftmost panel), 5-HT-DOTA(Gd) and bis-5-HT-DTPA(Gd), and a schematic representation of the changes that can occur in the presence of a target enzyme (e.g., MPO) and proteins (middle panel). When activated by MPO and hydrogen peroxide ($H_2O_2$), the substrates shown in FIG. 24 are oligomerized up to 5 units, as shown by the mass spectroscopy for bis-5-HT-DTPA(Gd) (rightmost panel of FIG. 24). Furthermore, in the presence of plasma proteins and after activation by MPO/$H_2O_2$, there is markedly increased elution of $^{111}$In radioactivity (rightmost panel of FIG. 24), demonstrating association of the MPO-activated products to plasma proteins. In these experiments, the monomers did not show any significant plasma protein binding.

MR Imaging of Human MPO Implants

FIGS. 25A, 25B, 25C, and 25D show representative images and the time course of the contrast enhancement (expressed as relative CNR). As expected, no visual difference or CNR difference was noted when injected with DTPA(Gd) (p=0.98, FIG. 25A). On the other hand, there was increased enhancement of the right side compared to the control left side without MPO when injected with 5-HT-DOTA(Gd) (p<0.001, FIG. 25C). The maximum relative CNR ratio achieved was 1.7.

We also synthesized di-substituted paramagnetic substrates to take advantage of potentially increased efficacy of polymerization by having multiple reducing moieties linked to the same paramagnetic chelate. The injection of bis-tyramide-DTPA(Gd) did not result in significantly increased enhancement of the implant (p=0.62, FIG. 25B). However, when injected with bis-5-HT-DTPA(Gd), there was significantly increased enhancement in the presence of MPO (p<0.001, FIG. 25D). This enhancement appeared more pronounced than for 5-HT-DOTA(Gd). The maximum relative CNR increase was 1.9-times in the first 143 minutes. At 240 minutes, there is a maximum relative CNR increase of 2.5-times because of increased washout of the substrate from the control implant on the contralateral side.

Endogenous Mouse MPO can be Induced by LPS and Reported by MPO-Sensitive MR Agents FIGS. 26D and 26E show the immunohistochemistry images from the LPS/Matrigel experiments (FIGS. 26A and 26B show the magnetic resonance images, and FIG. 26C shows the relative CNR time curve). We found that at the site with Matrigel embedded with LPS (right), there is recruitment of a large number of cells that stained positive for MPO. The site without LPS (left) was nearly free of cells and the few cells present stained negative for MPO. In addition, in the presence of endogeneous mouse MPO, we found a 1.3-fold increased enhancement on the MPO side (p<0.001) when injected with bis-5-HT-DTPA(Gd), but no significant difference in enhancement when injected with DTPA(Gd) (p=0.82). Mouse MPO levels are generally known to be only about 10-20% that of human MPO (Rausch P G, Moore T G. Granule enzymes of polymorphonuclear neutrophils: A phylogenetic comparison. Blood 1975; 46:913-919).

MR Imaging of Inflammation (Myositis)

After confirming that LPS can trigger endogenous mouse MPO release, an in vivo inflammation (myositis) model was developed. FIGS. 26A and 26B show some representative images demonstrating enhancement of the inflamed muscles after intravenous injection of every one of the tested agents at 6 minutes. Using DTPA(Gd) as the control, only 5-HT-DOTA(Gd) and bis-5-HT-DTPA(Gd), but not dopamine-DOTA(Gd) (a phenolic derivative similar to the 5-HT substrates but which does not react with MPO, p=0.99), generated prolonged enhancement that persisted more than 50 minutes after injection. This is further underscored in FIG. 26C, which plots the relative CNR versus time of an area of inflammation. In the case of the 5-HT-DOTA(Gd) (p=0.039) and bis-5-HT-DTPA(Gd) (p=0.017), there is continued increase in CNR resulting from activation by MPO. The slight delay to reach peak CNR for these two substrates is caused by the MPO activation and oligomerization, which in in vitro settings took about 15 minutes to reach 90% completion (9).

Scintigraphic Confirmation of Target Accumulation

We injected intravenously $^{111}$In-bis-5-HT-DTPA into mice (n=3) with implanted Matrigel/MPO combination as described above for the MR experiments. SPECT-CT imaging was obtained at 3 hours after injection as the time curves suggested (see FIGS. 25A-D). FIG. 27A shows a fused SPECT-CT image, demonstrating high radiotracer retention in the region containing human MPO. Conversely, the left Matrigel implant without MPO showed lower activity. There was a 2.3±0.3-fold increase in the radioactivity of the right leg (with MPO) vs. the left leg (without MPO).

Biodistribution

Biodistribution data obtained at 6 h post injection (see FIG. 27B) showed that 90% of the injected dose had been excreted. Most of the remaining injected dose was found in the spleen, bowel, kidney, and liver, with other organs showing little radioactivity, a similar biodistribution profile as other gadolinium chelates. When we compared radioactivities of the dissected Matrigel implants, we found that there was greater than 4-fold increase in count in the gel with embedded MPO. The above results are consistent with significant focal accumulation of the activated agents in response to MPO.

MPO-mediated oligomerization of the monomeric substrates resulted in products having increased molecular mass (relative to the monomeric substrates themselves) and, consequently, increased MR signal and delayed clearance from tissue. The MPO-mediated oxidation products also bound to and/or crosslinked with plasma proteins causing more local accumulation. The association with proteins also further contributes to the increase of the MR signal due to $R_1$ increase.

While tyramide based paramagnetic substrates were rapidly oxidized by horseradish peroxidase, and that di-substituted tyramide substrates demonstrated even better relative relaxivity increase in the presence of horseradish peroxidase, bis-tyramide-DTPA(Gd) did not demonstrate significantly increased enhancement in the presence of MPO, and demonstrated a relative CNR curve similar to that of DTPA(Gd). This may be due to the slower kinetics tyramide-DOTA(Gd) generally exhibited with MPO.

In the human MPO implant experiments, which simulates MPO-rich tissues, we found that bis-5-HT-DTPA(Gd) resulted in the highest CNR, with 5-HT-DOTA(Gd) being slightly lower. We also performed this experiment at 4.7 T (not shown), and found a relative CNR increase of 1.8-fold before significant wash-out of the control side occurred, similar to the findings at 1.5 T (1.9-fold) for bis-5-HT-DTPA(Gd). These data show that significant relative increased enhancement is still obtained at high magnetic field strengths.

In addition to increased CNR, there is prolonged enhancement for the MPO substrates, persisting at a very high level to nearly an hour before falling off gradually, shown in the myositis experiments. Therefore, 5-HT-DOTA(Gd) and bis-5-HT-DTPA(Gd) have significantly different pharmacokinetics from the control substrates dopamine-DOTA(Gd) and DTPA(Gd). These findings are consistent with our hypothesis that the increased size of the MPO-converted oligomers cannot quickly diffuse out and thus remain at the area of inflammation significantly longer than the unconverted, smaller substrates.

This hypothesis was also supported by the radiolabeled elution experiments. In this experiment, the columns only eluted molecules greater than 6,000 Daltons. Therefore, only molecules that have been bound to plasma proteins would be eluted. After activation with MPO in the presence of plasma, a much larger fraction of radioactivity was eluted, consistent with increased binding to plasma proteins (see FIG. 24). This is also consistent with the findings by Heuther et al. (Heuther G, Reimer A, Schmidt F, Schuff-Werner P, Brudny M M. Oxidation of the indole nucleus of 5-hydroxytryptamine and formation of dimers in the presence of peroxidase and H2O2. J Neural Transm Suppl 1990; 32:249-257) that oxidized 5-HT products by peroxidase demonstrated significant binding to albumin, plasma proteins, and tissues, but not 5-HT itself. Together with the larger size of the MPO-activated products, this increased binding affinity of the activated product serves to prolong the pharmacokinetics of the agents in the presence of MPO.

We then reasoned if our hypothesis regarding the accumulation of the activated products in MPO-containing sites were correct, we should also be able to also perform scintigraphic imaging of MPO activity. The $^{111}$In-bis-5-HT-DTPA imaging results shown in FIGS. 27A and 27B confirm that there is large focal accumulation of MPO-converted products. This approach can have advantages over existing methods of imaging inflammation (e.g., not requiring the extraction and manipulation of the patient's blood, while retaining the advantage of indium-111 use; or higher specific to inflammation by showing only sites where myeloperoxidase is active, i.e., where there is active inflammation causing damage). Gadolinium-labeled agents give the same functionality to MR imaging, but also with the added benefit of the much higher resolution achievable by MR imaging. Because of the signal amplification activated by MPO, there would be dosimetry advantages as well.

OTHER EMBODIMENTS

A number of embodiments of the invention have been described. Nevertheless, it will be understood that various modifications may be made without departing from the spirit and scope of the invention. For example, two or more chelating moieties can be incorporated into a single monomeric substrate molecule. Accordingly, other embodiments are within the scope of the following claims.

What is claimed is:
1. A monomeric substrate of forula (I):

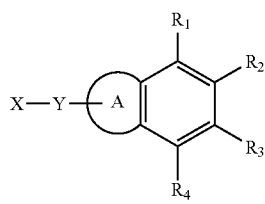

(I)

wherein

X is selected from the group consisting of 1,4,7,10-tetraazacyclodo-decane-N,N',N'',N'''-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazacyclododecane, and 1,4,8,11-tetraazacyclotetra-decane-N,N',N'',N'''-tetraacetic acid;

Y comprises a linker moiety;

each of $R_1$, $R_2$, $R_3$, and $R_4$ is selected from the group consisting of hydrogen, hydroxy, $C_1$-$C_6$ alkoxy, amino, $C_1$-$C_6$ alkylamino, $C_1$-$C_6$ dialkylamino, and $C_1$-$C_6$ alkylcarboxamido; provided that at least one of $R_1$, $R_2$, $R_3$, and $R_4$ is hydroxyl;

A is:

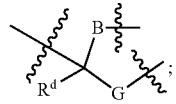

wherein

B is $CR^aR^b$ or $NR^c$;

$R^d$ is hydrogen or $R^d$ together with one of $R^a$, $R^b$ or $R^c$ is a bond;

G is $NR^e$, O, or S;

each of $R^a$ and $R^b$ is, independently, hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate; or one of $R^a$ and $R^b$ is hydrogen, $C_1$-$C_6$ alkyl, $C_3$-$C_8$ cycloalkyl, haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate, and the other together with $R^d$ is a bond;

$R^c$ is hydrogen or $C_1$-$C_6$ alkyl; or $R^c$ together with $R^d$ is a bond; and $R^e$ is hydrogen or $C_1$-$C_6$ alkyl.

2. The monomeric substrate of claim 1, wherein G is $NR^e$.

3. The monomeric substrate of claim 2, wherein $R^e$ is hydrogen.

4. The monomeric substrate of claim 1, wherein B is $CR^aR^b$.

5. The monomeric substrate of claim 4, wherein $R^a$ is hydrogen and $R^b$ together with $R^d$ is a bond.

6. A monomeric substrate of formula (I):

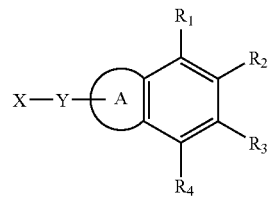

(I)

wherein

X is selected from the group consisting of 1,4,7,10-tetraazacyclodo-decane-N,N',N'',N'''-tetraacetic acid, 1,4,7,10-tetraaza-cyclododecane-N,N',N'''-triacetic acid, 1,4,7-tris(carboxymethyl)-10-(2'-hydroxypropyl)-1,4,7,10-tetraazacyclododecane, and 1,4,8,11-tetraazacyclotetra-decane-N,N',N'',N'''-tetraacetic acid;

Y comprises a linker moiety;

each of $R_1$, $R_2$, $R_3$, and $R_4$ is selected from the group consisting of hydrogen, hydroxy, $C_1$-$C_6$ alkoxy, amino, $C_1$-$C_6$ alkylamino, $C_1$-$C_6$ dialkylamino, and $C_1$-$C_6$ alkylcarboxamido; provided that at least one of $R_1$, $R_2$, $R_3$, and $R_4$ is hydroxyl;

A is:

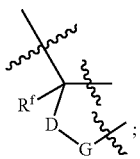

wherein

D is CR$^g$R$^h$ or NR$^j$;

R$^f$ is hydrogen or R$^f$ together with one of R$^g$, R$^h$ or R$^j$ is a bond;

G is NR$^e$, O, or S;

R$^e$ is hydrogen or C$_1$-C$_6$ alkyl; or R$^e$ together with one of R$^g$ or R$^h$ is a bond;

each of R$^g$ and R$^h$ is, independently, hydrogen, C$_1$-C$_6$ alkyl, C$_3$-C$_8$ cycloalkyl, C$_1$-C$_4$ haloalkyl, C$_7$-C$_{12}$ aralkyl, 6-12 membered heteroaralkyl, 3-8 membered heterocyclyl, C$_3$-C$_8$ cycloalkenyl, 3-8 membered heterocycloalkenyl, C$_6$-C$_{12}$ aryl, 5-12 membered heteroaryl, C$_2$-C$_6$ alkenyl, C$_2$-C$_6$ alkynyl, C$_1$-C$_6$ alkoxy, 7-12 membered aryloxy, 7-12 membered thioaryloxy, C$_1$-C$_4$ haloalkoxy, halo, hydroxy, carboxy, carboxylate, aminocarbonyl, C$_1$-C$_4$ alkylaminocarbonyl, C$_1$-C$_4$ dialkylaminocarbonyl, C$_1$-C$_6$ alkoxycarbonyl, cyano, nitro, amino, C$_1$-C$_4$ alkyl amino, C$_1$-C$_4$ dialkyl amino, mercapto, C$_1$-C$_6$ thioalkoxy, SO$_3$H, sulfate, or phosphate; or one of R$^g$ and R$^h$ is hydrogen, C$_1$-C$_6$ alkyl, C$_3$-C$_8$ cycloalkyl, haloalkyl, C$_7$-C$_{12}$ aralkyl, 6-12 membered heteroaralkyl, 3-8 membered heterocyclyl, C$_3$-C$_8$ cycloalkenyl, 3-8 membered heterocycloalkenyl, C$_6$-C$_{12}$ aryl, 5-12 membered heteroaryl, C$_2$-C$_6$ alkenyl, C$_2$-C$_6$ alkynyl, C$_1$-C$_6$ alkoxy, 7-12 membered aryloxy, 7-12 membered thioaryloxy, C$_1$-C$_4$ haloalkoxy, halo, hydroxy, carboxy, carboxylate, aminocarbonyl, C$_1$-C$_4$ alkylaminocarbonyl, C$_1$-C$_4$ dialkylaminocarbonyl, C$_1$-C$_6$ alkoxycarbonyl, cyano, nitro, amino, C$_1$-C$_4$ alkyl amino, C$_1$-C$_4$ dialkyl amino, mercapto, C$_1$-C$_6$ thioalkoxy, SO$_3$H, sulfate, or phosphate, and the other together with R$^e$ or R$^f$ is a bond; and R$^j$ is hydrogen or C$_1$-C$_6$ alkyl; or R$^j$ together with R$^e$ or R$^f$ is a bond.

7. The monomeric substrate of claim 6, wherein G is NR$^e$.

8. The monomeric substrate of claim 7, wherein R$^e$ is hydrogen.

9. The monomeric substrate of claim 6, wherein D is CR$^g$R$^h$.

10. The monomeric substrate of claim 9, wherein R$^g$ is hydrogen and R$^h$ together with R$^f$ is a bond.

11. A monomeric substrate of formula (I):

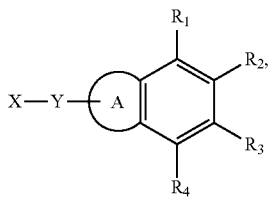

(I)

X is selected from the group consisting of 1,4,7,10-tetraazacyclo-decane-N,N',N",N'"-tetraacetic acid, 1,4,7,10-tetraaza-cyclododecane-N,N',N"-triacetic acid, 1,4,7-tris(carboxymethyl)-10-(2'-hydroxypropyl)-1,4,7,10-tetraazacyclododecane, and 1,4,8,11-tetraazacyclotetra-decane-N,N',N",N'"-tetraacetic acid;

Y comprises a linker moiety;

A is:

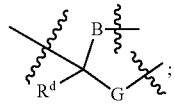

wherein

B is CR$^a$R$^b$ or NR$^c$;

R$^d$ is hydrogen or R$^d$ together with one of R$^a$, R$^b$ or R$^c$ is a bond;

G is NR$^e$, O, or S;

each of R$^a$ and R$^b$ is, independently, hydrogen, C$_1$-C$_6$ alkyl, C$_3$-C$_8$ cycloalkyl, C$_1$-C$_4$ haloalkyl, C$_7$-C$_{12}$ aralkyl, 6-12 membered heteroaralkyl, 3-8 membered heterocyclyl, C$_3$-C$_8$ cycloalkenyl, 3-8 membered heterocycloalkenyl, C$_6$-C$_{12}$ aryl, 5-12 membered heteroaryl, C$_2$-C$_6$ alkenyl, C$_2$-C$_6$ alkynyl, C$_1$-C$_6$ alkoxy, 7-12 membered aryloxy, 7-12 membered thioaryloxy, C$_1$-C$_4$ haloalkoxy, halo, hydroxy, carboxy, carboxylate, aminocarbonyl, C$_1$-C$_4$ alkylaminocarbonyl, C$_1$-C$_4$ dialkylaminocarbonyl, C$_1$-C$_6$ alkoxycarbonyl, cyano, nitro, amino, C$_1$-C$_4$ alkyl amino, C$_1$-C$_4$ dialkyl amino, mercapto, C$_1$-C$_6$ thioalkoxy, SO$_3$H, sulfate, or phosphate; or one of R$^a$ and R$^b$ is hydrogen, C$_1$-C$_6$ alkyl, C$_3$-C$_8$ cycloalkyl, C$_1$-C$_4$ haloalkyl, C$_7$-C$_{12}$ aralkyl, 6-12 membered heteroaralkyl, 3-8 membered heterocyclyl, C$_3$-C$_8$ cycloalkenyl, 3-8 membered heterocycloalkenyl, C$_6$-C$_{12}$ aryl, 5-12 membered heteroaryl, C$_2$-C$_6$ alkenyl, C$_2$-C$_6$ alkynyl, C$_1$-C$_6$ alkoxy, 7-12 membered aryloxy, 7-12 membered thioaryloxy, C$_1$-C$_4$ haloalkoxy, halo, hydroxy, carboxy, carboxylate, aminocarbonyl, C$_1$-C$_4$ alkylaminocarbonyl, C$_1$-C$_4$ dialkylaminocarbonyl, C$_1$-C$_6$ alkoxycarbonyl, cyano, nitro, amino, C$_1$-C$_4$ alkyl amino, C$_1$-C$_4$ dialkyl amino, mercapto, C$_1$-C$_6$ thioalkoxy, SO$_3$H, sulfate, or phosphate, and the other together with R$^d$ is a bond;

R$^c$ is hydrogen or C$_1$-C$_6$ alkyl; or R$^c$ together with R$^d$ is a bond; and R$^e$ is hydrogen or C$_1$-C$_6$ alkyl;

or

A is:

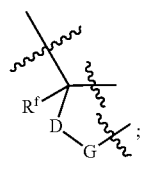

wherein

D is CR$^g$R$^h$ or NR$^j$;

R$^f$ is hydrogen or R$^f$ together with one of R$^g$, R$^h$ or R$^j$ is a bond;

G is NR$^e$, O, or S;

R$^e$ is hydrogen or C$_1$-C$_6$ alkyl; or R$^e$ together with one of R$^g$ or R$^h$ is a bond;

each of R$^g$ and R$^h$ is, independently, hydrogen, C$_1$-C$_6$ alkyl, C$_3$-C$_8$ cycloalkyl, C$_1$-C$_4$ haloalkyl, C$_7$-C$_{12}$ aralkyl, 6-12 membered heteroaralkyl, 3-8 membered heterocyclyl, C$_3$-C$_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate; or one of $R^g$ and $R^h$ is hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_5$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate, and the other together with $R^e$ or $R^f$ is a bond; and $R^j$ is hydrogen or $C_1$-$C_6$ alkyl; or $R^j$ together with $R^e$ or $R^f$ is a bond; and each of $R_1$, $R_2$, $R_3$, and $R_4$ is selected from the group consisting of hydrogen, hydroxy, $C_1$-$C_6$ alkoxy, amino, $C_1$-$C_6$ alkylamino, $C_1$-$C_6$ dialkylamino, and $C_1$-$C_6$ alkylcarboxamido; provided that at least one of $R_1$, $R_2$, $R_3$, and $R_4$ is hydroxyl; wherein $R_1$, $R_2$, $R_3$, or $R_4$ is at a meta position relative to the OH substituent, and is selected from the group consisting of amino, $C_1$-$C_6$ alkylamino, $C_1$-$C_6$ dialkylamino, and $C_1$-$C_6$ alkylcarboxamido.

12. The monomeric substrate of claim 1, wherein one of $R_2$ and $R_3$ is hydroxy and the other is hydrogen.

13. The monomeric substrate of claim 12, wherein $R_1$ and $R_4$ are hydrogen.

14. The monomeric substrate of claim 1, wherein the monomeric substrate further comprises a paramagnetic or superparamagnetic metal atom or ion.

15. The monomeric substrate of claim 14, wherein the paramagnetic or superparamagnetic metal atom or ion is a transition metal atom or ion.

16. The monomeric substrate of claim 14, wherein the paramagnetic or superparamagnetic metal atom or ion is a lanthanide atom or ion.

17. The monomeric substrate of claim 14, wherein the metal ion is selected from the group consisting of an iron ion, a dysprosium ion, a europium ion and a manganese ion.

18. The monomeric substrate of claim 14, wherein the metal ion is a gadolinium ion.

19. A monomeric substrate of formula (I):

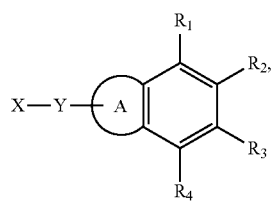

(I)

X is selected from the group consisting of 1,4,7,10-tetraazacyclodo-decane-N,N',N'',N'''-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazacyclododecane, and 1,4,8,11-tetraazacyclotetra-decane-N,N',N'',N'''-tetraacetic acid;

Y comprises a linker moiety;

A is:

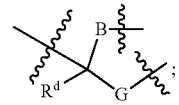

wherein

B is $CR^aR^b$ or $NR^c$;

$R^d$ is hydrogen or $R^d$ together with one of $R^a$, $R^b$ or $R^c$ is a bond;

G is $NR^e$, O, or S;

each of $R^d$ and $R^b$ is, independently, hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate; or one of $R^a$ and $R^b$ is hydrogen, $C_1$-$C_6$ alkyl, $C_3$-$C_8$ cycloalkyl, haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate, and the other together with $R^d$ is a bond;

$R^c$ is hydrogen or $C_1$-$C_6$ alkyl; or $R^c$ together with $R^d$ is a bond; and $R^e$ is hydrogen or $C_1$-$C_6$ alkyl;

or

A is

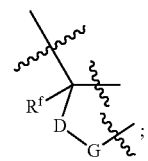

wherein

D is $CR^gR^h$ or $NR^j$;

$R^f$ is hydrogen or $R^f$ together with one of $R^g$, $R^h$ or $R^j$ is a bond;

G is $NR^e$, O, or S;

$R^e$ is hydrogen or $C_1$-$C_6$ alkyl; or $R^e$ together with one of $R^g$ or $R^h$ is a bond;

each of $R^g$ and $R^h$ is, independently, hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate; or one of $R^g$ and $R^h$ is hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate, and the other together with $R^e$ or $R^f$ is a bond; and $R^j$ is hydrogen or $C_1$-$C_6$ alkyl; or $R^j$ together with $R^e$ or $R^f$ is a bond; and;

each of $R_1$, $R_2$, $R_3$, and $R_4$ is selected from the group consisting of hydrogen, hydroxy, $C_1$-$C_6$ alkoxy, amino, $C_1$-$C_6$ alkylamino, $C_1$-$C_6$ dialkylamino, and $C_1$-$C_6$ alkylcarboxamido; provided that at least one of $R_1$, $R_2$, $R_3$, and $R_4$ is hydroxyl;

wherein the monomeric substrate further comprises a radionuclide.

20. The monomeric substrate of claim 19, wherein the radionuclide is selected from the group consisting of $^{111}$In, $^{99m}$Tc, $^{94m}$Tc, $^{67}$Ga, $^{68}$Ga.

21. The monomeric substrate of claim 1, wherein Y comprises a structure selected from the group consisting of: an amino acid, an oligopeptide comprising 2-6 amino acid residues, a nucleotide, an oligonucleotide comprising 2-6 nucleotide residues, a $C_3$-$C_{12}$ alkyl group, a polyethyleneimine, a saccharide, an oligosaccharide, a medium chain fatty acid, a polyamidoamine, a polyarylic acid, and a polyalcohol.

22. A monomeric substrate of formula (I):

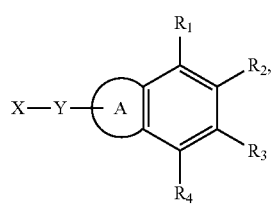

(I)

X is selected from the group consisting of 1,4,7,10-tetraazacyclodo-decane-N,N',N'',N'''-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazacyclododecane, and 1,4,8,11-tetraazacyclotetra-decane-N,N,N'',N'''-tetraacetic acid;

Y comprises a linker moiety;

A is:

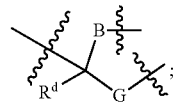

wherein
B is $CR^aR^b$ or $NR^c$;
$R^d$ is hydrogen or $R^d$ together with one of $R^a$, $R^b$ or $R^c$ is a bond;
G is $NR^e$, O, or S;
each of $R^a$ and $R^b$ is, independently, hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate; or one of $R^a$ and $R^b$ is hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate, and the other together with $R^d$ is a bond;
$R^c$ is hydrogen or $C_1$-$C_6$ alkyl; or $R^c$ together with $R^d$ is a bond; and
$R^e$ is hydrogen or $C_1$-$C_6$ alkyl;
or
A is:

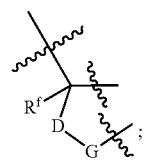

wherein
D is $CR^gR^h$ or $NR^j$;
$R^f$ is hydrogen or $R^f$ together with one of $R^g$, $R^h$ or $R^j$ is a bond;
G is $NR^e$, O, or S;
$R^e$ is hydrogen or $C_1$-$C_6$ alkyl; or $R^e$ together with one of $R^g$ or $R^h$ is a bond;
each of $R^g$ and $R^h$ is, independently, hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate; or one of $R^g$ and $R^h$ is hydrogen, $C_1$-$C_6$ alkyl, $C_3$-$C_8$ cycloalkyl, $C_1$-$C_4$ haloalkyl, $C_7$-$C_{12}$ aralkyl, 6-12 membered heteroaralkyl, 3-8 membered heterocyclyl, $C_3$-$C_8$ cycloalkenyl, 3-8 membered heterocycloalkenyl, $C_6$-$C_{12}$ aryl, 5-12 membered heteroaryl, $C_2$-$C_6$ alkenyl, $C_2$-$C_6$ alkynyl, $C_1$-$C_6$ alkoxy, 7-12 membered aryloxy, 7-12 membered thioaryloxy, $C_1$-$C_4$ haloalkoxy, halo, hydroxy, carboxy, carboxylate, aminocarbonyl, $C_1$-$C_4$ alkylaminocarbonyl, $C_1$-$C_4$ dialkylaminocarbonyl, $C_1$-$C_6$ alkoxycarbonyl, cyano, nitro, amino, $C_1$-$C_4$ alkyl amino, $C_1$-$C_4$ dialkyl amino, mercapto, $C_1$-$C_6$ thioalkoxy, $SO_3H$, sulfate, or phosphate, and the other together with $R^e$ or $R^f$ is a bond; and $R^j$ is hydrogen or $C_1$-$C_6$ alkyl; or R together with $R^e$ or $R^f$ is a bond; and each of $R_1$, $R_2$, $R_3$, and $R_4$ is selected from the group consisting of hydrogen, hydroxy, $C_1$-$C_6$ alkoxy, amino, $C_1$-$C_4$ alkylamino, $C_1$-$C_6$ dialkylamino, and $C_1$-$C_6$ alkylcarboxamido;

provided that at least one of $R_1$, $R_2$, $R_3$, and $R_4$ is hydroxyl;

wherein Y comprises an amino acid or oligopeptide containing 2-6 amino acid residues.

23. The monomeric substrate of claim 22, wherein the oligopeptide comprises a glycine residue.

24. A monomeric substrate, wherein the monomeric substrate comprises the formula:

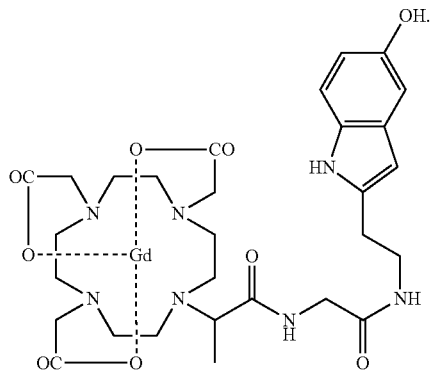

* * * * *

UNITED STATES PATENT AND TRADEMARK OFFICE
CERTIFICATE OF CORRECTION

PATENT NO. : 8,153,784 B2
APPLICATION NO. : 11/631720
DATED : April 10, 2012
INVENTOR(S) : Alexei Bogdanov It is certified that error appears in the above-identified patent and that said Letters Patent is hereby corrected as shown below:

Title Page, item (56); Col. 2, line 17, Delete "liglnin" and insert -- lignin --

In Col. 68, line 11, in Claim 1, before "dialkylaminocarbonyl" insert -- $C_1$-$C_4$ --

In Col. 68, line 15, in Claim 1, before "haloalkyl" insert -- $C_1$-$C_4$ --

In Col. 69, line 30, in Claim 6, before "haloalkyl" insert -- $C_1$-$C_4$ --

In Col. 71, line 14, in Claim 11, delete "$C_1$-$C_5$;" and insert -- $C_1$-$C_6$ --

In Col. 72, line 17, in Claim 19, delete "$R^d$" and insert -- $R^a$ --

In Col. 72, line 30, in Claim 19, before "haloalkyl" insert -- $C_1$-$C_4$ --

In Col. 72, line 46, in Claim 19, delete "A is" and insert -- A is: --

In Col. 73, line 23, in Claim 19, delete "and;" and insert -- and --

In Col. 73, line 66, in Claim 22, delete "N,N,N",N''"" and insert -- N,N',N'',N''' --

In Col. 75, line 16, in Claim 22, delete "R" and insert -- $R^j$ --

In Col. 75, line 20, in Claim 22, delete "$C_1$-$C_4$" and insert -- $C_1$-$C_6$ --

Signed and Sealed this
Twenty-eighth Day of August, 2012

David J. Kappos
*Director of the United States Patent and Trademark Office*